(12) United States Patent
Howell et al.

(10) Patent No.: US 11,850,380 B2
(45) Date of Patent: Dec. 26, 2023

(54) MEDICAL ARTICLE SECUREMENT SYSTEMS

(71) Applicant: C. R. Bard, Inc., Franklin Lakes, NJ (US)

(72) Inventors: Glade H. Howell, Draper, UT (US); Matthew W. Bown, West Bountiful, UT (US); Jeremy A. Pearce, West Jordan, UT (US); Anthony S. Elangovan, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 634 days.

(21) Appl. No.: 16/930,196

(22) Filed: Jul. 15, 2020

(65) Prior Publication Data

US 2020/0338311 A1 Oct. 29, 2020

Related U.S. Application Data

(63) Continuation of application No. 14/914,623, filed on Feb. 25, 2016, now Pat. No. 10,716,918, which is a (Continued)

(51) Int. Cl.
*A61M 25/02* (2006.01)

(52) U.S. Cl.
CPC ....... *A61M 25/02* (2013.01); *A61M 2025/028* (2013.01); *A61M 2025/0246* (2013.01);
(Continued)

(58) Field of Classification Search
CPC .......... A61M 25/02; A61M 2025/0246; A61M 2025/0253; A61M 2025/0266;
(Continued)

(56) References Cited

U.S. PATENT DOCUMENTS

| 4,224,937 | A | 9/1980 | Gordon |
| 4,397,647 | A | 8/1983 | Gordon |

(Continued)

FOREIGN PATENT DOCUMENTS

| CN | 1282259 A | 1/2001 |
| EP | 1 029 555 A2 | 8/2000 |

(Continued)

OTHER PUBLICATIONS

AU 2013312357 filed Feb. 5, 2015 Examination Report dated Mar. 20, 2017.
(Continued)

*Primary Examiner* — Deanna K Hall
(74) *Attorney, Agent, or Firm* — Rutan & Tucker LLP

(57) ABSTRACT

A medical article, such as a catheter, is secured with respect to a patient with a securement device. The securement device may include a retainer and anchor pad. Certain devices may further include, for example, straps, flaps, dressings, slots, and recesses for securing the medical article to the patient. The retainer may include a recess and/or a channel. At least one surface of the retainer may be coated with an adhesive. A support member may be coupled to the retainer. The support member may include a channel configured to receive a proximally extending portion of the medical article.

35 Claims, 50 Drawing Sheets

Related U.S. Application Data continuation of application No. PCT/US2014/054395, filed on Sep. 5, 2014, which is a continuation-in-part of application No. PCT/US2013/058606, filed on Sep. 6, 2013.

(60) Provisional application No. 61/868,778, filed on Aug. 22, 2013, provisional application No. 61/698,251, filed on Sep. 7, 2012.

(52) U.S. Cl.
CPC ............ *A61M 2025/0253* (2013.01); *A61M 2025/0266* (2013.01); *A61M 2025/0273* (2013.01)

(58) Field of Classification Search
CPC .... A61M 2025/0273; A61M 2025/028; A61M 2005/1586; A61M 5/158
See application file for complete search history.

(56) References Cited

U.S. PATENT DOCUMENTS

| | | | |
|---|---|---|---|
| 4,897,082 A | 1/1990 | Erskine | |
| 5,018,516 A | 5/1991 | Gilman | |
| 5,192,273 A | 3/1993 | Bierman | |
| 5,344,415 A | 9/1994 | DeBusk et al. | |
| 5,380,294 A | 1/1995 | Persson | |
| 5,456,671 A | 10/1995 | Bierman | |
| 5,911,707 A | 6/1999 | Wolvek et al. | |
| 5,916,199 A | 6/1999 | Miles | |
| 6,224,571 B1 | 5/2001 | Bierman | |
| 6,551,285 B1 | 4/2003 | Bierman | |
| D492,411 S | 6/2004 | Bierman | |
| 6,827,706 B2 | 12/2004 | Tollini | |
| 7,294,752 B1 | 11/2007 | Propp | |
| 7,766,877 B1 | 8/2010 | Watson et al. | |
| 8,419,689 B2 * | 4/2013 | Fink | A61M 25/02 206/363 |
| 8,486,004 B1 * | 7/2013 | Propp | A61M 25/02 604/48 |
| 10,099,007 B2 | 10/2018 | Mosa et al. | |
| 10,549,070 B2 | 2/2020 | Howell et al. | |
| 2001/0011164 A1 * | 8/2001 | Bierman | A61M 25/02 604/180 |
| 2001/0025159 A1 | 9/2001 | Fleischer | |
| 2002/0026152 A1 | 2/2002 | Bierman | |
| 2002/0115954 A1 | 8/2002 | Worthley | |
| 2004/0133226 A1 | 7/2004 | Buckman et al. | |
| 2004/0158209 A1 | 8/2004 | Wright | |
| 2004/0204685 A1 | 10/2004 | Wright et al. | |
| 2004/0204691 A1 | 10/2004 | Yashiro et al. | |
| 2007/0043326 A1 | 2/2007 | Navarro et al. | |
| 2009/0182283 A1 * | 7/2009 | Sloan | A61M 25/02 604/180 |
| 2010/0100049 A1 | 4/2010 | Godfrey | |
| 2010/0198161 A1 | 8/2010 | Propp | |
| 2011/0282291 A1 | 11/2011 | Ciccone | |
| 2011/0313362 A1 | 12/2011 | Bierman | |
| 2012/0232490 A1 | 9/2012 | Andino | |
| 2012/0271240 A1 * | 10/2012 | Andino | A61M 25/02 604/180 |
| 2013/0150796 A1 * | 6/2013 | Souza | A61M 25/02 604/180 |
| 2013/0310754 A1 * | 11/2013 | Kutsch | A61M 25/02 604/180 |
| 2015/0224285 A1 | 8/2015 | Howell et al. | |
| 2016/0206855 A1 | 7/2016 | Howell et al. | |

FOREIGN PATENT DOCUMENTS

| | | |
|---|---|---|
| EP | 1698368 A1 | 9/2006 |
| JP | 2008-302237 A | 12/2008 |
| WO | 01/91847 A2 | 12/2001 |
| WO | 2011/060197 A1 | 5/2011 |
| WO | 2015035238 A1 | 3/2015 |

OTHER PUBLICATIONS

CN 201380046709.9 filed Mar. 6, 2015 Office Action dated Dec. 30, 2016.
CN 201380046709.9 filed Mar. 6, 2015 Office Action dated Mar. 28, 2018.
CN 201380046709.9 filed Mar. 6, 2015 Office Action dated Sep. 20, 2017.
CN 201480048406.5 filed Mar. 2, 2016 Office Action dated Sep. 4, 2018.
EP 13836131.6 filed Feb. 24, 2015 Extended European Search Report dated Apr. 8, 2016.
EP 14842629.9 filed Mar. 1, 2016 Extended European Search Report dated Mar. 30, 2017.
JP 2015-531257 filed Mar. 6, 2015 Office Action dated Apr. 16, 2018.
JP 2015-531257 filed Mar. 6, 2015 Office Action dated Jun. 12, 2017.
PCT/US2014/054395 filed Sep. 5, 2014 International Search Report and Written Opinion dated Dec. 22, 2014.
RU 2015109380 filed Mar. 18, 2015 Office Action dated Aug. 25, 2017.
RU 2015109380 filed Mar. 18, 2015 Office Action dated Jan. 18, 2018.
U.S. Appl. No. 14/424,971, filed Feb. 27, 2015 Final Office Action dated Jul. 3, 2019.
U.S. Appl. No. 14/424,971, filed Feb. 27, 2015 Final Office Action dated Sep. 13, 2018.
U.S. Appl. No. 14/424,971, filed Feb. 27, 2015 Non-Final Office Action dated Aug. 14, 2017.
U.S. Appl. No. 14/424,971, filed Feb. 27, 2015 Non-Final Office Action dated Feb. 28, 2018.
U.S. Appl. No. 14/424,971, filed Feb. 27, 2015 Notice of Allowance dated Sep. 23, 2019.
U.S. Appl. No. 14/914,623, filed Feb. 25, 2016 Final Office Action dated Jan. 2, 2019.
U.S. Appl. No. 14/914,623, filed Feb. 25, 2016 Non-Final Office Action dated Jan. 13, 2020.
U.S. Appl. No. 14/914,623, filed Feb. 25, 2016 Non-Final Office Action dated May 14, 2018.
U.S. Appl. No. 14/914,623, filed Feb. 25, 2016 Notice of Allowance dated Apr. 8, 2020.
U.S. Appl. No. 14/914,623, filed Feb. 25, 2016 Restriction Requirement dated Feb. 5, 2018.

* cited by examiner

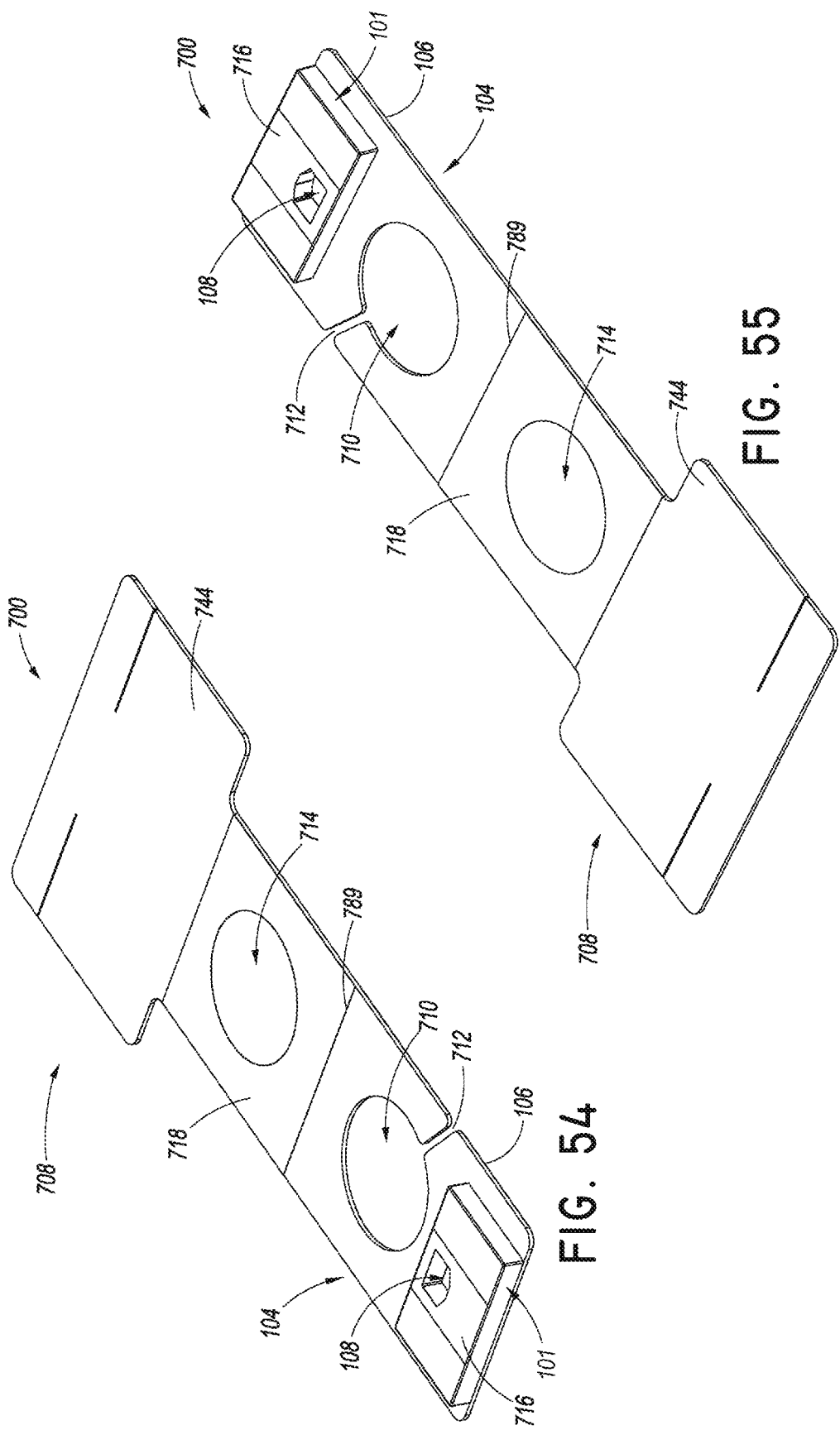

MEDICAL ARTICLE SECUREMENT SYSTEMS

CROSS-REFERENCE TO RELATED APPLICATIONS

This application is a continuation of U.S. patent application Ser. No. 14/914,623, now U.S. Pat. No. 10,716,918, which is a U.S. national stage application under 35 U.S.C. § 371 of International Application No. PCT/US2014/054395, filed Sep. 5, 2014, which is a continuation-in-part of International Application No. PCT/US2013/058606, filed Sep. 6, 2013, which claims priority under 35 U.S.C. § 119(e) to U.S. Provisional Application No. 61/698,251, filed Sep. 7, 2012, and to U.S. Provisional Application No. 61/868,778, filed Aug. 22, 2013, each of which is hereby incorporated by reference in its entirety into this application.

BACKGROUND

Field

The present invention relates generally to techniques, systems, and devices for securing a catheter, catheter extension set, and/or other medical article to a patient.

Description of the Related Art

Medical patients are often in need of repetitious administering of fluids or medications, or repetitious draining of fluids. It is very common in the medical industry to utilize medical tubing to provide various liquids or solutions to a patient. For example, medical tubing such as a catheter is often used to introduce fluids and medications directly into the patient or to withdraw fluids from the patient. In many cases, the catheter remains in place for many days. In some instances, a catheter may be attached to a patient for an even lengthier period of time, and may require minimal movement for proper functioning.

It is often advantageous to restrict the movement of the catheter. A moving catheter may cause discomfort to the patient, restrict the administering of fluids or medications or the draining of fluids, cause infection, or become dislodged from the patient unintentionally. In order to keep the catheter or other medical tubing properly positioned for the duration of treatment, the catheter or medical tubing can be stabilized on the patient in a variety of ways. Most commonly, the medical provider may attempt to restrict movement of the catheter by securing the distal end of the catheter, or a portion of a medical device connected to the catheter such as a connector fitting, to the patient using tape. Medical providers commonly place long pieces of tape across the distal end of the catheter, often in a crisscross pattern, to secure the catheter distal end to the patient. This securement is intended to inhibit disconnection between the catheter and the patient or between the catheter and another medical article, such as a drainage tube, as well as to prevent the catheter from catching on other objects, such as on a bed rail.

SUMMARY OF THE INVENTIONS

The devices, systems, and methods of the present disclosure have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments," one will understand how the features of this disclosure provide several advantages over other securement systems.

One aspect is a securement system comprising a medical article having an elongated body and a stabilization device having a retainer and an anchor pad. The retainer may have a proximal side, a distal side, and an upper side. The retainer may have a recess and a channel disposed within the retainer. The channel may extend from the recess to the proximal side of the retainer. At least a portion of the elongated body may be disposed within the recess. At least a portion of the elongated body may extend through the channel and beyond the proximal side of the retainer. The retainer may include at least one adhesive surface. The adhesive surface may be disposed on at least a portion of an upwardly facing surface of the retainer. The channel may have a lateral width less than a lateral width of the recess. The retainer may include at least one abutment configured to contact a proximal facing surface of the elongated body to prevent the elongated body from moving in at least the proximal direction. The at least one abutment may be disposed between the recess and the channel. The abutment may be configured to contact a distal facing surface of the elongated body to prevent the elongated body from moving in at least a distal direction.

Another aspect is a retainer configured to secure a medical article having an elongated body. The retainer may comprise a proximal side, a distal side, a bottom side, and a top side. A recess may be disposed in the top side of the retainer. The recess may be configured to receive a first portion of the elongated body. A channel may extend from the recess through the proximal side of the retainer. The channel may be configured to receive a second portion of the elongated body. An anchor pad may be secured to the bottom side of the retainer and configured to secure the anchor pad to the skin of a patient. The channel may have a lateral width less than a lateral width of the recess.

Another aspect is a securement system comprising a medical article having an elongated body and a stabilization device. The device includes a retainer and an anchor pad. The retainer includes a recess and a flap with the flap being movable from an open position to a closed position. At least a portion of the body is disposed in the recess and below the flap to secure the body to the retainer at least when the flap is in the closed position.

Another aspect is a securement system comprising a medical article having an elongated body and a stabilization device. The device includes a retainer and an anchor pad. The retainer includes a recess and a dressing with the dressing being movable from an open position to a closed position. At least a portion of the body is disposed in the recess and below the dressing to secure the body to the retainer at least when the dressing is in the closed position.

Another aspect is a securement system comprising a medical article having an elongated body and a stabilization device. The device includes a retainer and an anchor pad. The retainer includes a recess for receiving at least a portion of the medical article. A first portion of the anchor pad is movable from an open position to a closed position with the first portion adhering to a second portion of the anchor pad when in the closed position.

Another aspect is a securement system comprising a medical article having an elongated body and a stabilization device. The device includes a retainer and an anchor pad. The retainer is supported by the anchor pad and configured to receive the medical article. The system further includes a dressing connected to the anchor pad and being configured to cover an insertion site. The dressing has a lower surface at least partially covered by an adhesive for contacting the patient's skin and a slot configured to allow the medical article to pass between at least a portion of the anchor pad and the dressing during application of the dressing to the patient's skin.

Another aspect is a securement system comprising a medical article having an elongated body and a stabilization device. The stabilization device may have a retainer and an anchor pad. The retainer may have a proximal side, a distal side, and an upper side. The retainer may include at least one adhesive surface. In some aspects, the upper side of the retainer includes at least one adhesive surface. The retainer may have a recess and a channel formed within the retainer. The channel may extend from the recess to the proximal side of the retainer. At least a portion of the elongated body may be disposed within the recess and the channel. At least a portion of the elongated body may contact the at least one adhesive surface of the retainer.

Another aspect is a securement system also has a dressing having a pad layer and a transparent film layer. The pad may have a first window so that the body of the medical article is visible through the first window when the dressing is placed over the stabilization device. The pad may include a second window so that the insertion site of the medical article is visible through the second window when the dressing is placed over the stabilization device. In some aspects, the recess includes at least one abutment configured to contact a proximal facing surface of the elongated body to prevent the body from moving in at least the proximal direction.

Another aspect is a securement device configured to secure a medical article having an elongated body to a patient that may comprise an anchor pad and a retainer supported by the anchor pad. The retainer may comprise a recess configured to receive at least a portion of the elongated body. A dressing may be coupled to the anchor pad. The dressing may be configured to be movable from an open position to a closed position to secure the elongated body to the retainer and to cover an insertion site at least when the dressing is in the closed position.

Another aspect is a securement device configured to secure a medical article having an elongated body to a patient that may comprise an anchor pad and a retainer supported by the anchor pad. The retainer may comprise a recess configured to receive at least a portion of the elongated body. A flap may be coupled to the anchor pad. The flap may be configured to be movable from an open position to a closed position. The flap may include at least one adhesive surface configured to secure the flap to at least the elongated body when the flap is in the closed position.

Another aspect is a securement device configured to secure a medical article having an elongated body to a patient that may comprise an anchor pad having a first portion and a second portion. The first portion of the anchor pad may be configured to be movable from an open position to a closed position and may be configured to adhere to the second portion of the anchor pad when the first portion of the anchor pad in the closed position. A retainer may be supported by the second portion of the anchor pad. The retainer may comprise a recess configured to receive at least a portion of the medical article.

Another aspect is a securement device configured to secure a medical article having an elongated body to a patient that may comprise an anchor pad and a retainer supported by the anchor pad. The retainer may be configured to receive at least a portion of the medical article. A dressing may be connected to the anchor pad. The dressing may be configured to cover an insertion site. The dressing may have a lower surface at least partially covered by an adhesive for adhering the dressing to the skin of a patient. The dressing may have a slot configured to allow the medical article to pass between at least a portion of the anchor pad and the dressing during application of the dressing and the anchor pad to the skin of the patient.

Another aspect is a securement device configured to secure a medical article having an elongated body to a patient that may comprise an anchor pad and a retainer supported by the anchor pad. The retainer may be configured to receive at least a portion of the medical article. A support member may be coupled to the anchor pad, the support member configured to support a portion of the medical article extending distally of a recess in the retainer. The support member may include a passage for releasably locking the support member to the medical article. The support member may be formed in the shape of a prism. The support member may be coupled to the retainer along a fold line. The fold line may be perforated to facilitate separation of the support member from the retainer.

BRIEF DESCRIPTION OF THE DRAWINGS

These and other features, aspects, and advantages of the invention disclosed herein are described below with reference to the drawings of certain embodiments, which are intended to illustrate and not to limit the invention. Additionally, from figure to figure, the same reference numerals have been used to designate the same components of an illustrated embodiment. The following is a brief description of each of the drawings.

FIGS. 54-55 are perspective views of a securement device according to another embodiment of the present invention.

DETAILED DESCRIPTION OF CERTAIN EMBODIMENTS

Figure 1:
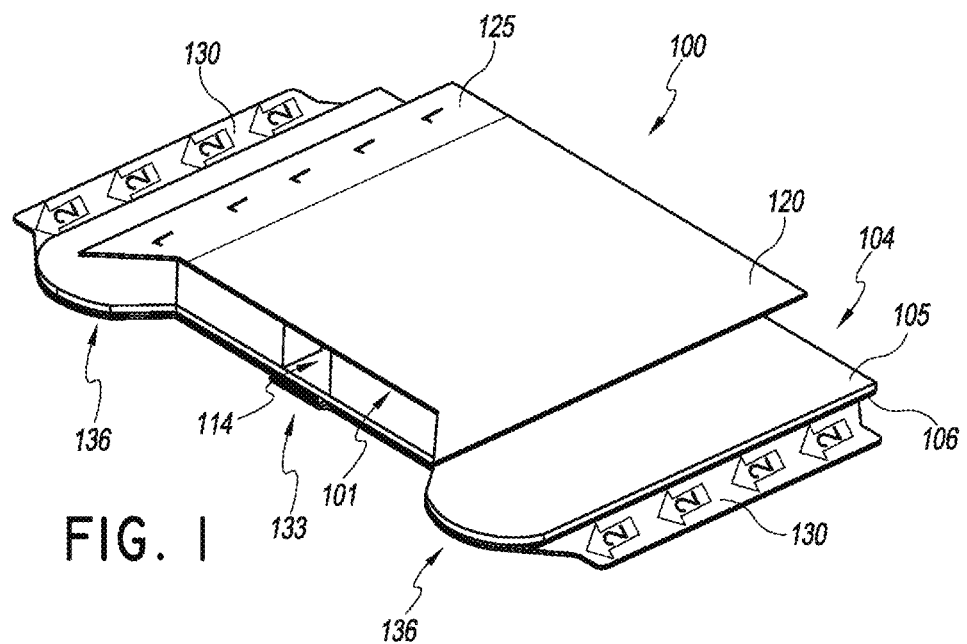
FIGS. 1-2 are perspective views of a securement device according to an embodiment of the present invention.

The following description and examples illustrate preferred embodiments of the present securement device disclosed in the context of use with exemplary catheters. More specifically, the embodiments relate to a stabilization device and related techniques that stabilize a medical article in position on a patient. The embodiments of the securement device are illustrated with a catheter in use as part of a peripheral intravenous ("I.V.") line.

The following description and the accompanying figures, which describe and show the preferred embodiments, are made to demonstrate several possible configurations that a securement device and/or system can take to include various disclosed aspects and features. The illustrated embodiments are shown in use with a catheter having a spin nut. The illustration of the securement device in this context is not intended to limit the disclosed aspects and features to the specified embodiment or to usage only with the illustrated catheter. For example, the disclosed embodiments can be used with a connector fitting. The connector fitting may include a spin nut or other outwardly extending feature. Those of skill in the art will recognize that the disclosed aspects and features are not limited to any particular embodiment of a securement system, and securement systems, which include one or more of the inventive aspects and features herein described, can be designed for use with a variety of medical articles.

It will be understood by those of skill in the art in view of the present disclosure that the securement device described can be used with other types of medical articles, including, but not limited to catheters and catheter hubs of various design, either with or without connectors or extension sets, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes; any other sort of fluid supply or medical lines, connector fittings, and scopes, as well as electrical wires or cables connected to external or implanted electronic devices or sensors. The medical articles can be a single medical article or a combination of medical articles.

The securement device described herein is especially adapted to arrest at least transverse movement of a catheter. The securement device holds medical articles against the patient and protects an area in proximity to an insertion site. The securement device accomplishes this without meaningfully impairing (i.e., substantially occluding) fluid flow through a lumen of the medical article or impairing insertion of the medical article. In some embodiments, retention mechanisms to accomplish this include a retainer having a recess, flap, straps, anchor pads, and/or dressings. For example, the recess, flap, straps, anchor pads, and or dressings may be coated with an adhesive. The flap or strap may be integral to the securement device and fold over and secure a medical article placed in the retainer. In other embodiments, the securement device may include an integrated dressing or portion of the anchor pad configured to cover the insertion site. The integrated dressing/anchor pad may fold over another portion of the anchor pad/retainer so that the medical article is disposed therebetween.

In general, the securement may be attached to a patient and a medical article may be placed at least partially within the securement. The securement may include a recess. The recess may be formed by one or more upwardly extending walls. The upwardly extending walls may be shaped to include one or more abutment surfaces. The abutment surfaces may inhibit and/or prevent movement of a medical article placed in the securement in at least one direction. The upwardly extending walls may include an adhesive on one or more surfaces. In some embodiments, at least a portion of the top surfaces of the upwardly extending walls forming the recess are coated with an adhesive. A dressing may be configured to cover an insertion site, the securement device, and at least a portion of the medical article. The medical article may be disposed between the securement and the dressing. In some embodiments, the dressing may be integral with the securement.

To assist in the description of these components of the securement system, the following coordinate terms are used (see, e.g., FIGS. 7, 25, 27, 46, 56, and 71). A "longitudinal axis" is generally parallel to a portion of the catheter hub or other medical article retained by the securement system, as well as parallel to the axis of the recess of the retainer, through which the medical article extends. A "lateral axis" is normal to the longitudinal axis. A "transverse axis" extends normal to both the longitudinal and lateral axes.

In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel, recess, or hub, and therefore is substantially synonymous with the term "longitudinal" as used herein. Also, the terms "proximal" and "distal," which are used to describe the present securement system, are used consistently with the description of the exemplary applications (i.e., the illustrative examples of the use applications). Thus, proximal and distal are used in reference to the center of the patient's body.

The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the recess in the retainer. The term "underside" is used to describe the portion of the retainer that is located below a lateral axis that passes through the axis of the recess in the retainer. Brief introductions to some of the features, which are common to the described embodiments of the securement systems, are now described.

Various aspects will now be described with reference to specific forms or embodiments selected for purposes of illustration. It will be appreciated that the spirit and scope of the securement system disclosed herein is not limited to the selected forms. Moreover, it is to be noted that the figures provided herein are not drawn to any particular proportion or scale, and that many variations can be made to the illustrated embodiments. Brief introductions to some of the features, which are common to the described embodiments of the securement systems, are now described.

The preferred embodiments advantageously provide a medical line securement system for securing a medical article to a patient. The medical article may have an elongated body. The elongated body cooperates with a retainer to arrest movement of the medical article in longitudinal, lateral, and transverse directions when placed within the retainer. The retainer may include a recess. The recess may be sized and shaped to receive a portion of a medical article, for example, a spin nut. The recess may provide one or more abutment surfaces that can limit movement in the longitudinal and/or lateral direction. In some embodiments, the bottom surface of the recess includes an adhesive. The adhesive can limit the longitudinal, lateral, and transverse movement of a medical article placed within the recess of the retainer. The retainer may be supported by one or more anchor pads. The anchor pads may include an adhesive to attach the anchor pads to the skin of a patient. A flap/strap coupled to the anchor pad and/or retainer may be folded over the retainer further securing a medical article placed in the retainer.

The medical article may include a cannula. The cannula may be inserted into a patient. This insertion site may be further covered by a dressing. The dressing may further limit the movement of the medical article. The dressing may also protect the insertion site from moisture and/or infection. In some embodiments, the dressing is integrated or coupled to the retainer and/or anchor pad. In some embodiments, the securement systems disclosed herein can be attached to a patient after a medical line, for example a peripheral I.V. line, has been introduced to the patient.

To facilitate a complete understanding of the embodiments, the remainder of the detailed description describes the securement systems with reference to the figures, wherein like elements among the embodiments are referenced with like numerals throughout the following description.

Figure 2:
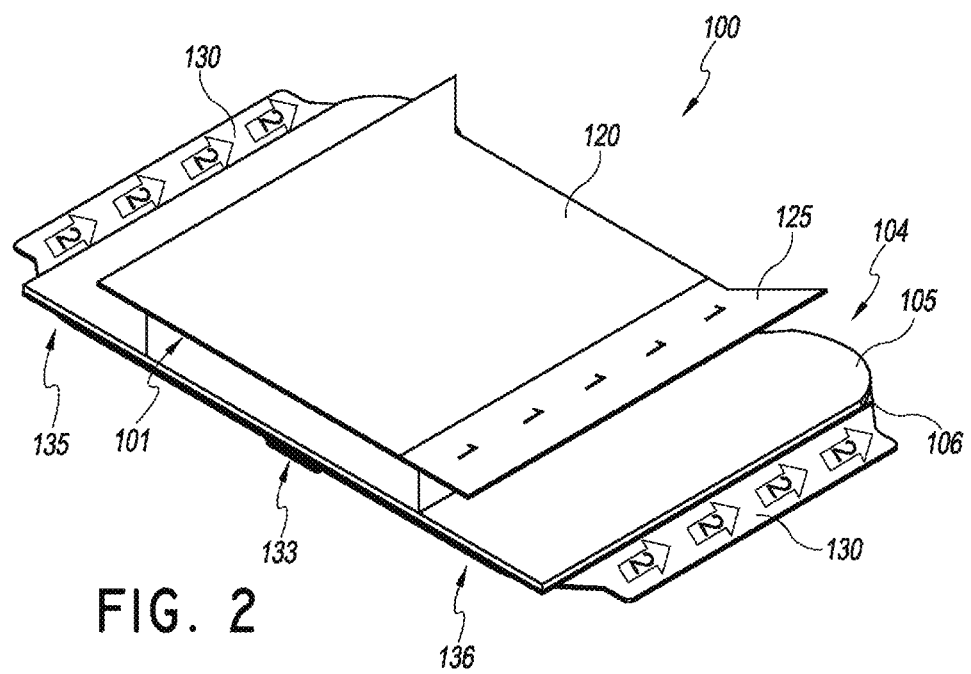

With reference now to FIGS. 1-2 an embodiment of a securement device 100 includes an anchor pad 104 and a retainer 101. The anchor pad 104 can have a lower (or bottom) surface 106 which may adhere to the skin of a patient and an upper layer 105. The upper layer 105 of the anchor pad 104 is configured to support at least the retainer 101. In combination, the lower surface 106, upper layer 105, and possibly one or more intermediate layers may comprise a laminate structure. A suitable laminate that comprises a foam or woven material with an adhesive layer is commercially available. The anchor pad 104 may be configured as a flexible structure configured to conform to the surface of a patient's skin. In some embodiments, at least a portion of a lower surface 106 of the anchor pad 104 includes an adhesive.

The upper layer 105 of the anchor pad 104 may comprise a foam (e.g., closed-cell polyethylene foam) or woven material (e.g., tricot) layer or non-woven material. A surface of the foam or woven material layer constitutes the upper layer of the anchor pad 104. In the alternative, the upper layer 105 may comprise an upper paper or other nonwoven cloth layer, and an inner foam layer may be placed between the upper layer and a lower adhesive surface. In some embodiments, the anchor pad includes an anti-microbial additive. The anchor pad and retainer may protect a patient's skin from irritation caused by the medical device rubbing against the skin.

The anchor pad 104 is configured to be secured to a patient's skin. The adhesive on the lower surface 106 of the anchor pad 104 may be a medical-grade adhesive and can be either diaphoretic or nondiaphoretic, depending upon the particular application. The lower adhesive surface may have additional types of medical adhesives laminated thereto such as a silicone adhesive. In some embodiments, the lower adhesive layer comprises an anti-bacterial or anti-microbial material. For example, the lower adhesive layer may comprise one or more oligodynamic metal salts or oxides, or a combination of salts and oxides. In some embodiments, the lower adhesive layer comprises a silver material, for example a silver salt, colloid, or complex. The adhesive surface may be a solid layer or may be configured as an intermittent layer such as in a pattern of spots or strips. The lower adhesive surface can be applied to the anchor pad 104 during manufacture, and may be further covered with a liner as described below. Alternatively, it is possible to apply a double-sided adhesive tape to the upper layer before application.

In the embodiment shown in FIG. 1, the anchor pad 104 includes two removable liners 135 and 136 on a lower surface 106 of the anchor pad 104. The removable liners 135 and 136 may cover the lower adhesive surface before use. The liners may resist tearing and be divided into a plurality of pieces to assist removal of the liners and ease attachment of the anchor pad 104 to a patient's skin. The liners 135 and 136 may be divided into two adjacent pieces. The liners 135 and 136 may be made of a paper, plastic, polyester, or similar material. For example, the liners 135 and 136 may comprise a material made of polycoated, siliconized paper, or another suitable material such as high density polyethylene, polypropylene, polyolefin, or silicon coated paper.

As illustrated in FIGS. 1-2, the release liners 135 and 136 include tabs 130 that extend beyond the edge of the anchor pad 104 to allow a medical provider to easily grip the release liners 135 and 136 and remove them from the anchor pad 104. The tabs 130 may be located at any edge of the anchor pad 104 and may be any suitable size or shape. As shown in FIGS. 1-2 a portion of the release liner 136 may extend over a portion of the release liner 135 at an interface 133 between the release liners 135 and 136.

Continuing with FIGS. 1-2, a liner 120 may cover an adhesive surface of the retainer 101. The adhesive surface can be configured to adhere to portions of a dressing and/or portions of the medical article. The liner may cover the entire top surface of the retainer 101 or may only cover the adhesive portions of the retainer 101. As illustrated in FIG. 1, the liner 120 is sized to cover the entire retainer 101 and to also extend beyond the outer perimeter of the retainer 101. In this way, a portion of the liner 120 can form a pull tab 125. The pull tab 125 can allow the healthcare provider to easily grip the liner 120 and remove the liner 120 from the retainer 101. The liner 120 may be prepared such that the liner 120 maintains the covered surface of the retainer 101 in a sterilized state. In some embodiments, the liner 120 has a longer dimension than the retainer 101 which insures the liner 120 is always cantilevered beyond the top edge of retainer 101 to create a griping surface for the user to remove the liner 120.

Figure 3:
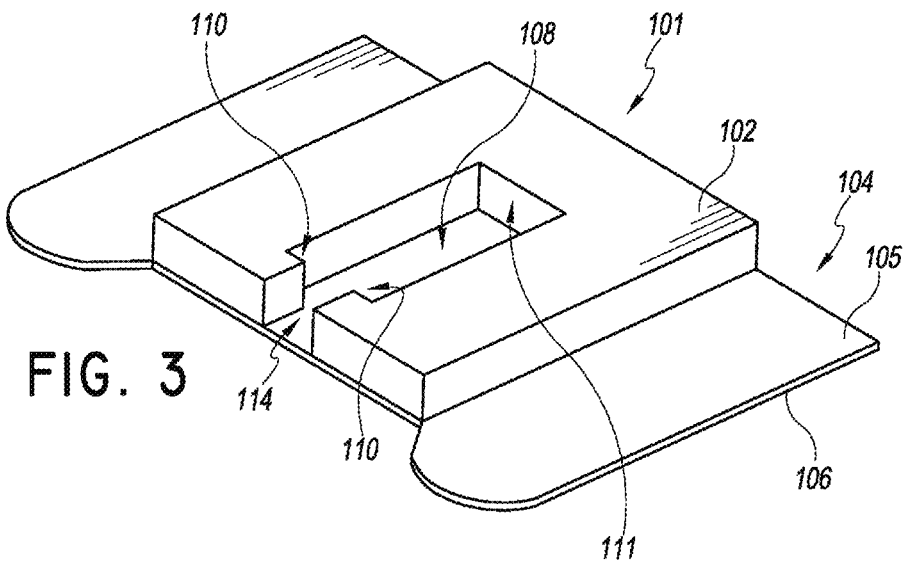
FIGS. 3-4 are perspective views of the securement device of FIG. 1 with the liners removed.
Figure 4:
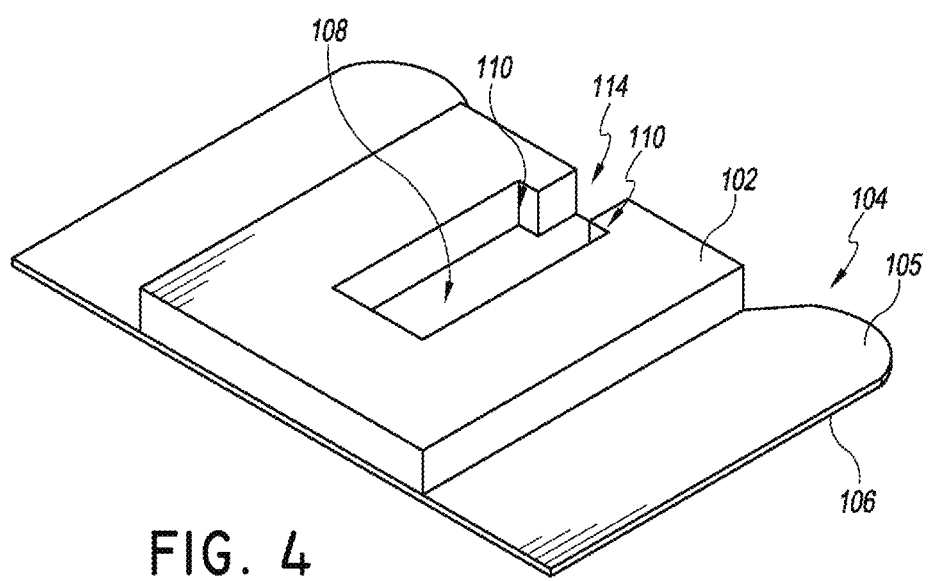

Turning to FIGS. 3-4, the retainer 101 is configured to receive and secure at least a portion of a medical article. In the illustrated embodiment of FIGS. 3-4, the retainer 101 includes a top (or upper) surface 102 and a recess 108 shaped to receive at least a portion of a medical article. As shown, the top/upper surface 102 can be flat, and the recess 108 can extend from the top surface 102 to a bottom surface of the retainer 101. The recess 108 also includes a channel 114 extending through the proximal side of the retainer 101. The channel 114 may be shaped to receive at least a portion of the medical article. As shown, the channel may have a lateral width that is less than the lateral width of the recess. The retainer 101 may also include proximal abutments 110 which extend at least partially in a direction towards the channel 114. The proximal abutments 110 may be shaped to contact at least a portion of the medical article and prevent movement of the medical article placed within the recess and/or channel in at least the proximal direction. In some embodiments, the proximal abutments are disposed between the recess 108 and the channel 114.

The recess may also include a distal abutment 111. The distal abutment 111 may be formed by one or more walls extending upward from the top surface of the anchor pad 104. The distal abutment 111 may be shaped to contact at least a portion of the medical article and prevent movement of the medical article placed within the recess 108 and/or channel in at least the distal direction.

The recess 108, channel 114, proximal abutments 110, and/or distal abutments 111 may be sized and shaped to fit any appropriate medical article or portion thereof. In some embodiments, the recess 108, channel 114, proximal abutments 110, and/or distal abutments 111 are sized and shaped to accept more than one type and/or more than one sized portion of a medical article. In this way, the securement system disclosed herein can be used with multiple medical articles. Multiple varieties of spin nuts are used in the medical industry and may vary depending on application, geographic location, and/or supplier. Such spin nuts vary in size, shape, and/or dimension. Thus, the securement systems disclosed herein can advantageously provide a retainer configured to secure more than one spin nut embodiment. For example, the recess 108, channel 114, proximal abutments 110, and/or distal abutments 111 may be sized and shaped such that when a first spin nut is inserted within the recess 108, a proximal facing surface of the first spin nut is placed into contact with a distal facing surface of the proximal abutment while a distal facing surface of the first spin nut does not contact a proximal facing surface of the distal abutment. When a second, differently sized and/or shaped spin nut is inserted within the same recess 108, a proximal facing surface of the second spin nut is placed into contact with a distal facing surface of the proximal abutment while a distal facing surface of the second spin nut is also placed into contact with a proximal facing surface of a distal abutment. In this way, one or more surfaces of the spin nut may abut against one or more abutment surfaces of the retainer 101 depending on the size and/or shape of the spin nut that is being secured. Accordingly, depending on, for example, the length of the channel and the length of the spin nut, a gap or space may exist in front of or behind a spin nut when the spin nut is inserted into the retainer 101. In some embodiments, the recess 108 and channel 114 are sized and shaped to approximately equal the size and shape of a particular spin nut such that the spin nut snugly fits within the recess 108 and channel 114.

In some embodiments, at least a portion of an interior surface of the recess 108 and/or channel 114 includes an adhesive. For example, an adhesive may be disposed on at least a portion of the lower surface of the recess 108 and/or channel 114 and/or on at least a portion of the interior walls that form the recess 108 and/or channel 114. Other surfaces of the retainer 101 may also include an adhesive. For example, in some embodiments, at least a portion of the top surfaces 102 of the upwardly extending walls that form the recess 108 include an adhesive. The adhesive may be similar to the adhesives described in connection with the anchor pad 104. The adhesive can adhere to one or more surfaces of a medical article placed within the retainer 101 so as to further limit movement of the medical article. The retainer 101 may comprise various materials, for example, one or more elastomers. In some embodiments, the retainer 101 comprises a material configured to allow for easy removal of occlusive wrapping and/or bandages.

Figure 5:
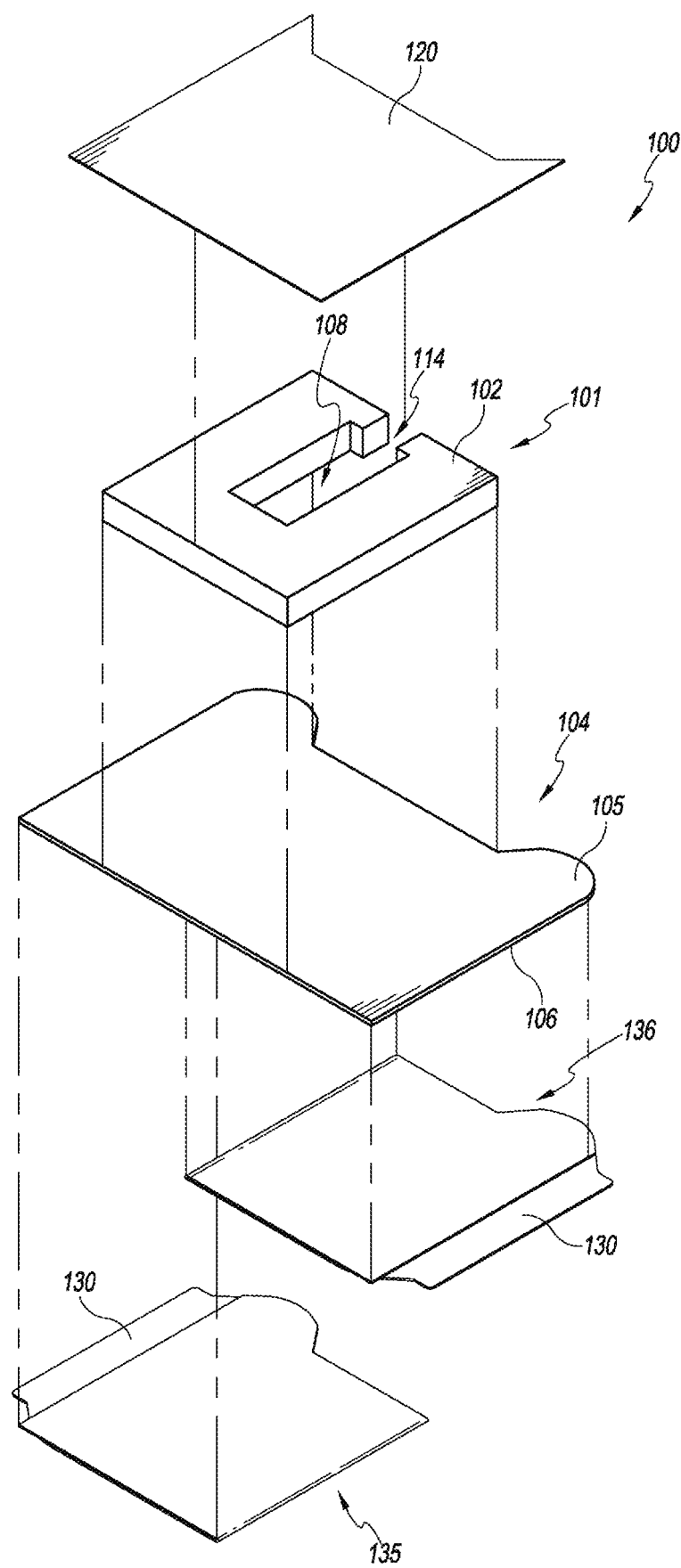
FIG. 5 is an exploded view of the securement device of FIG. 2.

FIG. 5 is an exploded view of the securement device of FIG. 1. The liner 120 may be disposed on an upper surface 102 of the retainer 101. The upper surface 102 of the retainer 101 may include an adhesive. The adhesive may be configured to arrest movement of a medical article that is placed into contact with the upper surface 102 of the retainer 101. In some embodiments, the upper surface 102 of the retainer 101 includes an adhesive such that the medical device may be stabilized on the retainer 101 allowing a user to let go of the medical device and use their hand to complete the installation. The retainer 101 and liner 120 may be disposed on the anchor pad 104. At least a portion of the bottom surface 106 of the anchor pad 104 may include an adhesive. Removable liners 135 and 136 may be disposed on the bottom surface 106 of the anchor pad 104 to cover the adhesive surface. The liners 135 and 136 may be removed and the anchor pad 104 may be secured to the skin of a patient.

Figure 6:
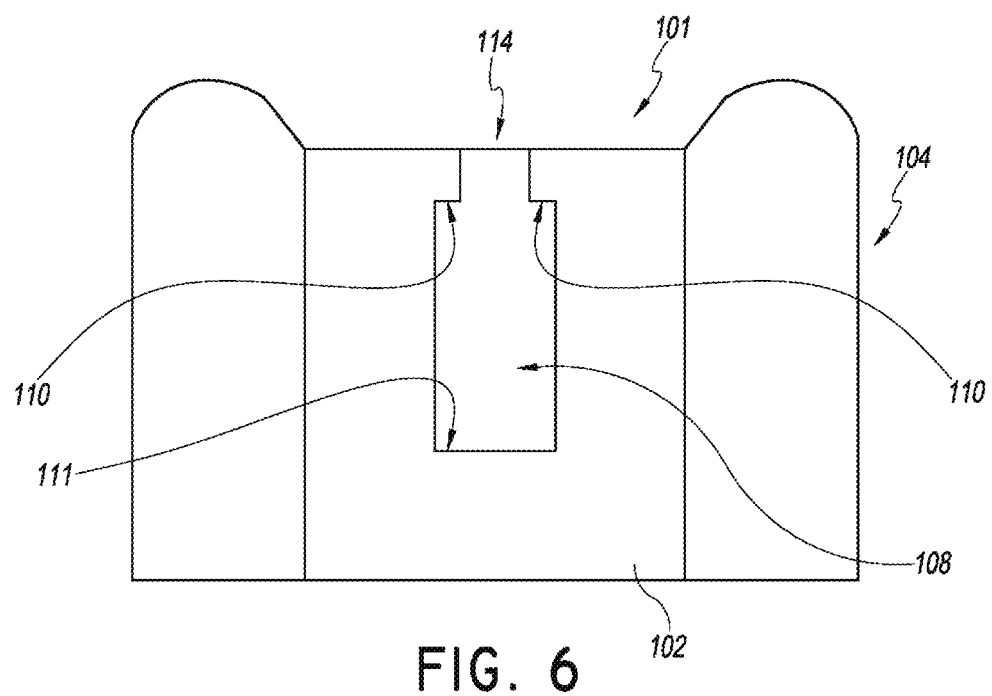
FIG. 6 is a plan view of the securement device of FIG. 1 with the liners removed.

Turning to FIG. 6, a plan view of the retainer 101 and anchor pad 104 is shown. The retainer 101 includes a recess 108, a channel 114, proximal abutments 110, and distal abutment 111. The recess 108 may be any suitable size and shape. As shown the recess 108 has a width that is larger than the width of the channel 114 extending in the proximal direction from the recess 108. The difference in widths can form abutments 110. In other words, abutments 110 can extend into a proximal portion of the recess 108 to form a channel 114 that is narrower in width than the recess 108. In this way, the retainer 101 may receive at least a portion of a medical article in at least a portion of the channel 114 and/or in at least a portion of the recess 108. In addition, at least a portion of a proximal facing surface of the medical article may abut against a distal facing surface of the abutments 110. In this way, the abutments 110 can prevent movement, at least in the proximal direction, of a medical article placed within the retainer 101 while distal abutment 111 may prevent movement at least in the distal direction. In some embodiments, the width of the recess 108 is about 7 mm while the width of the channel 114 is about 4 mm.

Figure 7:
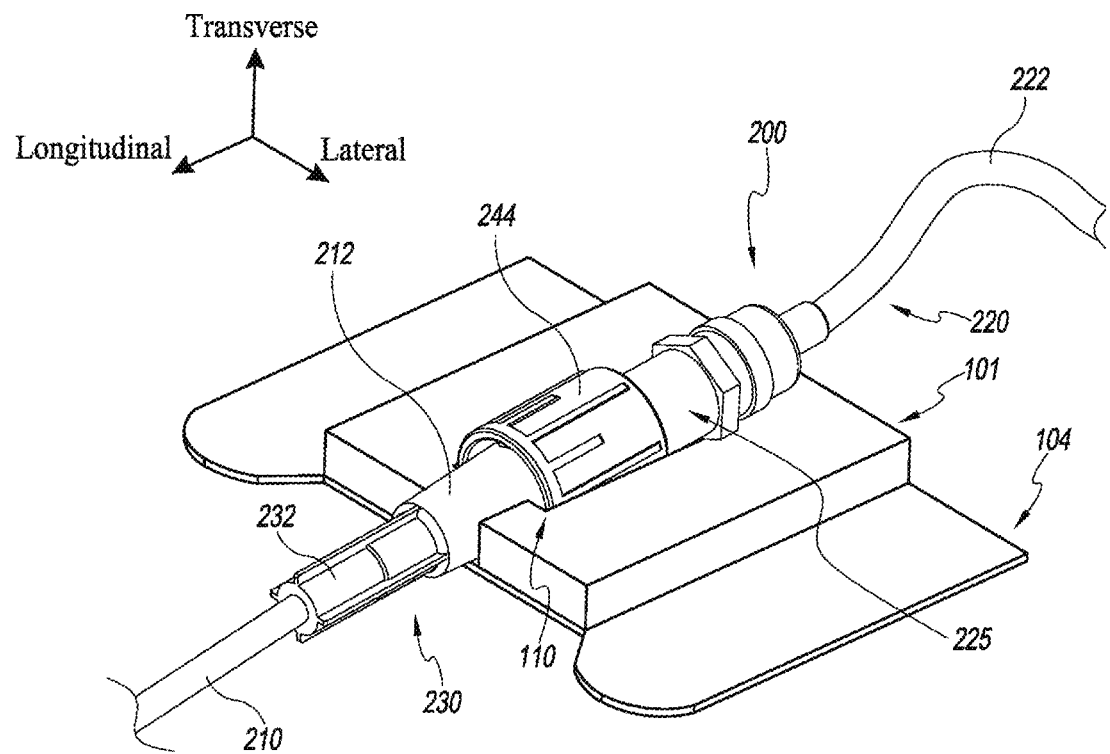
FIG. 7 is a perspective view of the securement device of FIG. 3 with the liners removed and a medical article placed in the retainer.

As shown in FIG. 7, a medical article 200 may be placed within the retainer 101. The medical article can include a catheter 210 and a catheter hub 230 connected to an extension set 220. Catheter hubs are generally known to those skilled in the art. The catheter hub 230 shown in FIG. 7 has a proximal body 232 and a distal body 212. However, different catheter hubs may include more or less bodily sections having various different shapes and sizes, all of which may be used with the retainer or other embodiments of the retainer described herein. The extension set 220 illustrated in FIG. 7 includes a proximal portion, such as a spin nut 244 connected to a distal portion, such as connector 225 that is coupled to a medical tube 222. In certain embodiments, the catheter hub 230 comprises an integral one-way valve. In some embodiments, the retainer 101 is configured to suspend the medical article 200 above the skin of a patient to allow for a catheter to be inserted into a patient's skin at an angle relative to the skin of the patient, for example, at an angle of 7 degrees. For example, as shown in FIG. 7, the retainer 101 may be sized and shaped such that a back portion of a medical article is supported by a distal portion of the retainer 101. In some embodiments, the distal abutment 111 may both suspend a distal portion of the medical article relative to a proximal portion of the medical article and prevent movement of the medical article in at least the distal direction by abutting against a distal facing surface of the medical article.

In the embodiment shown in FIG. 7, the recess 108 is shaped to receive a portion of the spin nut 244 and the channel 114 is shaped to receive a portion of the distal body 212 of the catheter hub 230. In this way, the proximal surface of the spin nut 244 can abut against a distal surface of the abutments 110. In other words, a proximal surface of the spin nut 244 may abut against a distal surface of the retainer 101 so as to prevent movement of the catheter 200 in the proximal direction towards the patient.

The recess 108 and/or channel 114 may be shaped to receive different portions of the medical article 200. For example, in some embodiments, the channel 114 and recess 108 are shaped to receive the connector 225. In this embodiment, the distal surface of the abutments 110 may contact a proximal facing surface of the connector 225 to prevent movement of the catheter 200 in the proximal direction. In this way, the spin nut 244 is not secured by the retainer 101 and thus, the spin nut 244 can be rotated to release the extension set 220 from the catheter hub 230 while the catheter hub 230 remains secured to the patient.

Figure 8:
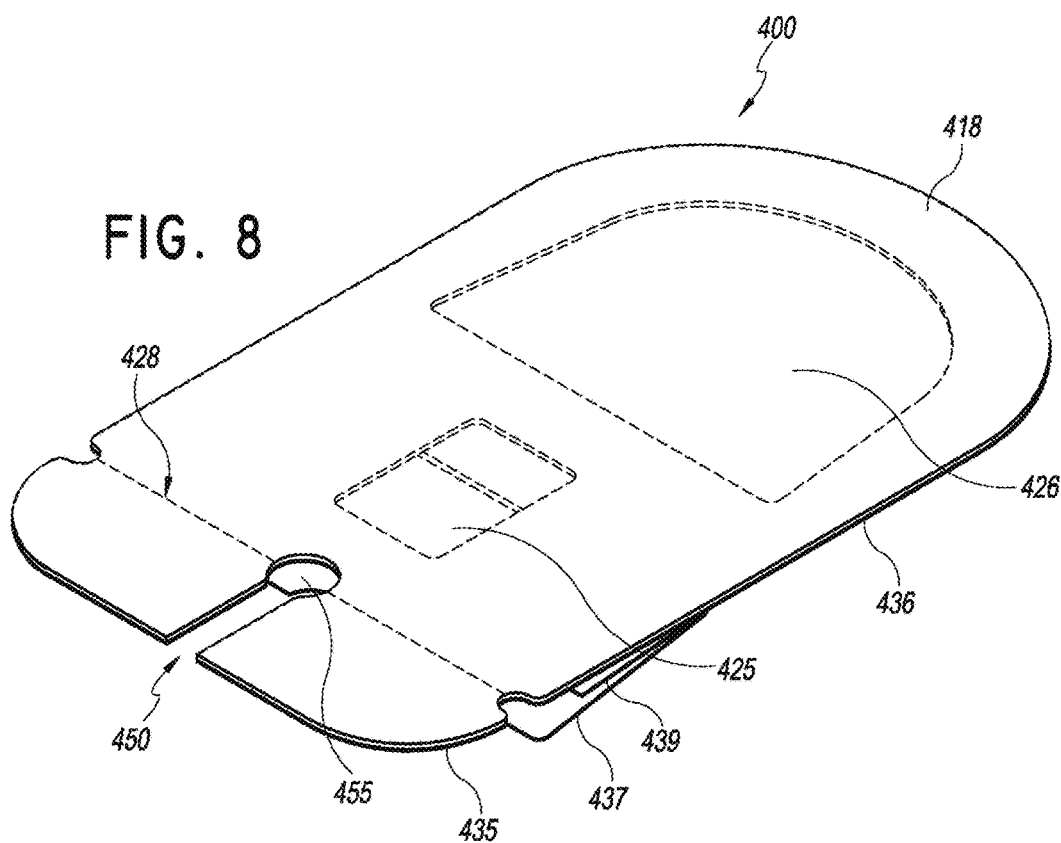
FIGS. 8-9 are perspective views of a dressing that may be used in combination with the securement device of FIG. 1.
Figure 9:
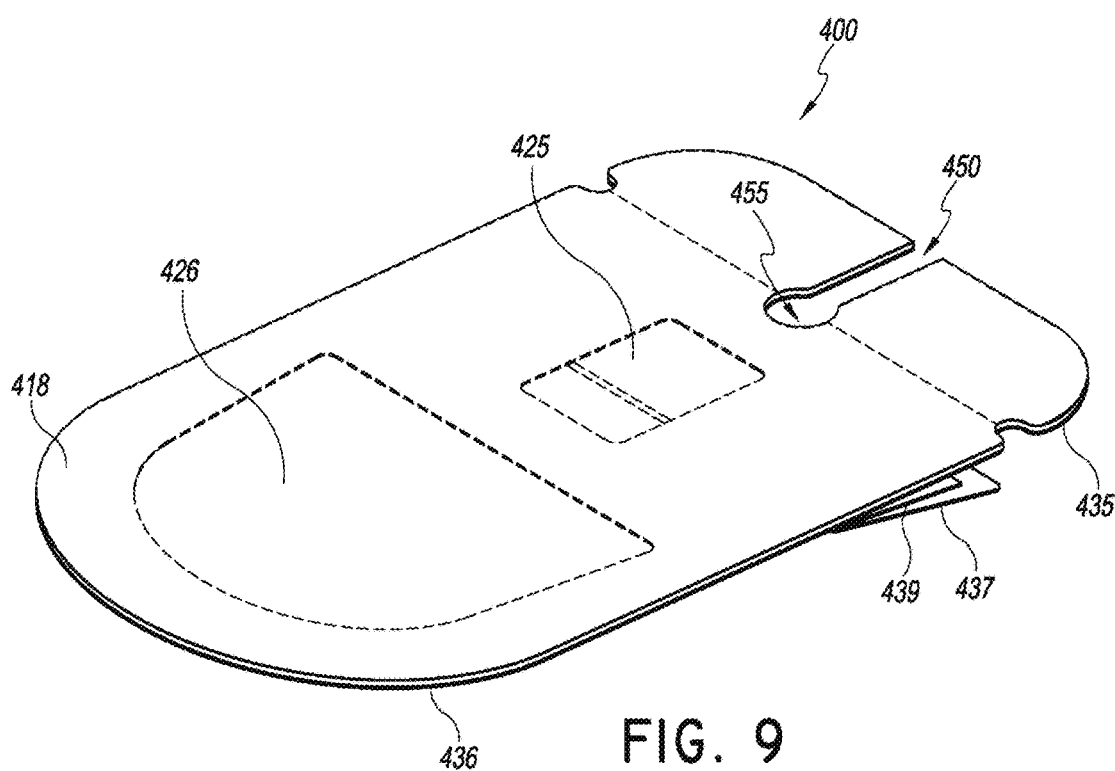

Turning to FIGS. 8-9, a dressing 400 that may be used with the securement device described above is shown. The dressing 400 comprises an occlusive layer 418, a lower surface that is at least partially covered by an adhesive and two release liners 435 and 436 covering the lower surface of the dressing 400. The adhesive is configured to adhere to the skin of a patient and/or to portions of the anchor pads, retainer, and/or medical article. The dressing 400 includes an insertion window 426 and a retainer window 425. The dressing also includes a channel 450 and an opening 455 shaped to receive the medical tubing 222. As illustrated, the release liners 435 and 436 project out from the lower surface of the dressing and form pull tabs 437 and 439.

The release liners 435 and 436 may cover adhesive disposed on the lower surface of the dressing 400. The release liners 435 and 436 may cover the entire lower surface of the dressing or may only cover the adhesive surfaces. The release liners 435 and 436 may include an anti-microbial or anti-bacterial material or coating, and/or have silver particles dispersed throughout. The dressing 400 and release liners 435 and 436 may be prepared such that the release liners 435 and 436 maintain a covered surface of the occlusive layer in a sterilized state. In some embodiments, only one release liner is used.

In some embodiments, the adhesive is included on a bottom surface of the dressing 400 at least around the perimeter of the insertion window 426 and around the perimeter of the retainer window 425. In some embodiments, the adhesive covers the entire bottom surface of the dressing 400 except for the areas formed by the insertion window 426 and the retainer window 425. In some embodiments, the adhesive on the bottom surface of the dressing 400 is disposed such that the dressing 400 will not adhere at the point of insertion. In this way, the likelihood of aggravating or excoriating the insertion site or skin around the insertion site and/or introducing contaminants and/or liquid near or into the point of insertion may be reduced. In addition, the adhesive on the bottom surface of the dressing 400 may be disposed such that the adhesive layer will not adhere or stick to the catheter and/or the catheter hub. In this way, sticky residues and buildup on the catheter and catheter hub may be reduced or avoided. In other embodiments, the adhesive covers the entire bottom surface of the dressing 400 including the insertion window 426 and the retainer window 425.

As described above, the dressing 400 comprises a channel 450 and an opening 455. The channel 450 and opening 455 allow for the dressing to be applied over a medical article. The dressing 400 may be configured to provide a waterproof seal around an insertion site when applied to the skin of a patient over a catheter and/or catheter hub. In some embodiments, the dressing 400 is still breathable while the waterproof seal is created. In some embodiments, the dressing 400 is configured similar to the anchor pad 104.

In some embodiments, the dressing 400 comprises a hemostatic dressing. In such embodiments, securing the dressing 400 over an insertion site or other wound may inhibit blood from flowing from the site. For example, the dressing 400 may comprise or be coated with a hemostatic or antihemorrhagic agent such as chitosan or other polysaccharide, a collagen like microfibrillar hemostat, anhydrous aluminum sulfate, potassium alum, titanium dioxide, a gelatin, or a solution of thrombin. In some embodiments, a small thin pad having hemostasis and anti-microbial properties is also provided. Such a pad may be configured to surround the catheter and/or cover the insertion site. In some embodiments, an anti-microbial/hemostasis pad is integral to the retainer 101 or anchor pad 104 to improve ease of placement of the pad. In some embodiments, the pad is made of a material known as HemCon®. In some embodiments, the dressing includes an anti-microbial additive.

Figure 10:
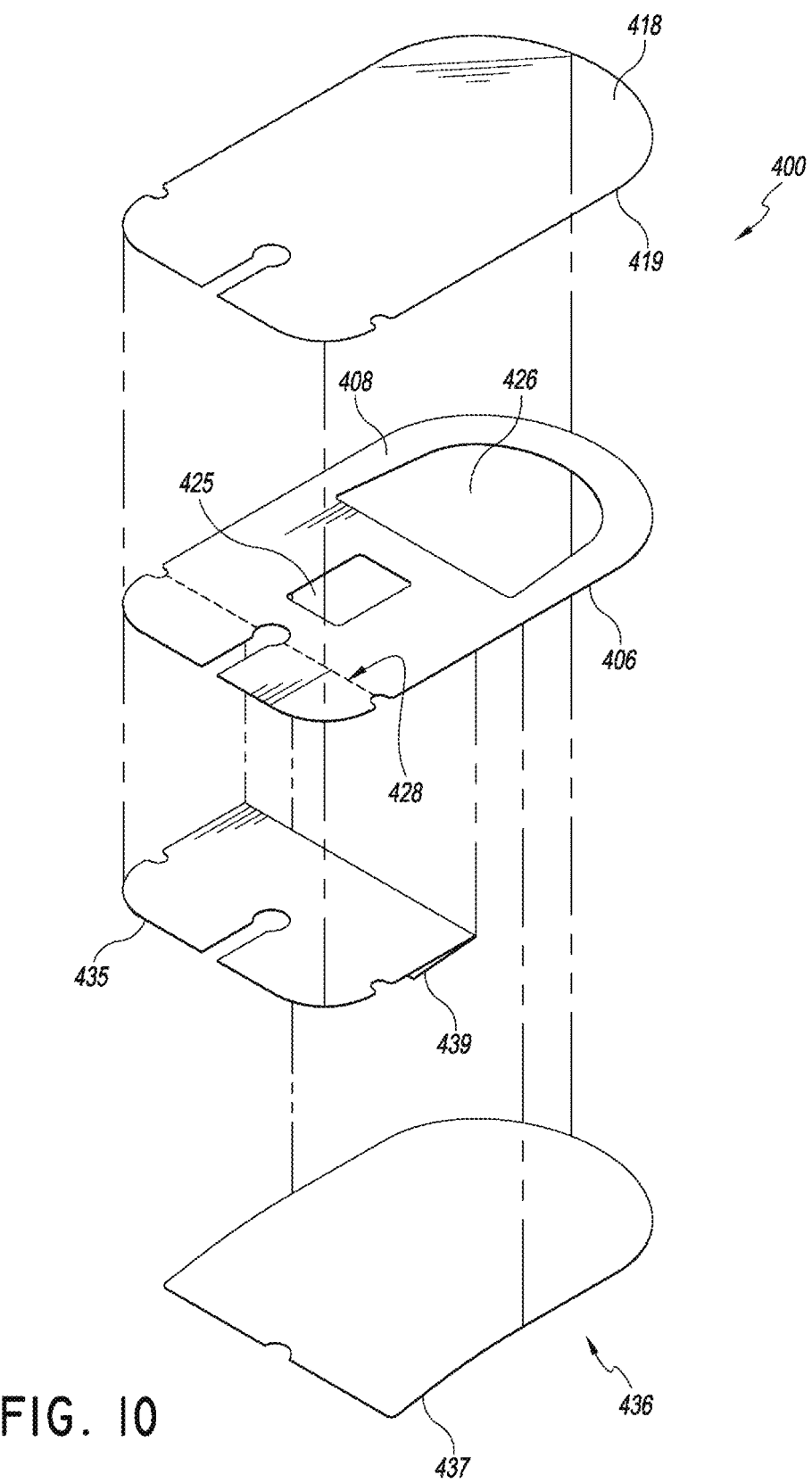
FIG. 10 is an exploded view of the dressing of FIG. 8.

FIG. 10 is an exploded view of the dressing 400. As shown, an occlusive layer 418 may be disposed on the top surface 408 of the dressing 400. The bottom surface 406 of the dressing 400 may be at least partially covered by an adhesive. Release liners 435 and 436 may be disposed on the bottom surface 406 of the dressing 400. As shown, the occlusive layer 418, top surface 408, and release liner 435 of dressing 400, include a channel and an opening. In some embodiments, the bottom surface 419 of the occlusive layer 418 is at least partially covered by an adhesive. In addition, release liner 435 may include a fold over section 439 which contacts a portion 437 of the release liner 436. In this way, a pull tab 439 is covered completely by release liner 436. Thus, a healthcare provider is encouraged to first grip the portion 437 of the release liner 436 to encourage proper placement technique. After front or top of dressing 400 is attached to the skin then the healthcare provider can grip the fold over section 439 to remove release liner 435.

The occlusive layer 418 may be configured to be waterproof or otherwise impermeable to liquids and in some embodiments also restricts the flow of air. In other embodiments, the occlusive layer 418 may be configured to be breathable, allowing air and/or moisture near an insertion site through to the other side of the occlusive layer 418 and away from the insertion site, while keeping at least external moisture on the other side of the occlusive layer 418 away from the insertion site. In some embodiments, the occlusive layer 418 is impermeable to viruses and bacteria, and may comprise or be coated with an anti-bacterial or anti-microbial material. In some embodiments, the occlusive layer 418 comprises or is coated with a waxy material. In some embodiments, the occlusive layer 418 comprises a film which may or may not be transparent.

Selection of a transparent film or semi-transparent film for use as the occlusive layer 418 may allow a medical provider to see the insertion site through the insertion window in the dressing. In this way, potential infections or inflammation may be visualized through the transparent film. A transparent film or semi-transparent film for use as the occlusive layer 418 may also allow a medical provider to see any administered catheter to ensure that a fluid connection is maintained.

In some embodiments, the occlusive layer 418 is absorbent. In some embodiments, the occlusive layer 418 comprises an absorbent acrylic, an alginate, foam, a hydrocolloid, and/or a hydrogel material, and/or may comprise a silver material, for example a silver salt, colloid, or complex. In one embodiment, one or more oligodynamic metal salts or oxides, or a combination of salts and oxides are used in or on the occlusive layer 418 as an antimicrobial agent. In some embodiments, the occlusive layer 418 is configured similar to the upper layer of the anchor pad 104.

Figure 11:
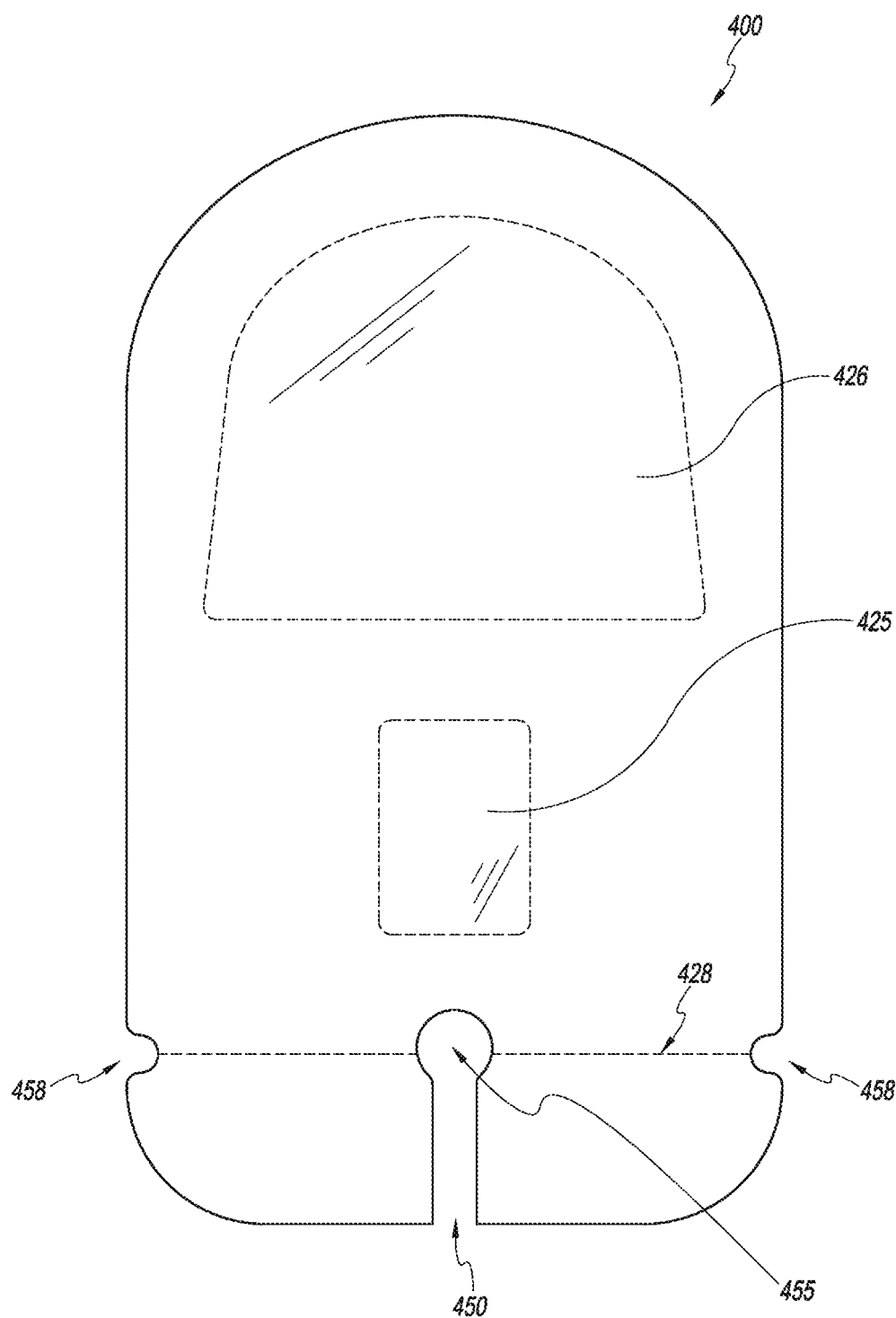
FIG. 11 is a plan view of the dressing of FIG. 8.

In FIG. 11, a plan view of the dressing 400 is shown. As shown, the channel 450 extends from the distal end of the dressing and terminates at opening 455. In certain embodiments, the opening 455 is generally circular in shape and includes a diameter greater than the width of the channel 450. In this way, medical tubing may slide through the channel 450 and rest within the opening 455. Thus, the dressing may be more easily placed over a medical article. The dressing 400 also comprises notches or indentations 458 in the sides of the dressing near the distal end. These notches 458 may locate perforation 428. The perforation 428 may allow for a distal portion of the dressing to be removed easily from the remainder of the dressing.

Figure 12A:
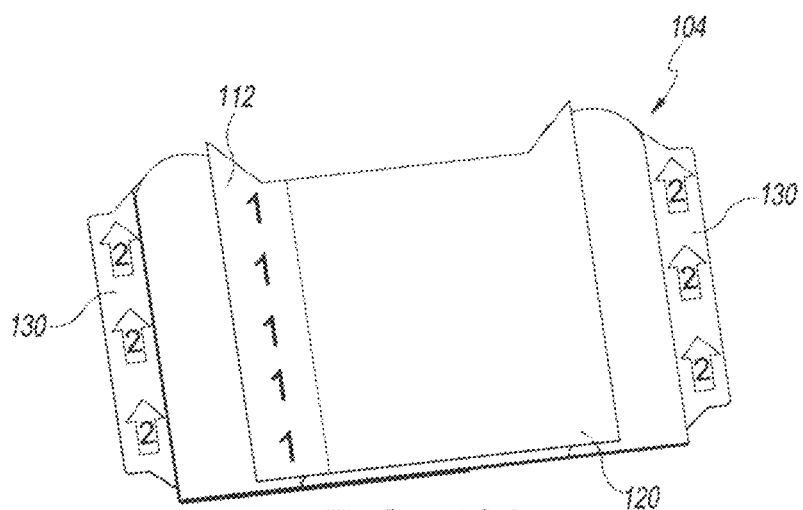
FIGS. 12A and 13-14 are perspective views of a method of using the securement device of FIG. 1. As shown, the method can begin by removing a liner disposed over the retainer.
Figure 13:
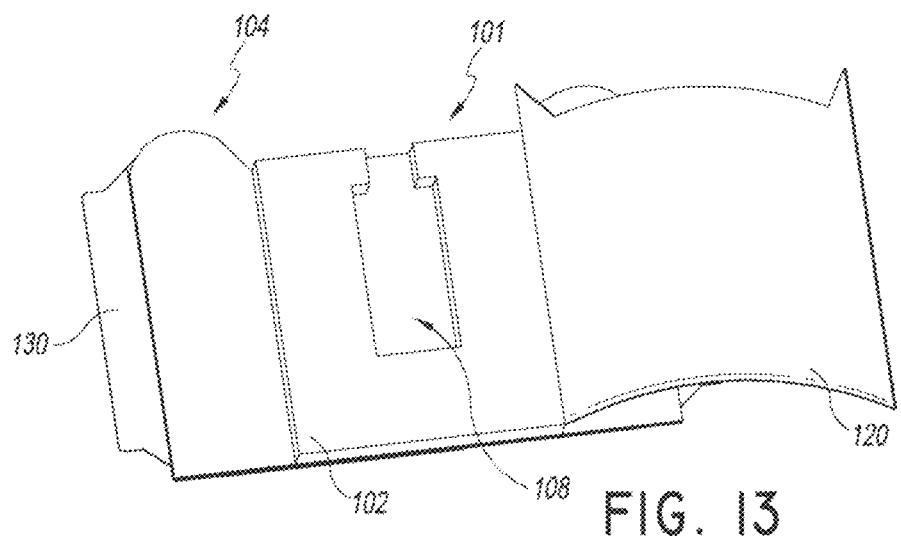
Figure 14:
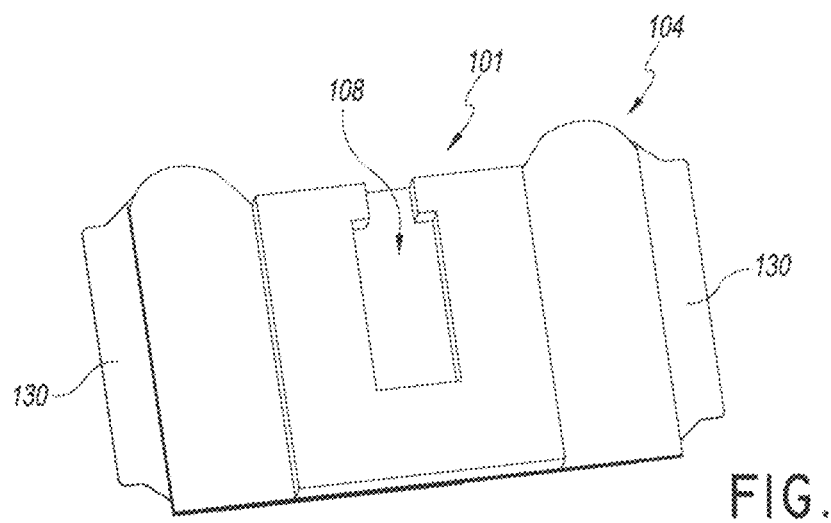

In operation, a method of using the securement device and dressing described above and a process for coupling a medical article to a patient can begin by removing the liner 120 covering the retainer 101 as illustrated in FIGS. 12A and 13-14. The liner 120 may cover one or more adhesive surfaces of the retainer 101. In some embodiments, the entire upper surface 102 of the retainer 101 is coated with an adhesive. As shown, the liners 135 and 136 attached to a surface of the anchor pad 104 may include tabs 130 having one or more arrows that point toward the insertion site such that a medical provider can properly orient the securement device.

Figure 12B:
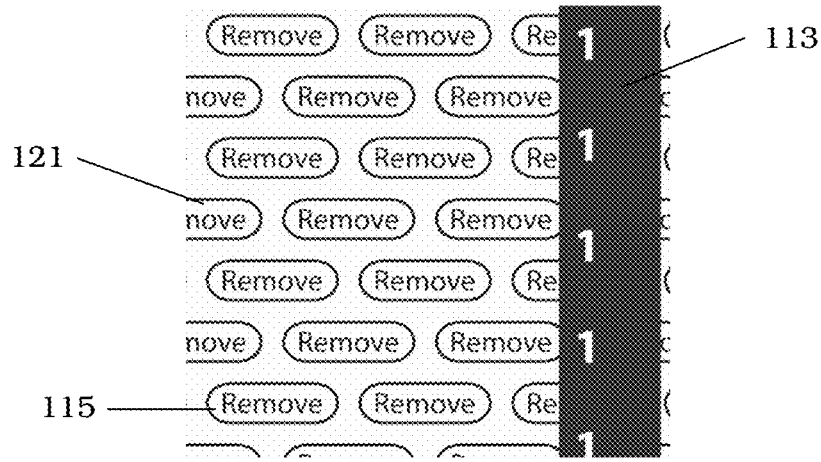
FIGS. 12B-12D are perspective views of liners for disposal over a surface of the retainer or anchor pad.
Figure 12C:
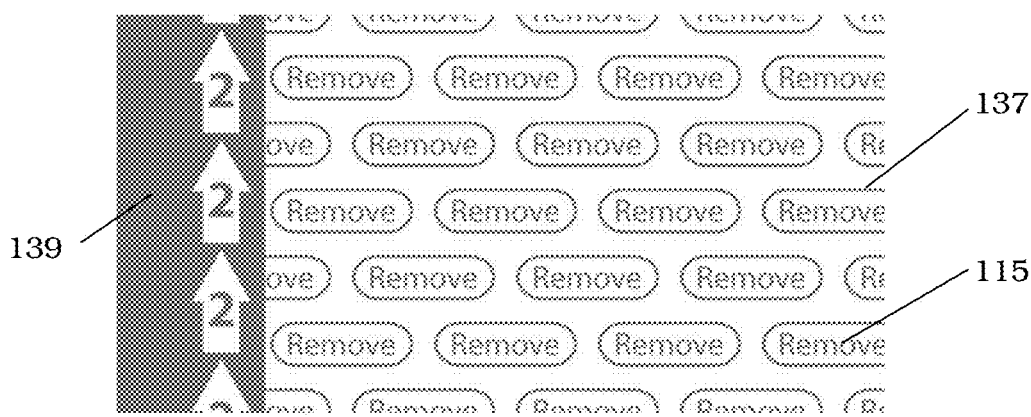
Figure 12D:
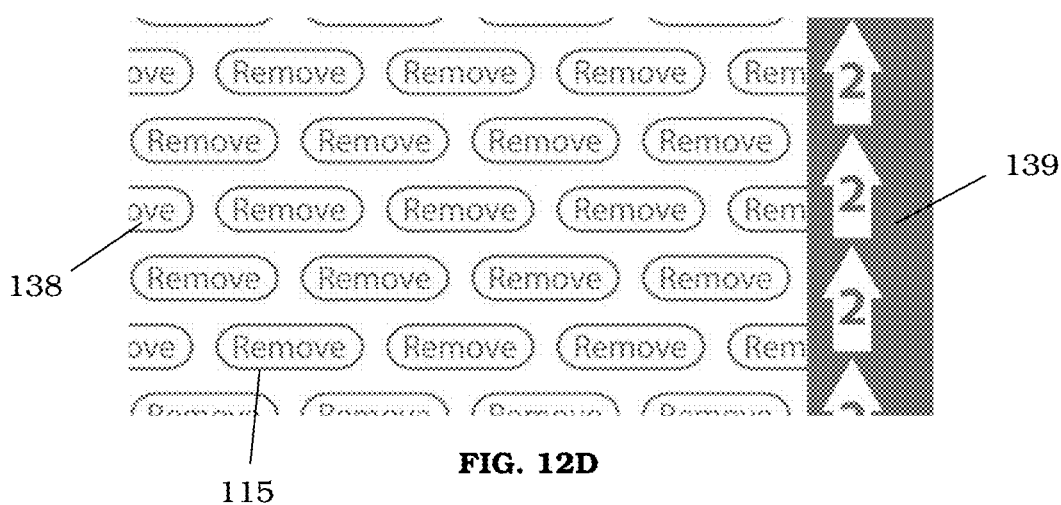
Figure 15:
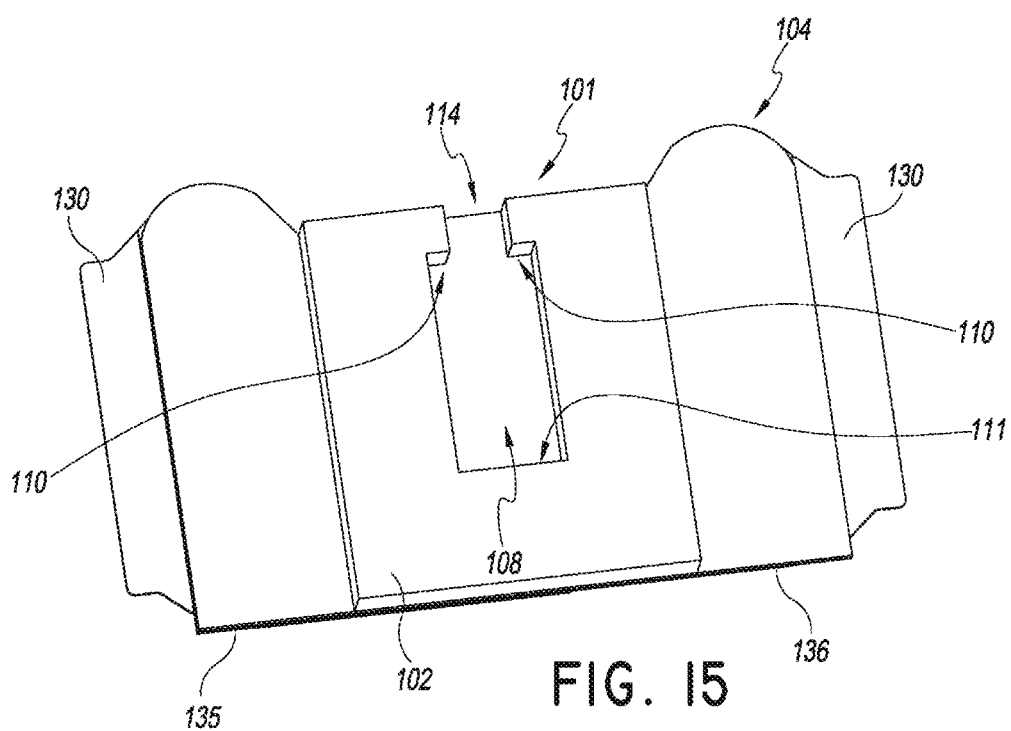
FIGS. 15-17 are perspective views of a method of using the securement device of FIG. 1. As shown, the method can continue by removing a first liner disposed over a portion of the bottom surface of the retainer. The retainer may be placed on a patient and a medical article may be placed in the retainer.

As shown in FIGS. 12A-D, the liner tabs 130 may include numbering to indicate the order in which the liners should be removed from the securement device, as well as a message, for example, "Remove" to indicate that the liners are to be removed prior to use of the securement device. FIG. 12A shows one embodiment with pull tab 112 of liner 120 including a "1" and pull tab 130 of liners 135 and 136 including a "2" inside of an arrow to distinguish from pull tab 112. As discussed above, the arrows may be positioned such that they indicate to the medical provider the proper orientation of the securement device. FIG. 12B shows one embodiment of a liner 121 including pull tab 113 with the number "1" on a solid color strip, for example black, with the message 115 "Remove" encircled repeated across a visible surface of the liner. The lines forming the encircled areas, as well as the text in the message 115 could be of the same color, which in one embodiment would match the solid color strip of the pull tab 113. FIG. 12C shows one embodiment of a liner 137 that covers one portion of a lower surface of the anchor pad, and FIG. 12D shows one embodiment of a liner 138 that covers another portion of a lower surface of the anchor pad. Both liners 137 and 138 may have the same solid color strip for pull tab 139, for example, green, and include the message 115 "Remove" encircled repeated across a visible surface of the liner. In one embodiment the liners 137 and 138 have a color scheme (e.g., solid color strip for pull tab, lines and text) the same as one another, and in another embodiment the color schemes are different. In one embodiment, the color scheme of liners 137 and 138 (whether different or the same) is different from the color scheme of liner 121 to further differentiate the liners from one another.

Figure 16:
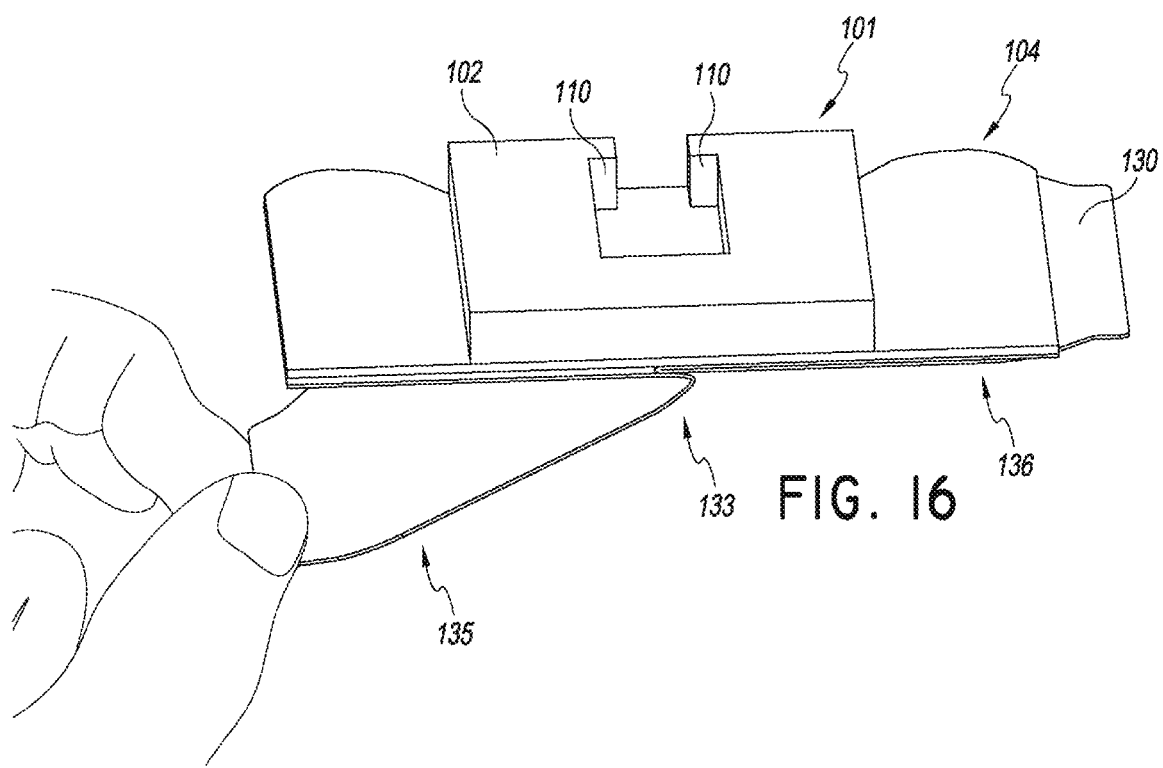

The process can continue by removing the liners covering the lower adhesive surface of the anchor pad 104 and placing a medical article within the retainer 101 as shown in FIGS. 15-19. As shown in FIG. 16, the liners covering the lower adhesive surface may comprise two liners 135 and 136 that cover about one half of the lower adhesive surface. The liners may fold back from the interface of the two liners 133 and extend out from the lower adhesive surface to form pull tabs 130. In this way, it is less likely that a medical provider will contact the lower adhesive surface with their hands and compromise the sterility of the lower adhesive surface. In some embodiments, the medical provider grabs one tab with each hand and partially removes the liners. The medical provider then places the anchor pad on the patient by moving the anchor pad towards the patient's skin while pulling the tabs to completely remove the liners.

Figure 17:
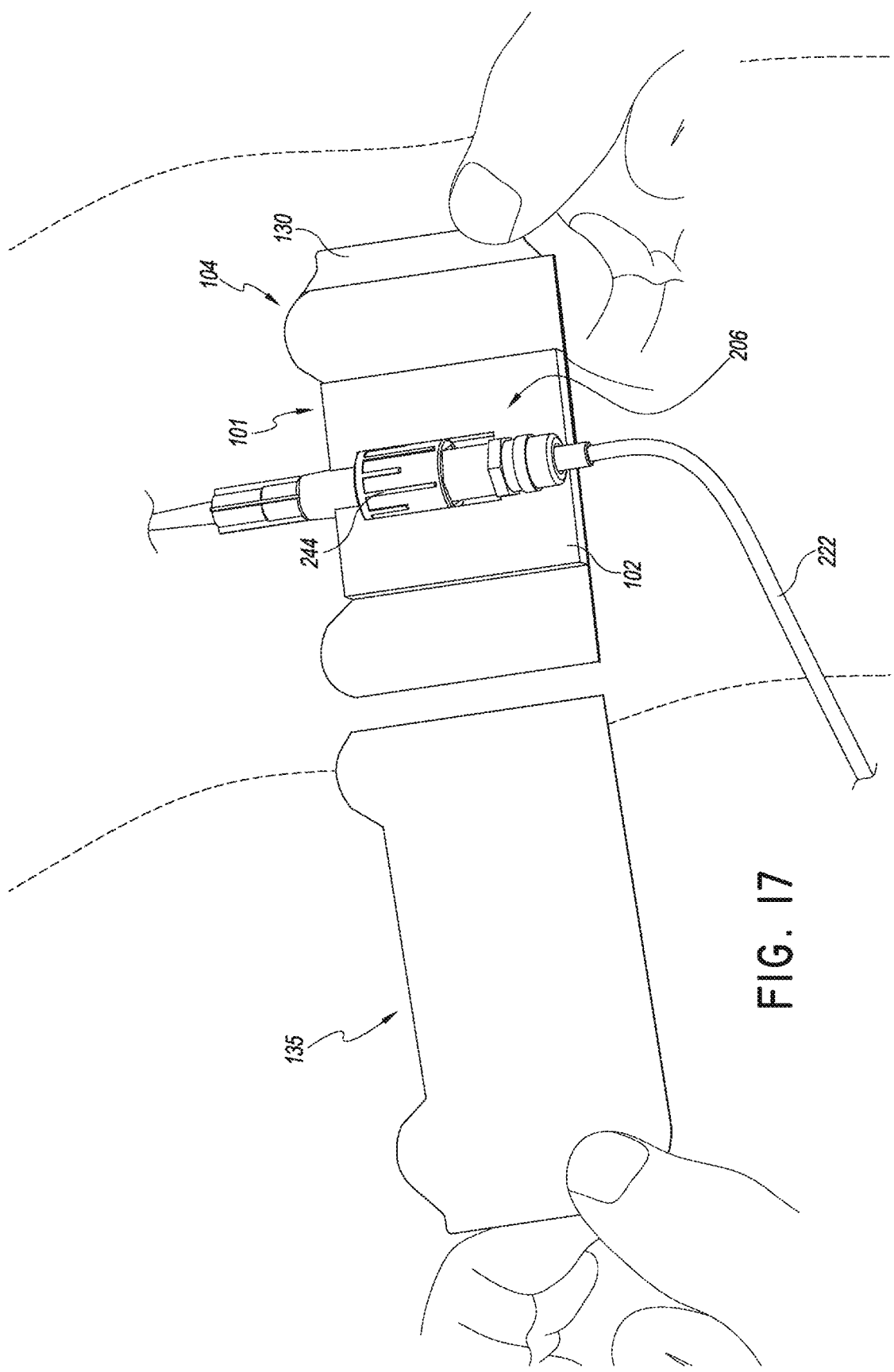

In the illustrated embodiment of FIG. 17, the securement device is slid under a medical article 200 and one liner 135 is removed. The medical article includes a spin nut 244. The spin nut 244 is at least partially disposed within the recess 108 and the channel formed in the retainer 101. In certain embodiments, a proximal surface of the spin nut 244 is in contact with a distal facing surface of the retainer 101. Downward pressure can be applied to the spin nut 244 such that a bottom surface of the spin nut 244 is pressed into contact with a bottom surface of the recess. Adhesive disposed on the upper surface 102 of the retainer 101 and/or within the recess may further secure the medical article to the retainer 101 and prevent the medical article from moving in any direction with respect to the retainer.

Figure 18:
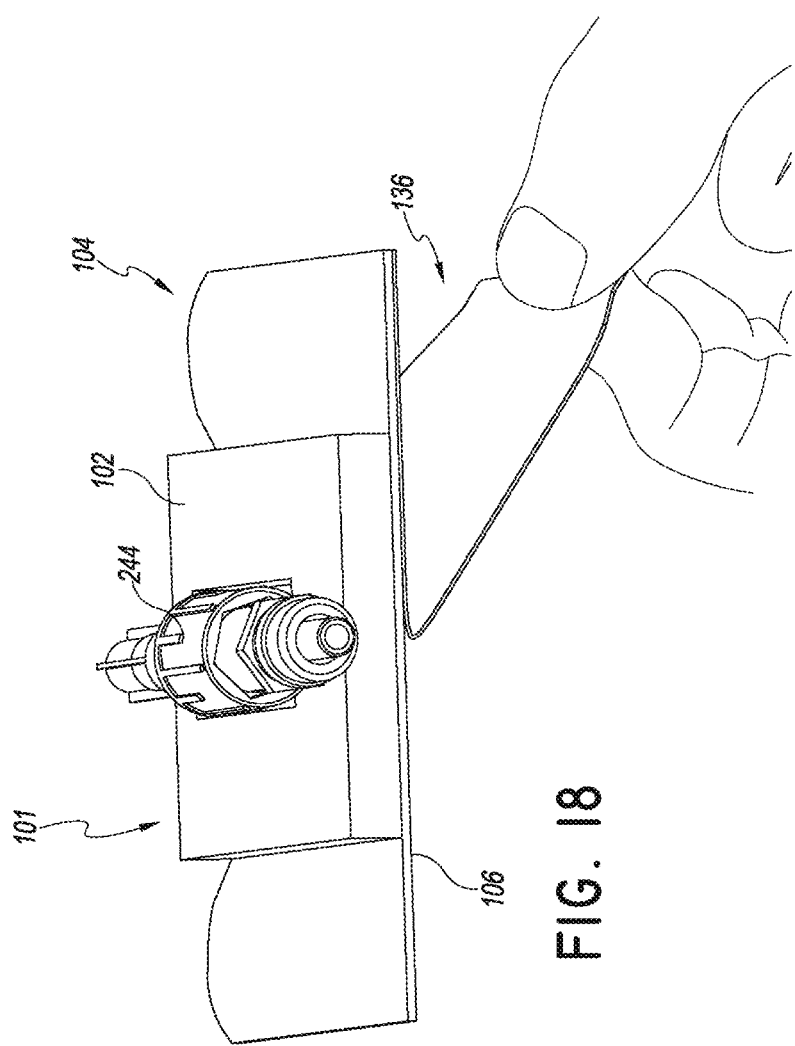
FIGS. 18-19 are perspective views of a method of using the securement device of FIG. 1. As shown, the method can continue by removing a second liner disposed over a portion of the bottom surface of the retainer. The retainer may be secured to the patient before or after the medical article is placed within the retainer.
Figure 19:
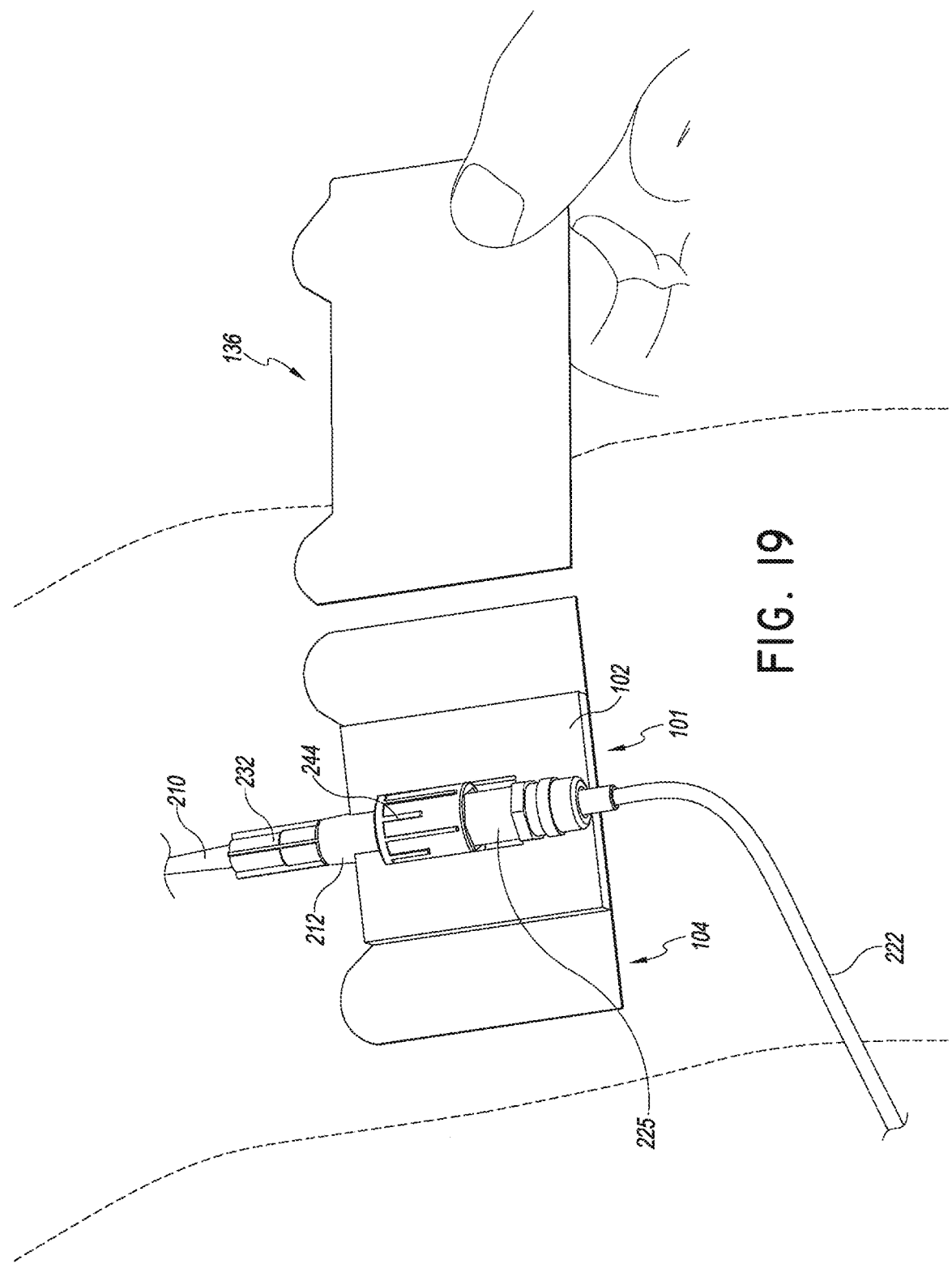

The process can continue by removing the second liner 136 covering the lower surface 106 of the anchor pad 104 as shown in FIGS. 18-19. In this way, the anchor pad 104 is secured to the patient's skin. The removal of the liners and insertion of the medical article within the retainer may be done in any order. In some embodiments, both liners are removed at substantially the same time. In addition, the medical article may be placed within the retainer either before or after the medical article is inserted into the patient. The securement device may be attached to the patient either before or after the medical device is at least partially inserted into the patient.

Figure 20:
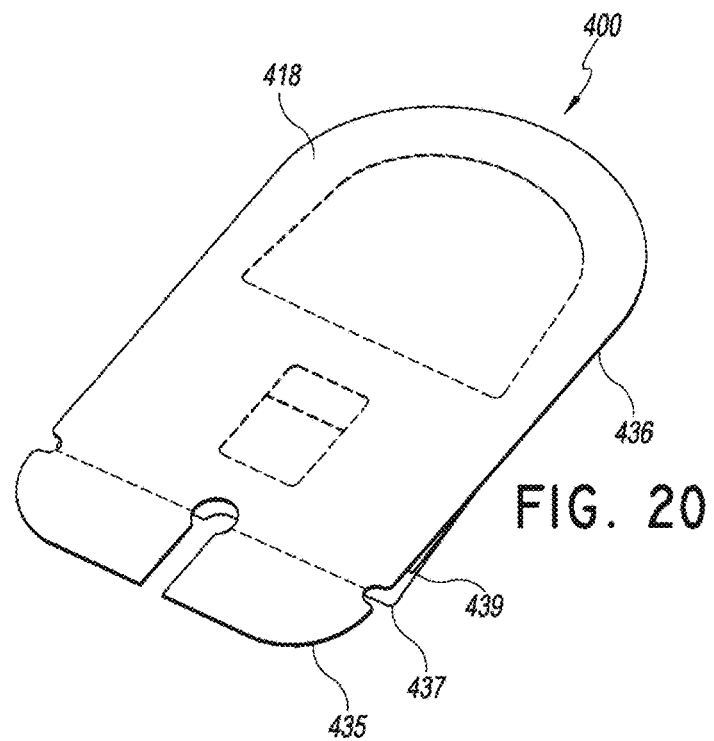
FIGS. 20-22 are perspective views of a method of using the dressing of FIG. 8. As shown, the method can begin by removing a first liner from a portion of a patient side surface of the dressing.
Figure 21:
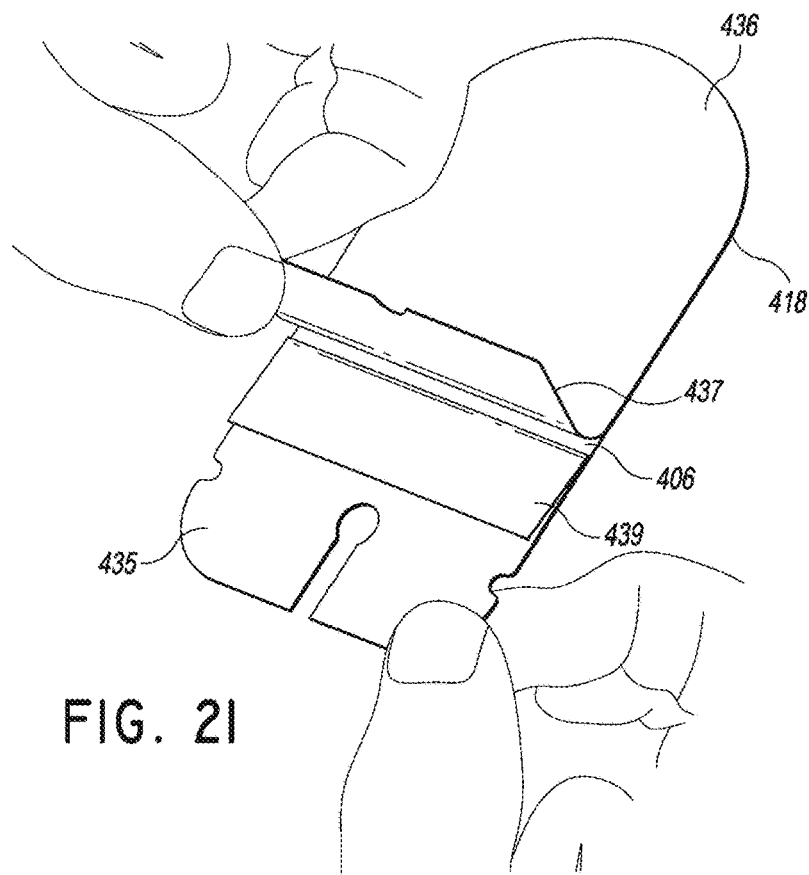
Figure 22:
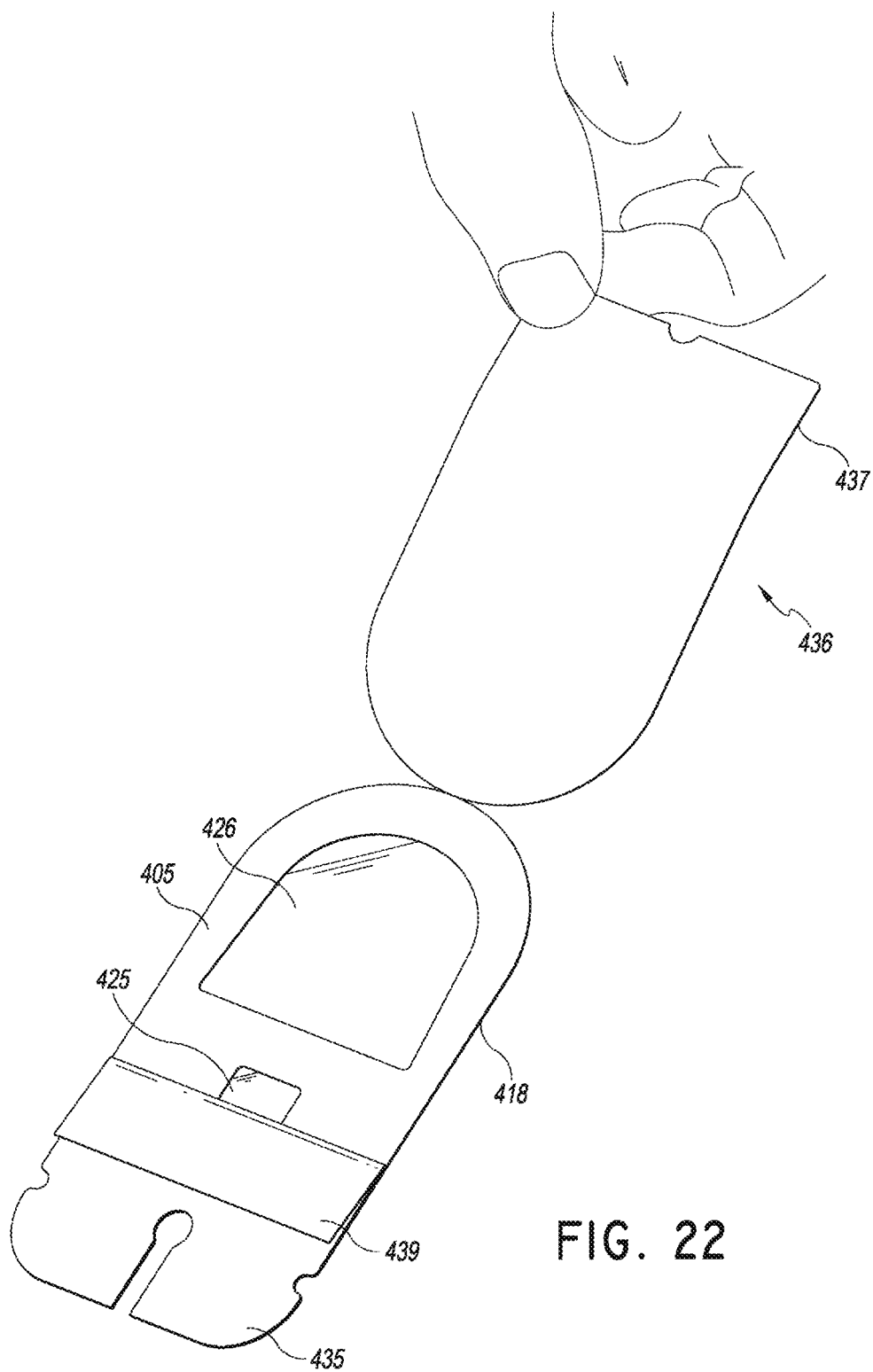
Figure 23:
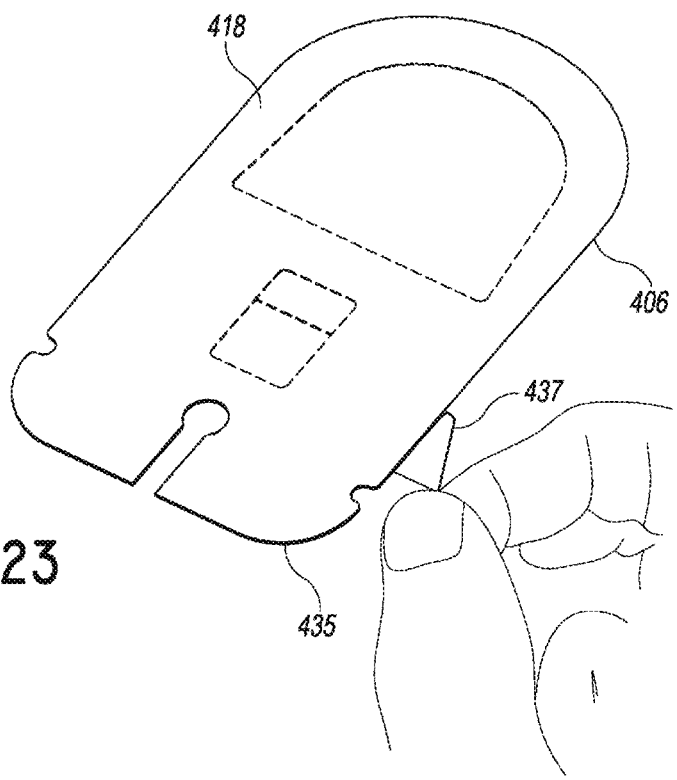
FIGS. 23-24 are perspective views of a method of using the dressing of FIG. 8. As shown, the method can begin by removing a second liner from a portion of a patient side surface of the dressing.
Figure 24:
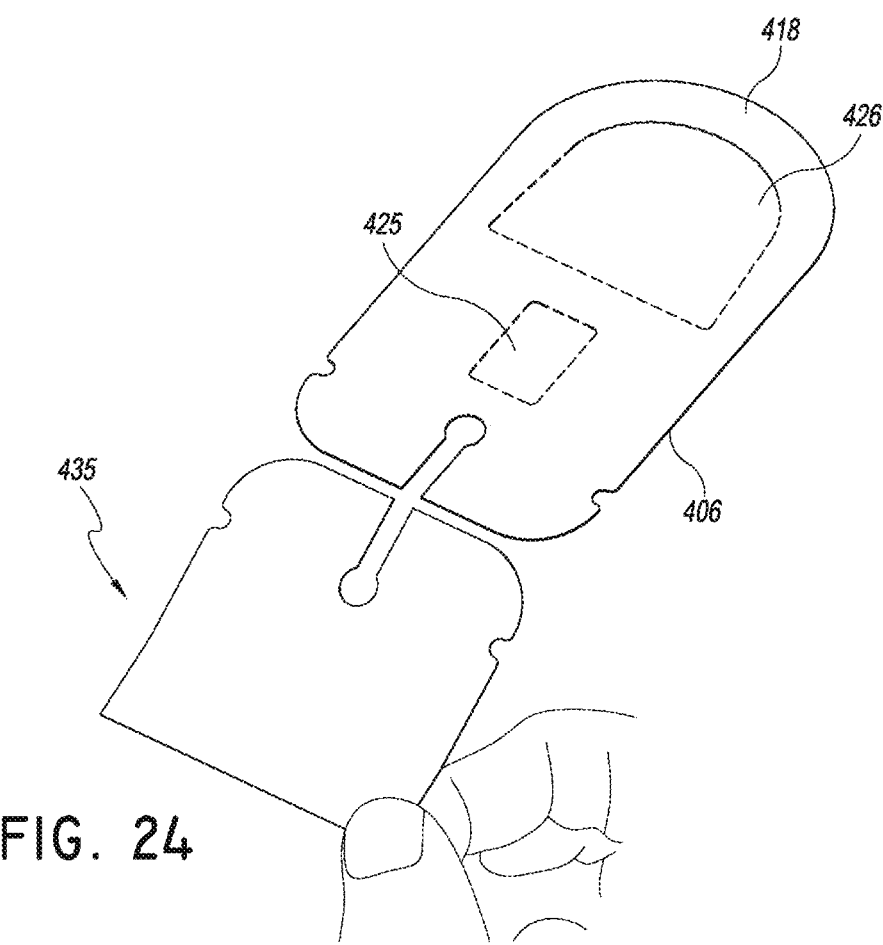

In some embodiments, the process of securing the medical article to the patient may continue by a obtaining an adhesive dressing, removing the dressing's liners, and placing the dressing over the securement device and insertion site as shown in FIGS. 20-26. FIG. 20 shows a top perspective view of the dressing 400 and FIG. 21 shows a bottom perspective view of the dressing 400. A medical provide may grab a portion 437 of the liner 436 that extends over the fold over section 439 of liner 435. In some embodiments, the medical provider may grab the portion 437 of liner 436 and the fold over section 439 of liner 435 at the same time. However, as shown in FIG. 22, liner 436 may be removed first to reveal a transparent or partially transparent insertion window 426, a transparent or partially transparent retainer window 425, and an adhesive surface 406. In some embodiments, a portion of 438 of liner 436 covers at least a portion of the retainer window 425. As such, when liner 436 is removed during placement, the medical practitioner can see through at least a portion of the transparent retainer window 425 to view the medical device and assist in proper placement of the dressing. Release liner 435 may then be removed as shown in FIGS. 23-24.

Figure 25:
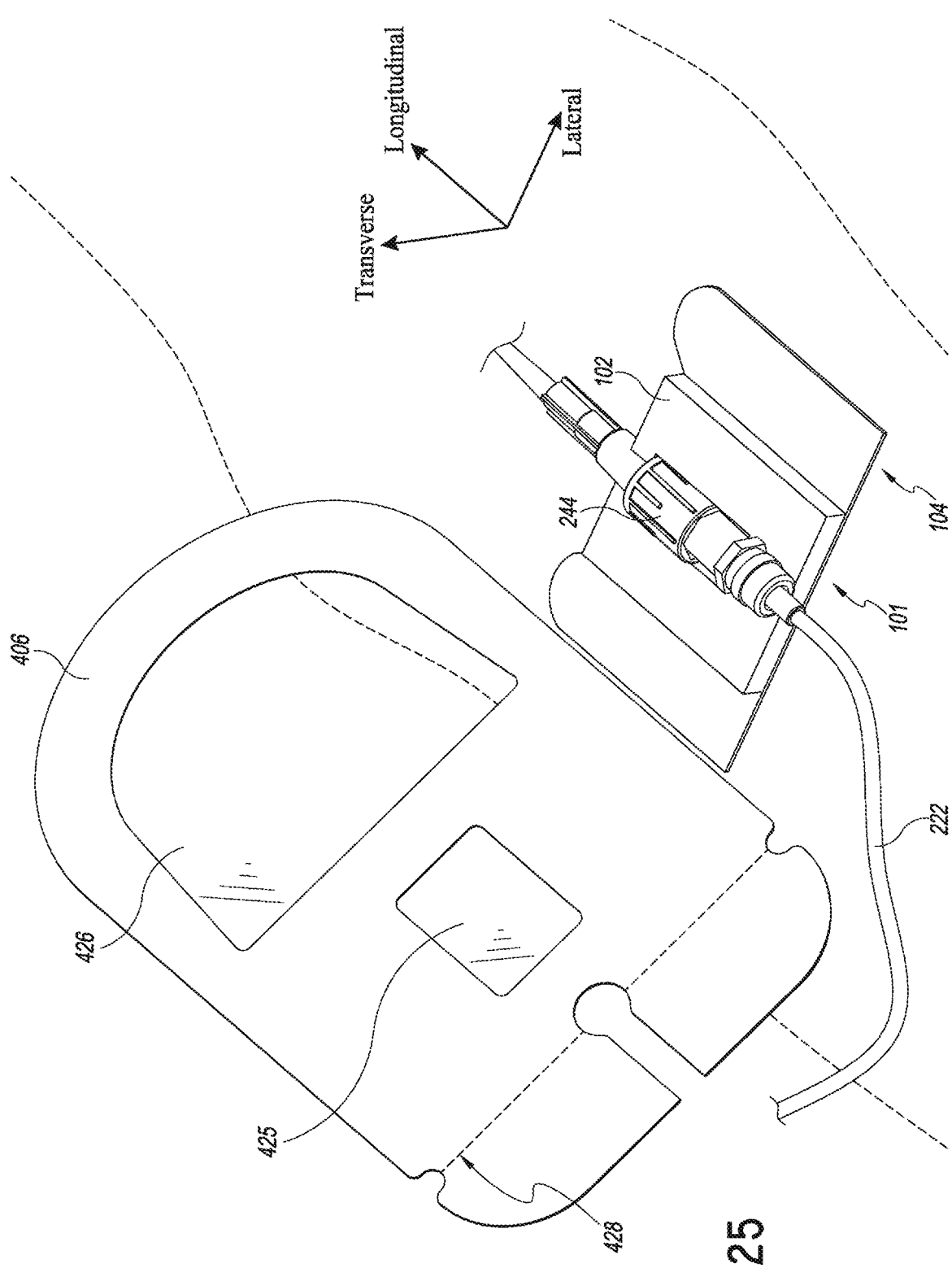
FIGS. 25-26 are perspective views of a method of using the dressing of FIG. 8. As shown, the method can continue by placing the dressing over the insertion site and at least a portion of the medical article.
Figure 26:
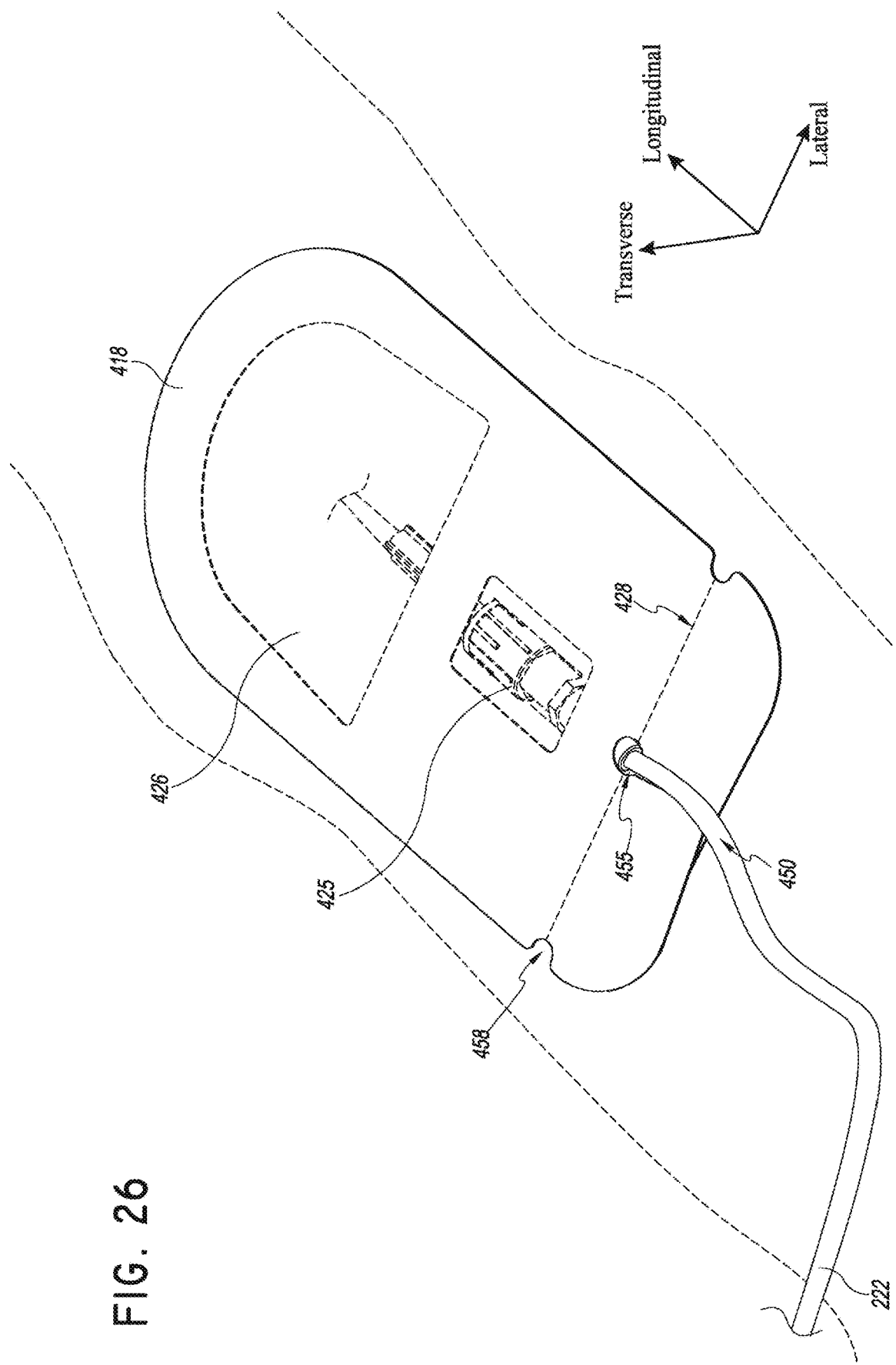

After the liners are at least partially removed from the dressing 400, the dressing can be placed over the insertion site and adhered to the patient with a suitable adhesive surface 406 on the underside of the dressing 400 as shown in FIGS. 25-26. In some embodiments, the dressing is configured to be waterproof or otherwise impermeable to liquids and in some embodiments also restricts the flow of air. In other embodiments, the dressing may be configured to be breathable, allowing air and/or moisture near an insertion site through to the other side of the dressing and away from the insertion site, while keeping at least external moisture on the other side of the dressing away from the insertion site. In some embodiments, the dressing is impermeable to viruses and bacteria, and may comprise or be coated with an anti-bacterial or anti-microbial material. In some embodiments, the dressing comprises or is coated with a waxy material. The combination of the dressing covering the medical device and the anchor pad and retainer located underneath the medical device can create a 360 degree holding of the medical device.

As shown in FIG. 26, the insertion site and at least a portion of the medical article can be seen through the windows 425 and 426. In addition, the medical line 222 may pass through the channel 450 in the distal side of the dressing to rest within opening 455. Thus, a portion of the dressing may close around the medical line 222 at the distal end of the dressing. In this way, fluids, foods, and/or other contaminants are prevented from entering the insertion site.

To remove a distal portion dressing and release the medical tube 222, a medical provider may tear along the perforation 428 located by notches 458 and remove the distal portion of the dressing. In some embodiments the securement device, dressing, and/or tape is included in a kit. The kit may further include instructions for using the kit components.

Figure 27:
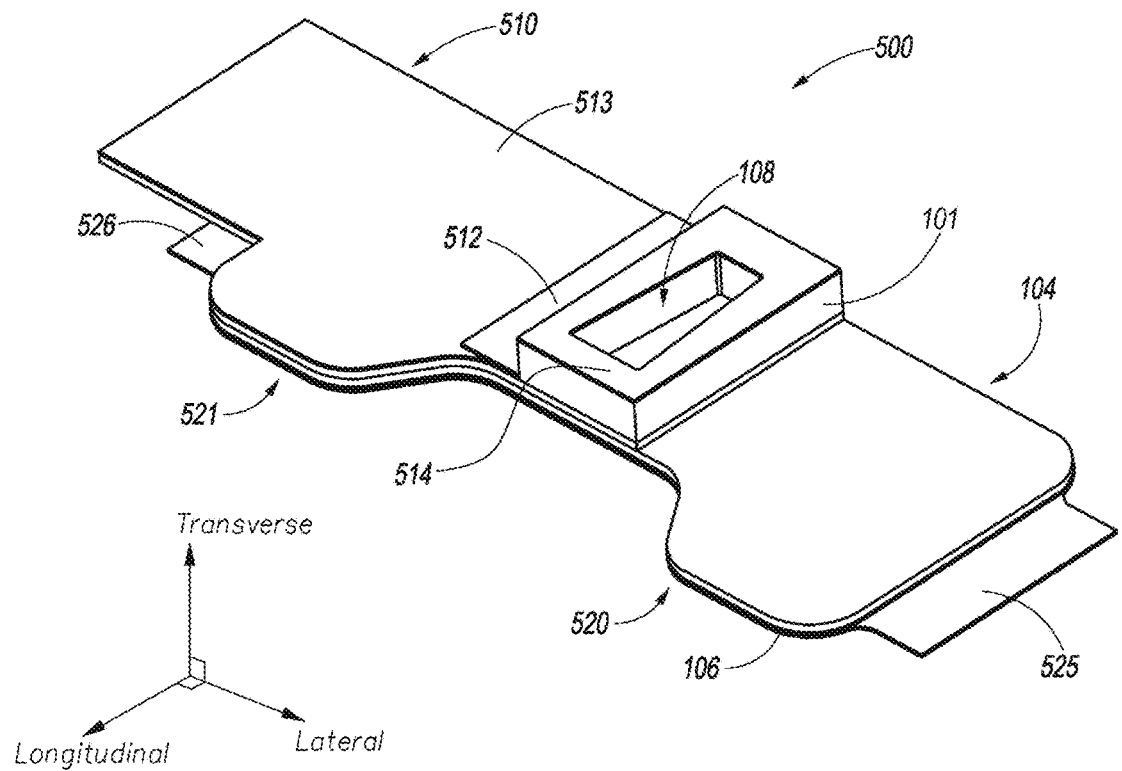
FIGS. 27-28 are perspective views of a securement device according to another embodiment of the present invention.
Figure 28:
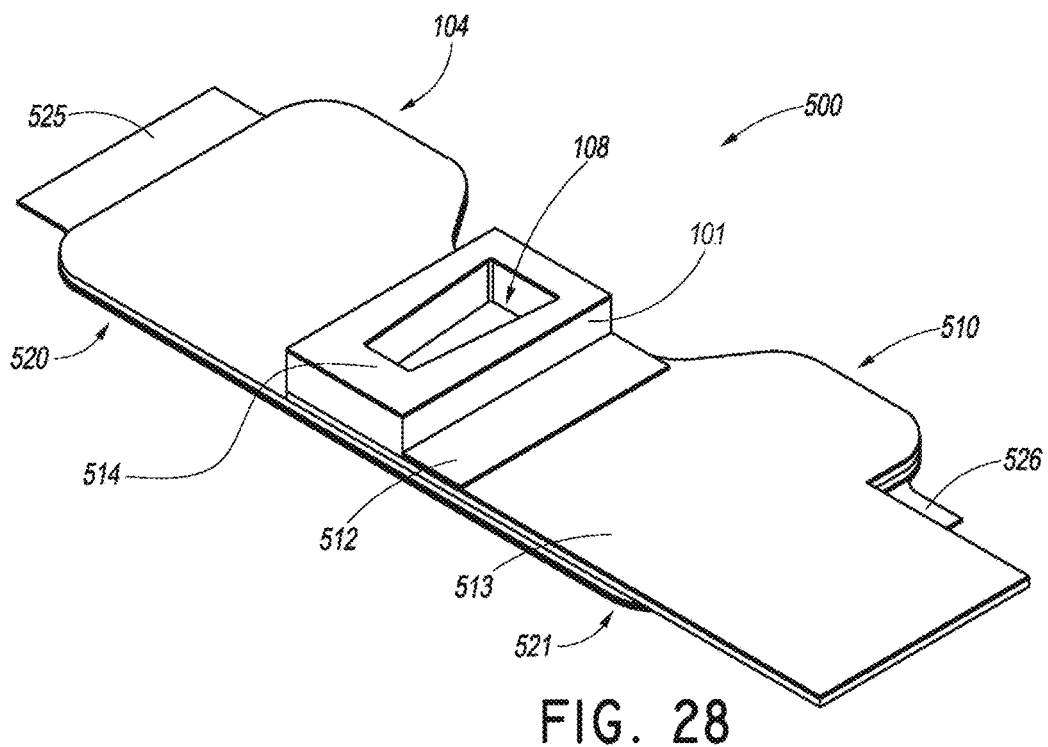

With reference now to FIGS. 27-28, an embodiment of a securement device 500 includes an anchor pad 104, a retainer 101, and a flap 510. The anchor pad 104 is configured to be secured to a patient's skin. In some embodiments, at least a portion of a lower surface 106 of the anchor pad 104 includes an adhesive. The retainer 101 is configured to receive and secure at least a portion of a medical article. In the illustrated embodiment of FIGS. 27-28, the retainer 101 includes a recess 108 shaped to receive at least a portion of the medical article. In some embodiments, at least a portion of the upper surface of the retainer 108 includes an adhesive. The flap 510 is configured to fold over the retainer 101.

With reference now to the flap 510, it can be seen in FIG. 27 that the flap 510 is attached to and/or integrated with the securement device 500. The flap 510 is configured to fold, bend, or rotate down over the retainer 101. The flap 510 and the anchor pad 104 and/or the retainer 101 may be formed as an integral, single piece. Alternatively, the flap 510 and the anchor pad 104 may be formed separately and then attached together. In this case, the flap 510 and the anchor pad 104 may be attached by any means or mechanism that allows the flap 510 to fold, bend, or rotate down over the retainer 101. Attachment means include glue or adhesive, a weld of the materials, heat sealing, mechanical fasteners such as staples or eyelets, or other such means of attachment.

A liner 513 may cover an adhesive surface of the flap 510. The adhesive surface is configured to adhere to a medical article, portions of the retainer 101, portions of a medical article, and/or to portions of the upper surface of the anchor pad 104. The liner 513 may cover the entire surface of the flap 510 or may only cover adhesive portions of the flap 510. The flap 510 and liner 513 may be prepared such that the liner 513 maintains a covered surface of the flap 510 in a sterilized state. As illustrated in FIG. 28, the liner 513 includes a tab 512. The tab 512 can allow the healthcare provider to easily grip a portion of the liner 513 and pull the liner 513 away from the upper surface of the flap 510, thus removing the liner 513 and exposing an adhesive surface. The tab 512 may be integral to the liner 513 and in some embodiments comprises a fold over section of liner 513.

Figure 29:
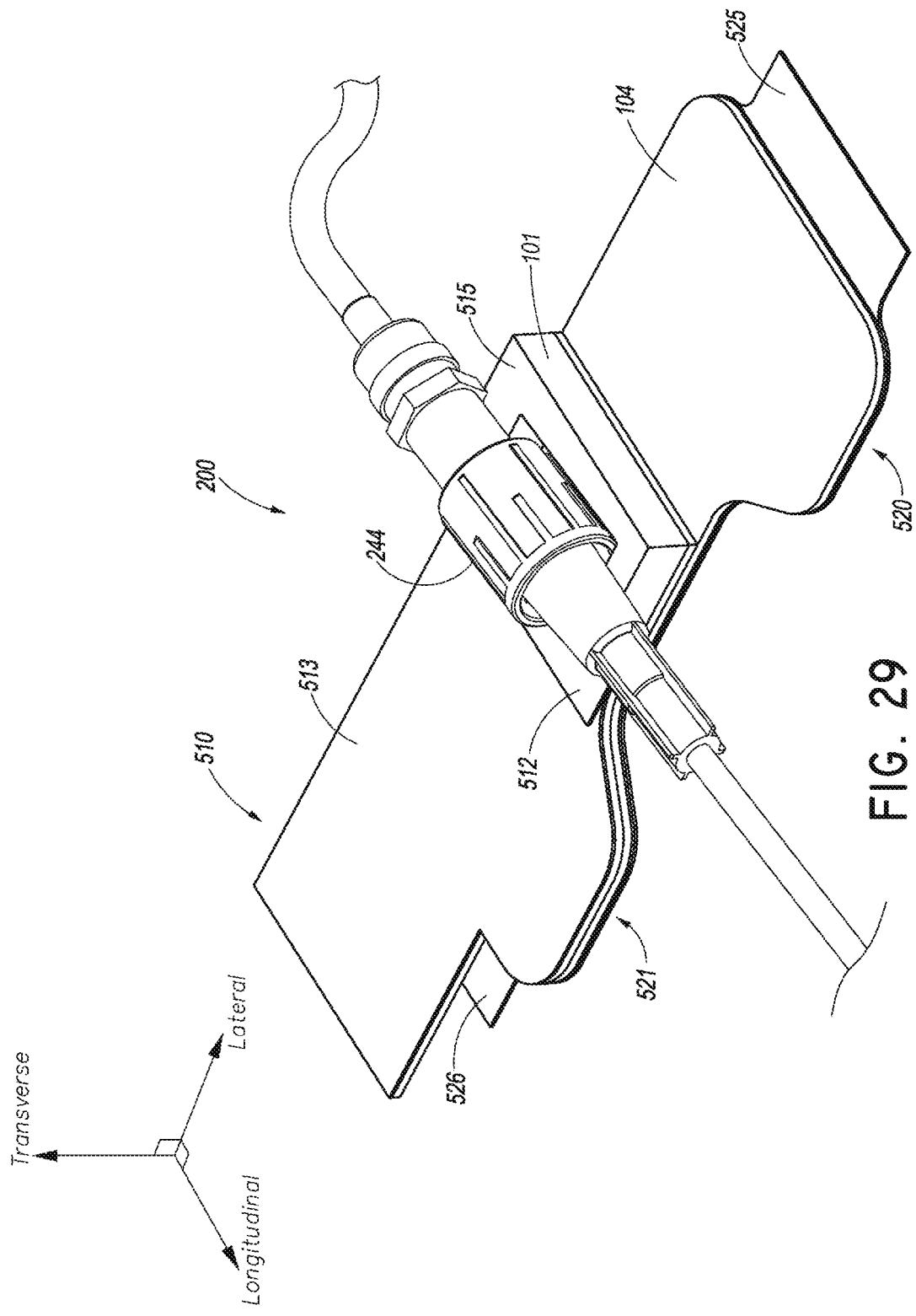
FIG. 29 is another perspective view of the securement device of FIG. 1 and shows a medical article placed in the retainer prior to a flap of the retainer being folded across the medical article.

With reference now to the retainer 101, FIGS. 27-28 show a retainer that includes a recess 108. The recess 108 may be any suitable size and shape. As shown, the recess 108 is generally shaped as an elongated trapezoid. In this way, the longitudinally tapered walls of the recess 108 can serve as an abutment surface for a portion of a medical article placed within the retainer 101. Turning briefly to FIG. 29, the proximal wall of the recess 108 may serve as an abutment surface as well. In other words, a proximal surface of a spin nut 244 may abut against a distal facing surface of the retainer 101 so as to prevent movement of a catheter 200 in the proximal direction. In some embodiments, the retainer 101 is configured to suspend the spin nut 244 above the skin of a patient to allow for the catheter 200 to be inserted into the patient's skin at an angle relative to the skin of the patient, for example, 7 degrees.

Returning to FIGS. 27-28, at least a portion on the lower surface of the recess 108 can include an adhesive. Other surfaces of the retainer 101 may also include an adhesive. For example, in some embodiments, one or more walls that form the recess 108 include an adhesive. An adhesive may also be included on the uppermost surface of the retainer 101. The adhesive can adhere to one or more surfaces of a medical article 200 placed within the retainer 101 so as to further limit movement of the medical article 200.

Figure 30:
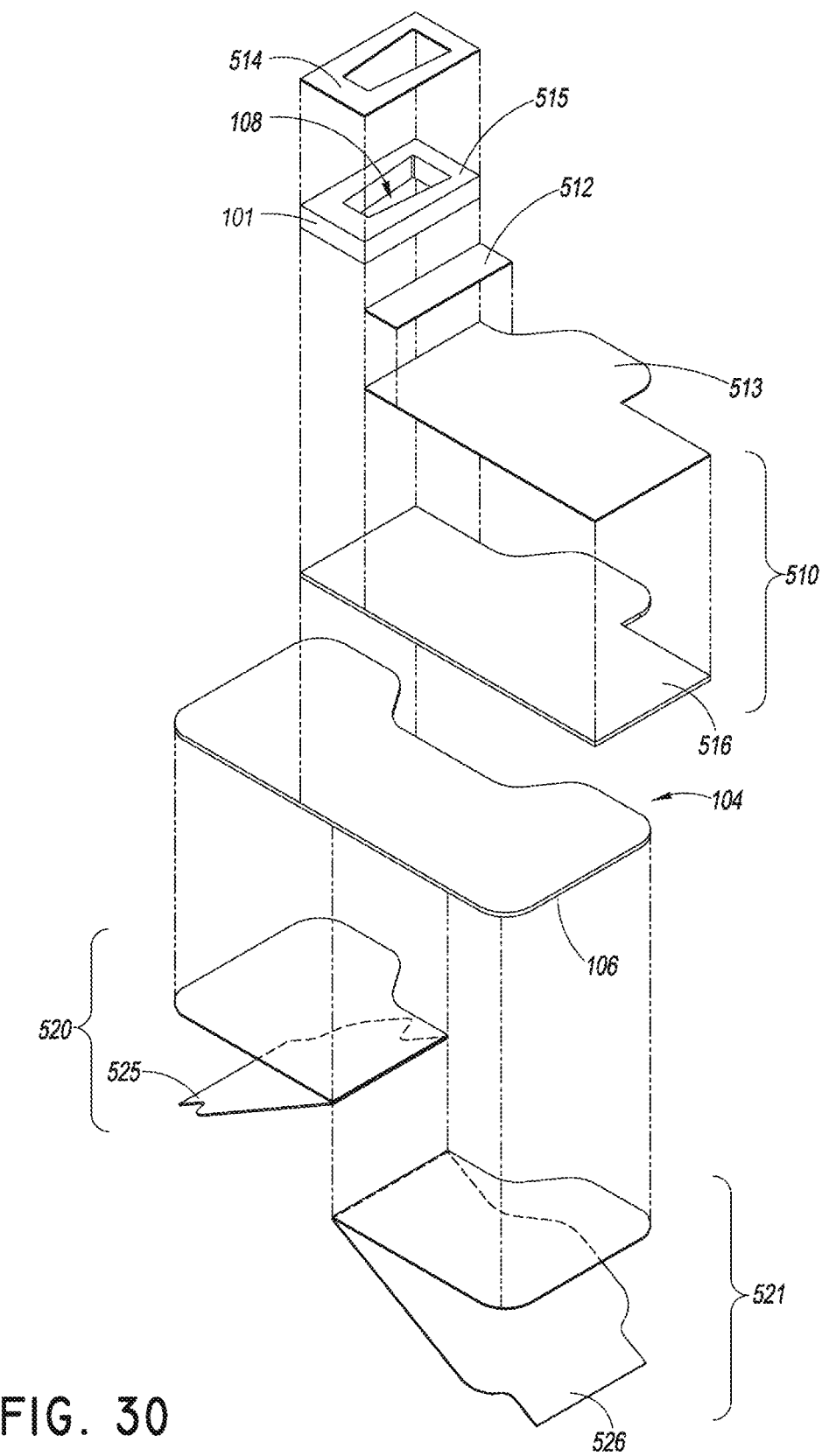
FIG. 30 is an exploded view of the securement device of FIG. 27.

FIG. 30 is an exploded view of the securement device 500 of FIG. 29. As shown, the retainer 101 may be disposed on a portion of the flap 510. However, in some embodiments, the retainer 101 is disposed on the anchor pad 104. A liner 514 may be disposed over the retainer 101. As shown, the liner 514 covers the upper surfaces of the upwardly extending walls forming the recess 108. In this embodiment, the uppermost surfaces 515 of the retainer 101 include an adhesive surface which may be covered by the removable liner 514.

The flap 510 may include an adhesive surface 516 which may be covered by removable liner 513. The flap 510 is configured to fold, bend, or rotate down over the retainer 101. In this way, when closed, the underside of the flap in the closed position can adhere to one or more surfaces on the anchor pad and/or retainer and/or medical article. The flap 510 may rest on a portion of the anchor pad 104. In some embodiments, the flap 510 is coupled to at least a portion of the anchor pad 104 and/or at least a portion of the retainer 101. In some embodiments, at least a portion of an upper surface of the anchor pad on the side that is opposite to the flap 510 includes an adhesive surface. In this way, the adhesive on the upper surface of the anchor pad opposite to the flap 510 can further secure the flap 510 when the flap is folded over the retainer 101.

The anchor pad 104 may include a lower surface 106 with an adhesive layer such that the anchor pad 104 may be secured to the skin of a patient when liners 520 and 521 are removed. Liners 514, 520, and 521 may be similar to or the same as the liners described above. As shown in FIG. 30, the liners 520 and 521 may comprise two sections that are hingedly connected. At least a portion of the liners 520 and 521 may be sized to extend out from the perimeter of the anchor pad forming pull tabs 525 and 526.

Figure 31:
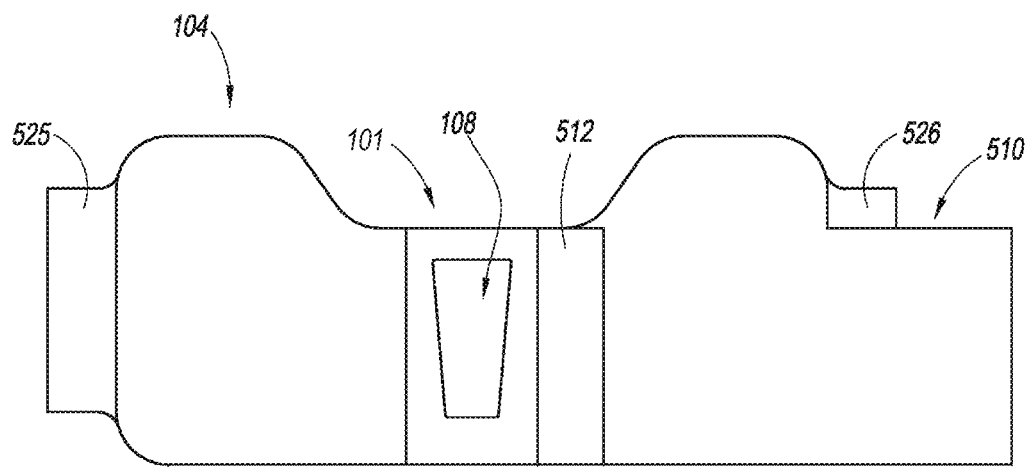
FIG. 31 is a plan view of the securement device of FIG. 27.

FIG. 31 shows a plan view of the securement device 500. As shown, the recess 108 in the retainer 101 is roughly trapezoidal in shape having a narrower width at the proximal end than the width at the distal end. In this way, various medical devices and/or spin nuts may be at least partially inserted within the retainer 101 as discussed above. In some embodiments, the side walls of the retainer running generally from the distal end to the proximal end of the device may function as abutment surfaces. Thus, these side walls may abut against a proximal facing side of a media article or portion thereof when the article is placed within the recess 108 to prevent movement of the article in at least the proximal direction.

Figure 32:
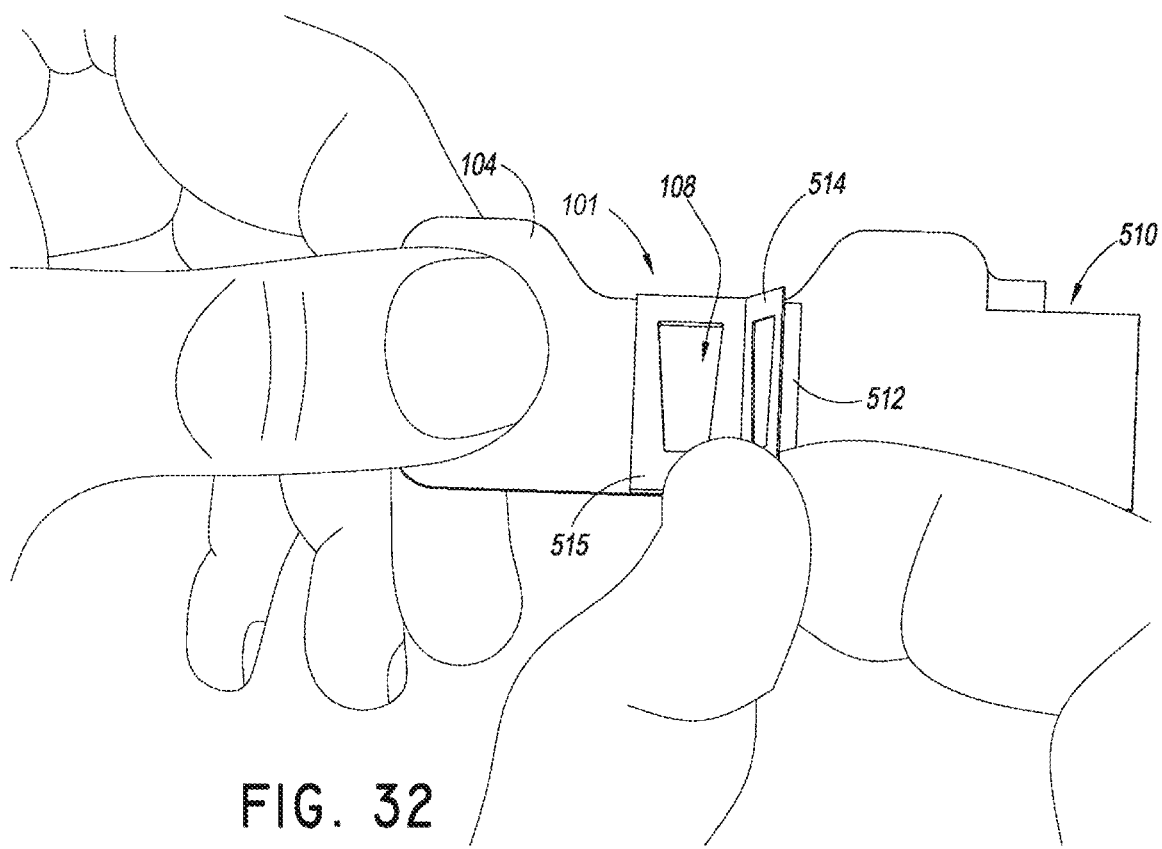
FIG. 32 is a top view of a method of using the securement device of FIG. 27. As shown, the method can begin by removing a liner disposed over the retainer.
Figure 33:
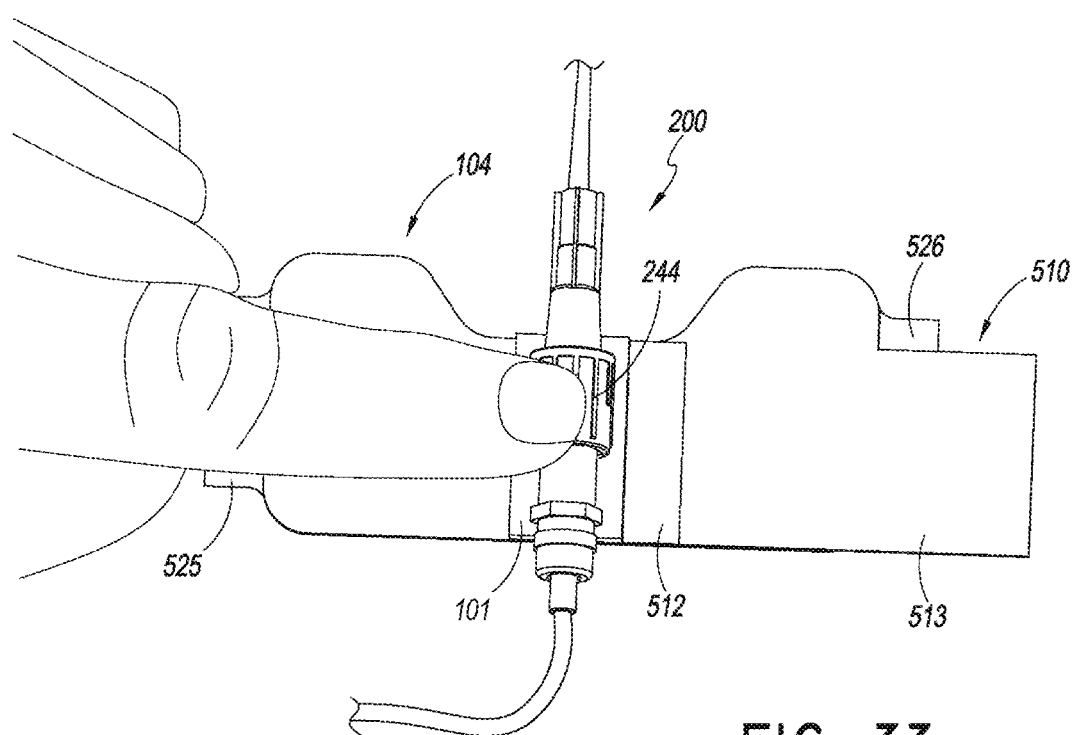
FIG. 33 is a top view of a method of using the securement device of FIG. 27. As shown, the method can continue by placing a medical article in the retainer.

In operation, a method of using the securement device 500 described above and a process for coupling a medical article to a patient can begin by removing the liner 514 covering the uppermost surfaces of the retainer 101 as illustrated in FIG. 32. The process can continue by placing a medical article 200 within the recess 108 of the retainer 101. As shown, the medical article 200 includes a spin nut 202. The retainer 101 of the securement device can be positioned such that at least a portion of the spin nut 244 is above the retainer 101. As shown in FIG. 33, downward pressure can be applied to the spin nut 244 such that the spin nut 244 can be moved at least partially into the recess 108 of the retainer 101 and in contact with at least one adhesive surface of the retainer 101.

Figure 34:
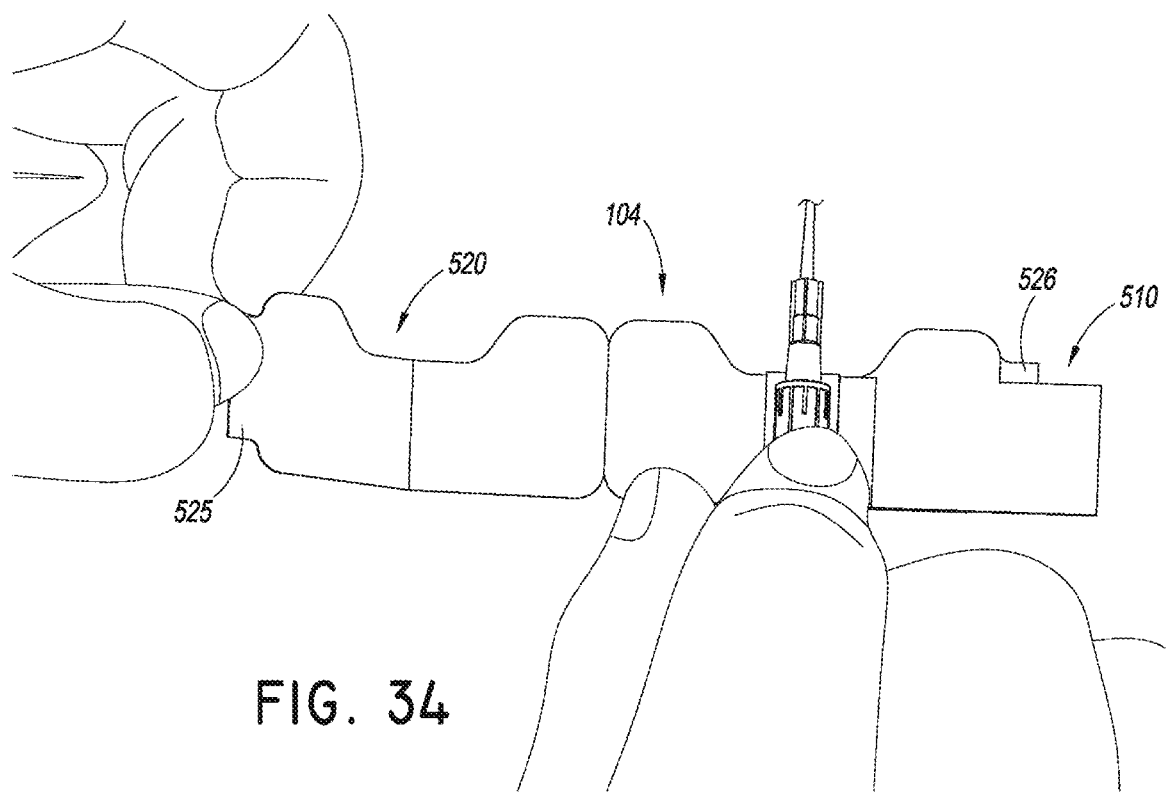
FIGS. 34-36 are top views of a method of using the securement device of FIG. 27. As shown, the method can continue by removing the liners covering the lower surfaces of the anchor pad.
Figure 35:
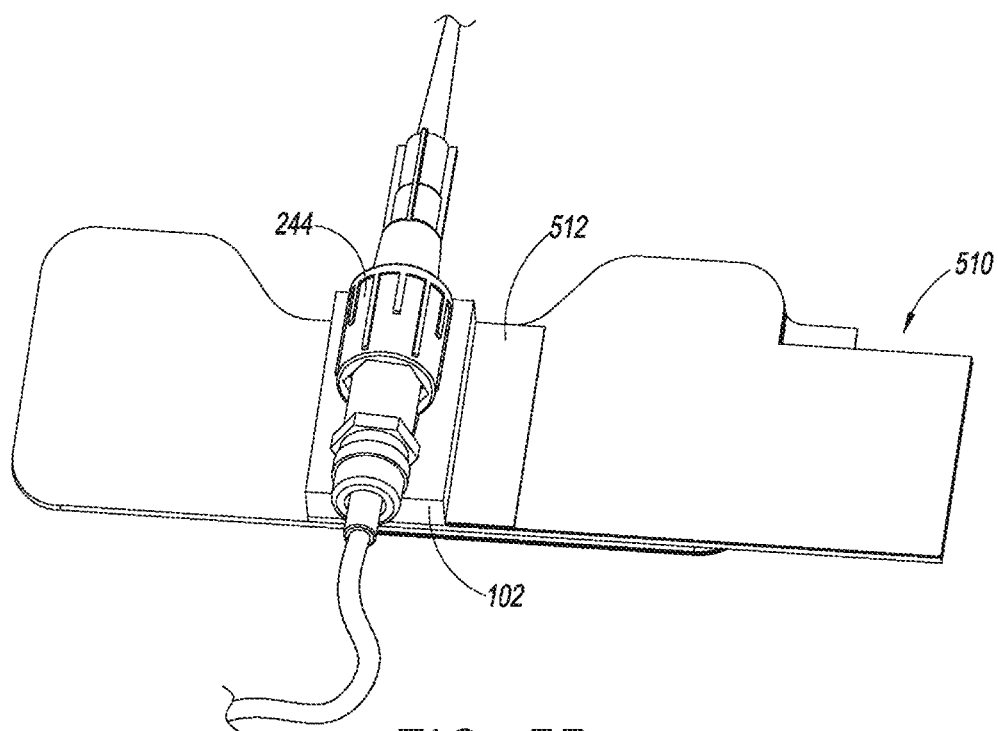
Figure 36:
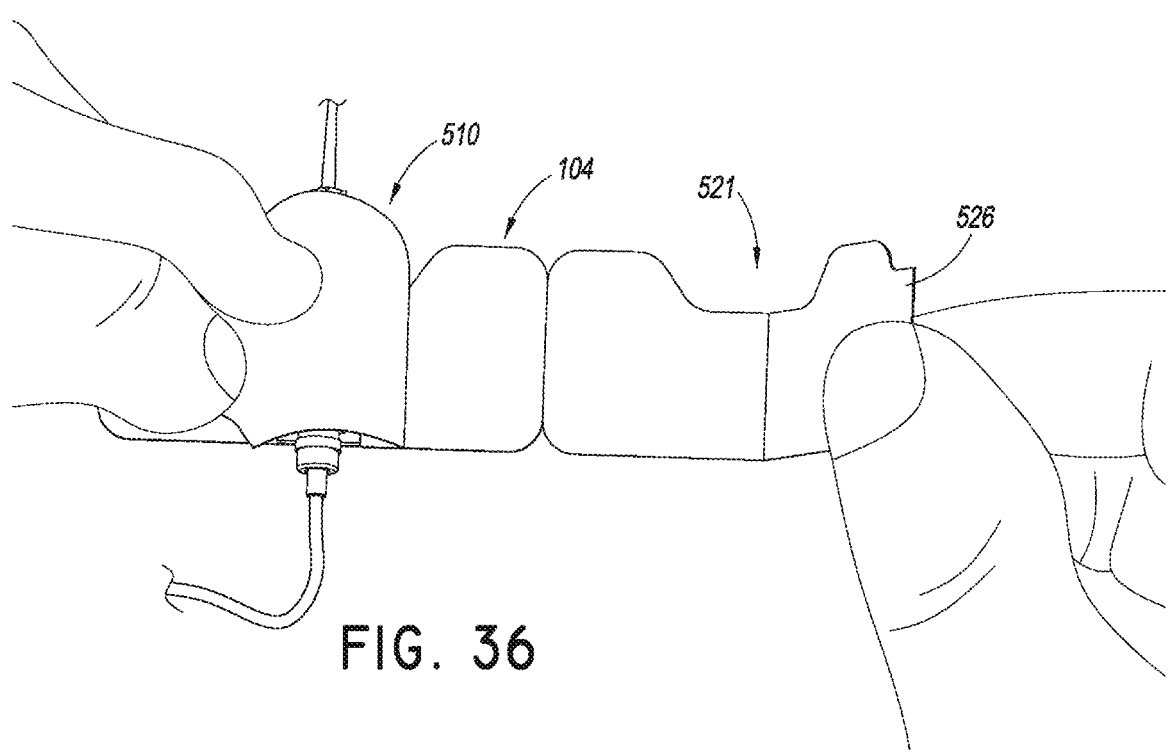

The process can continue by removing the liners 520 and 521 covering the lower surface 106 of the anchor pad 104 as shown in FIGS. 34-36. In this way, the anchor pad 104 is secured to the patient's skin. As shown in FIG. 34, the liner 520 may be removed by grabbing the pull tab 525 and pulling the liner 520 away from the lower surface of the anchor pad 104. Thus, as shown in FIG. 35, the right hand side of the anchor pad is secured to the patient's skin. Similarly, as shown in FIG. 36, the liner 521 may be removed by grabbing the pull tab 526 and pulling the liner 521 away from the lower surface of the left hand side of anchor pad 104. As illustrated in FIG. 36, a user may wish to hold the flap 510 away from the anchor pad 104 in order to better access the pull tab 526. With the liners 520 and 521 removed from the lower surface 106 of the anchor pad 104, the anchor pad 104 is secured to the patient's skin.

Figure 37:
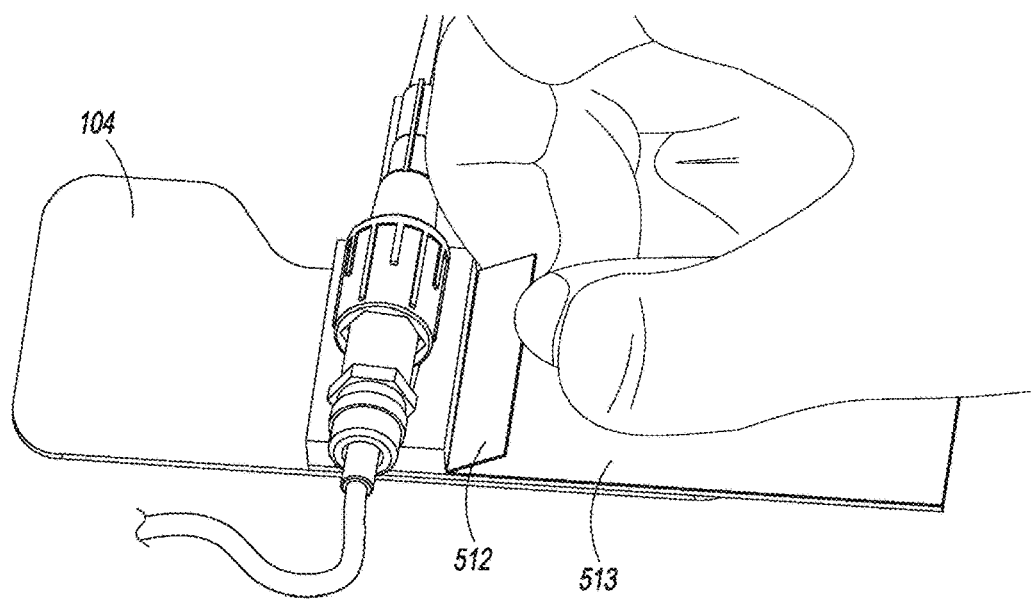
FIGS. 37-38 are top views of a method of using the securement device of FIG. 27. As shown, the method can continue by removing the liner on the adhesive surface of the flap.
Figure 38:
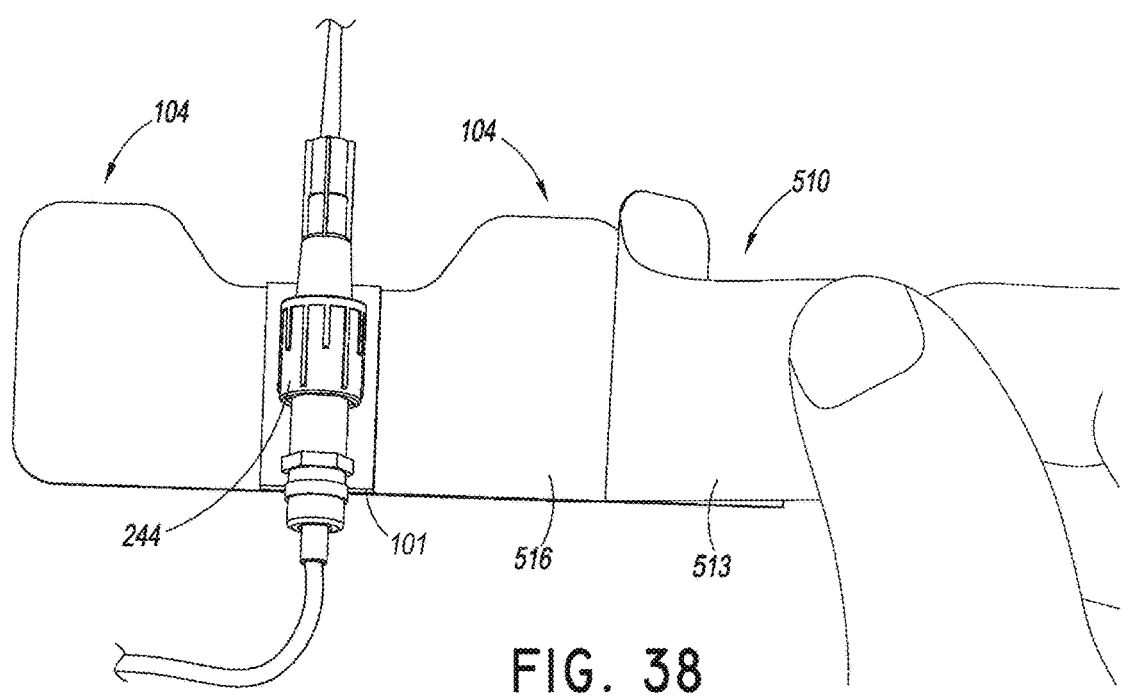
Figure 39:
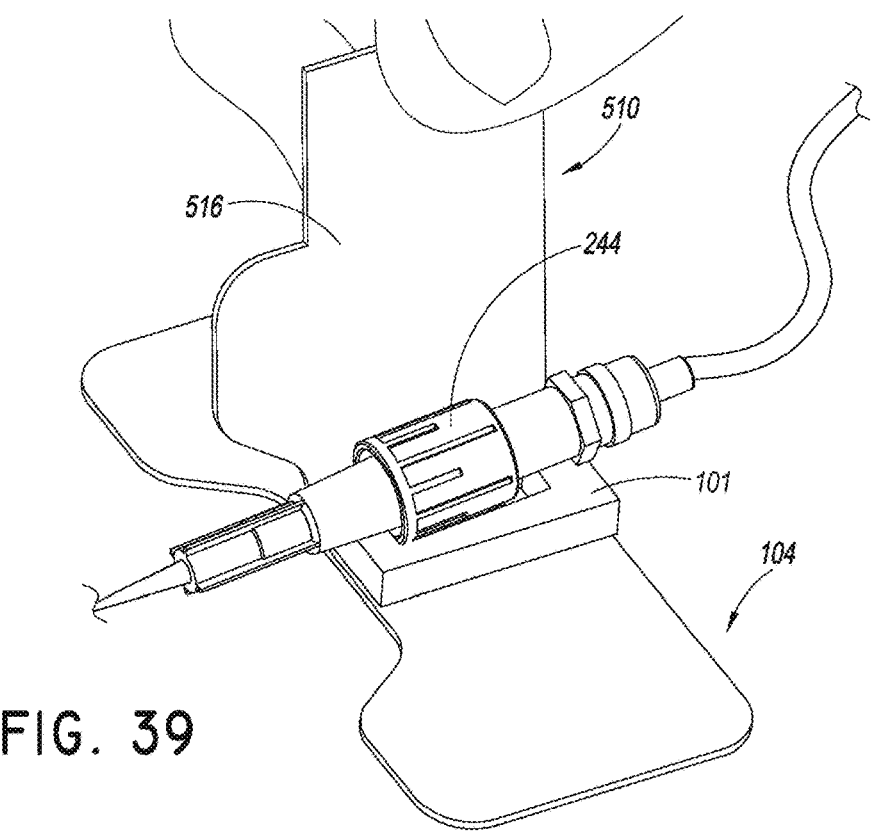
FIGS. 39-40 are top views of a method of using the securement device of FIG. 27. As shown, the method can continue by folding the flap across an upper surface of the medical article.
Figure 40:
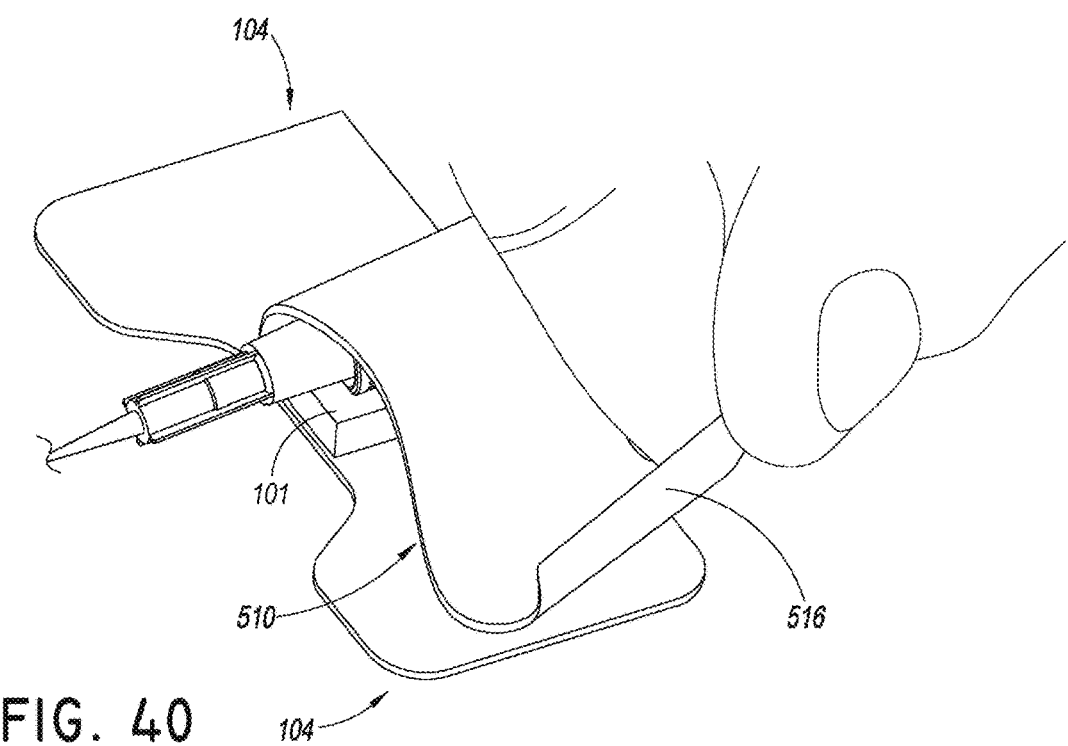
Figure 41:
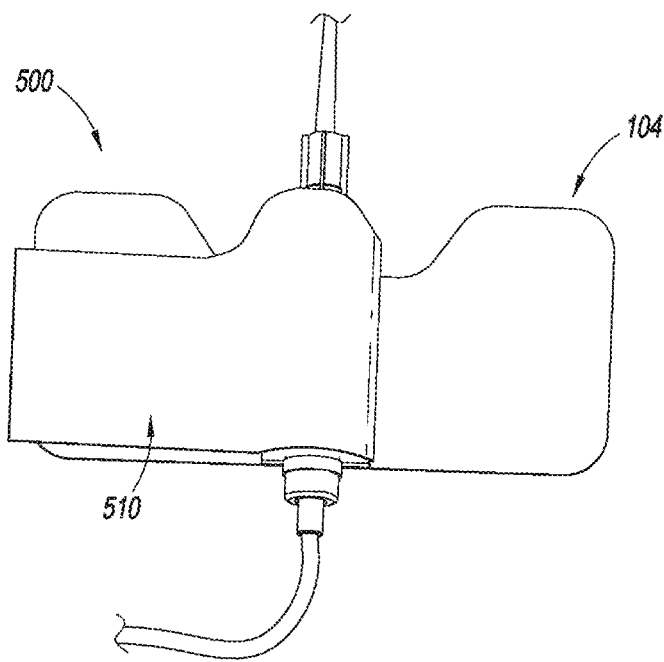
FIG. 41 is a top view of the securement device of FIG. 27 with the flap in the closed position.

Turning to FIGS. 37-38, the liner 513 on the top surface of the flap 510 may be removed by grabbing the pull tab 512 and pulling the liner 513 away from the top surface of the flap 510. In this way, the adhesive surface 516 on the top side of the flap 510 is exposed. As illustrated in FIGS. 39-40, the flap 510 can be folded over the retainer 101 such that a portion of the adhesive surface 516 of the flap 510 covers the spin nut 244 and the retainer 101. The flap 510 may also come into contact with a portion of the anchor pad 104. In this way, the flap 510 further secures the medical article to the patient. FIG. 41 shows a top view of the securement device 500 with the flap 510 in the closed position.

Figure 42:
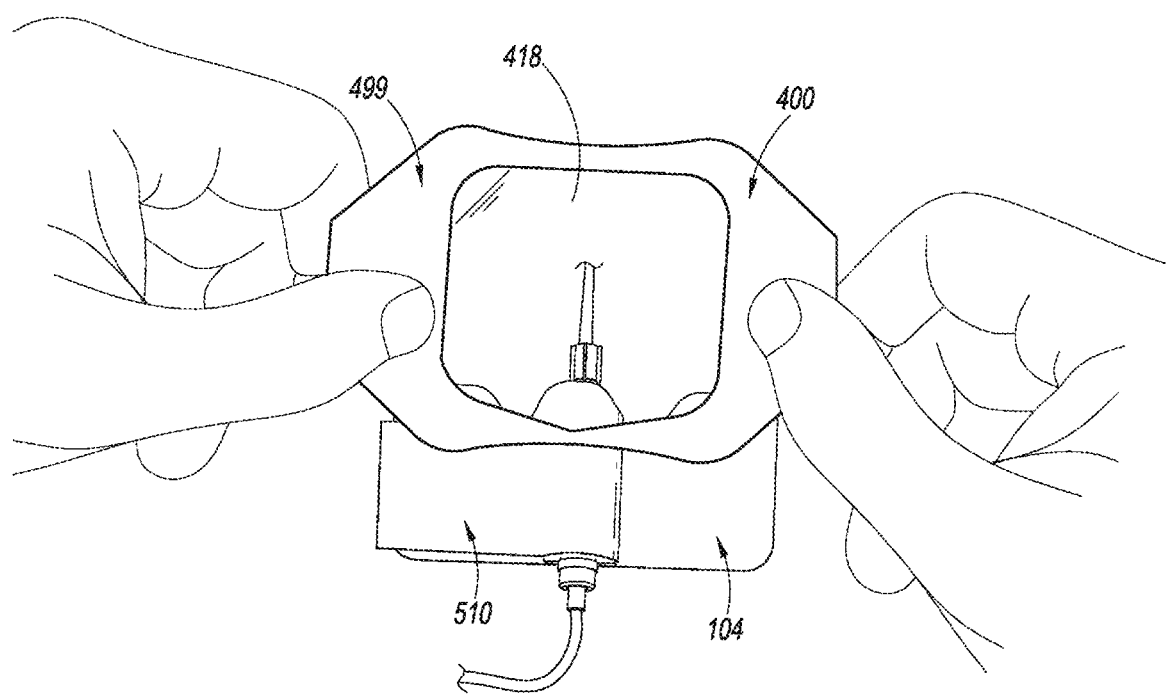
FIGS. 42-43 are top views of a method of using the securement device of FIG. 27. As shown, the method can continue by placing a dressing over the insertion site and at least a portion of the medical article.
Figure 43:
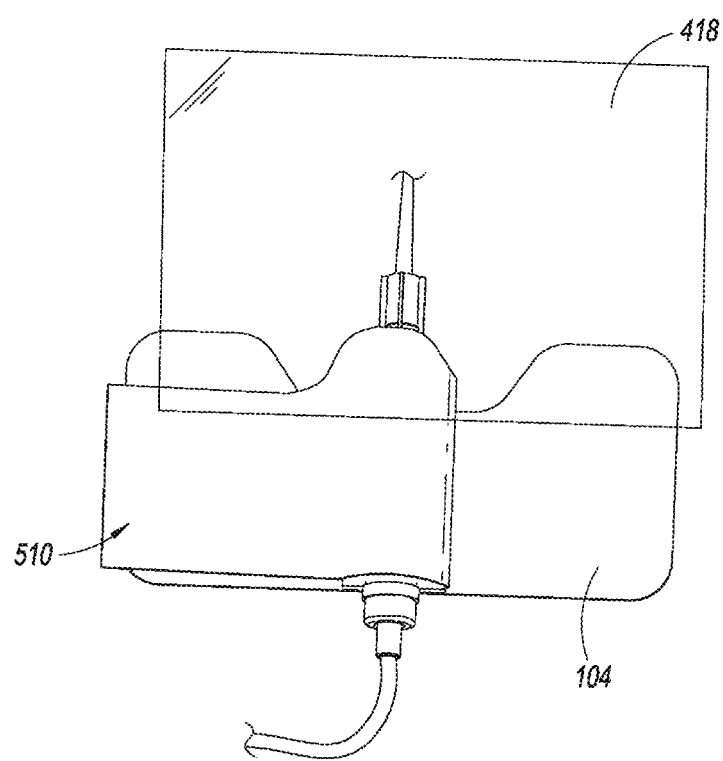

In some embodiments, the process of securing the medical article to the patient may continue by obtaining a dressing 400 as shown in FIG. 42. A liner may be removed from the lower surface of the dressing 400, exposing an adhesive surface on the lower side of the dressing 400. The dressing 400 can then be placed over the insertion site and adhered to the patient with a suitable adhesive surface on the underside of the dressing as shown in FIGS. 42-43. The dressing may include an occlusive layer 418 as described above. As shown in FIG. 43, in some embodiments, the outer perimeter 499 of the dressing may be removed from the occlusive layer 418. In some embodiments, a kit includes the securement device, dressing, and/or tape. The kit may further include instructions for using the kit components.

Figure 44:
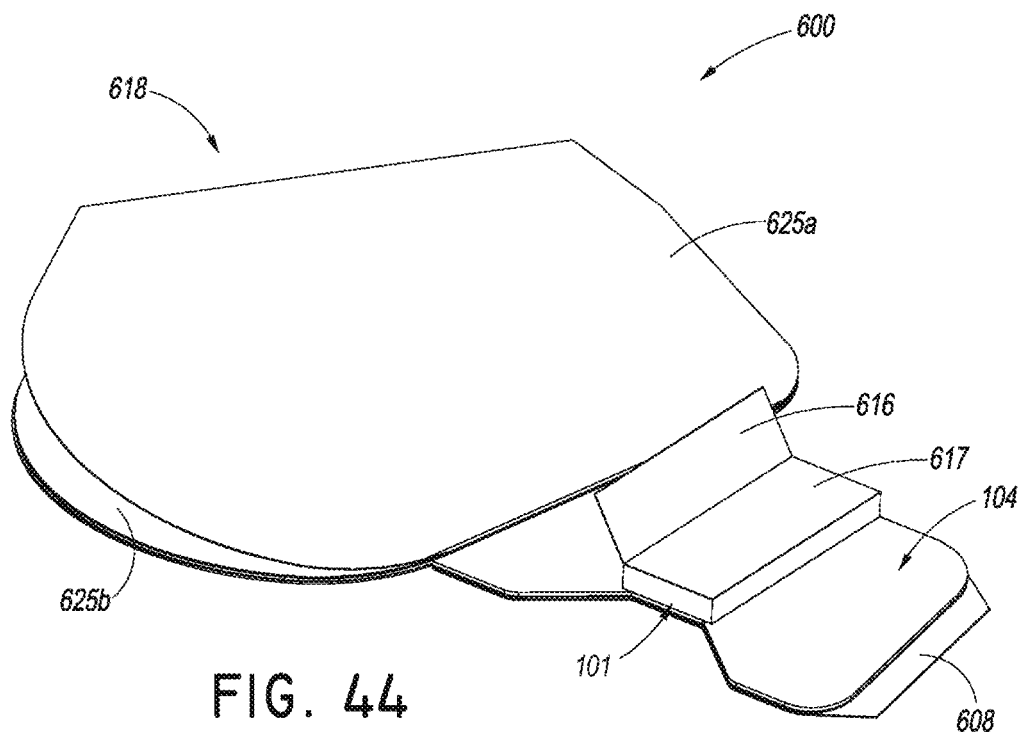
FIGS. 44-45 are perspective views showing a securement system according to another embodiment of the present invention.
Figure 45:
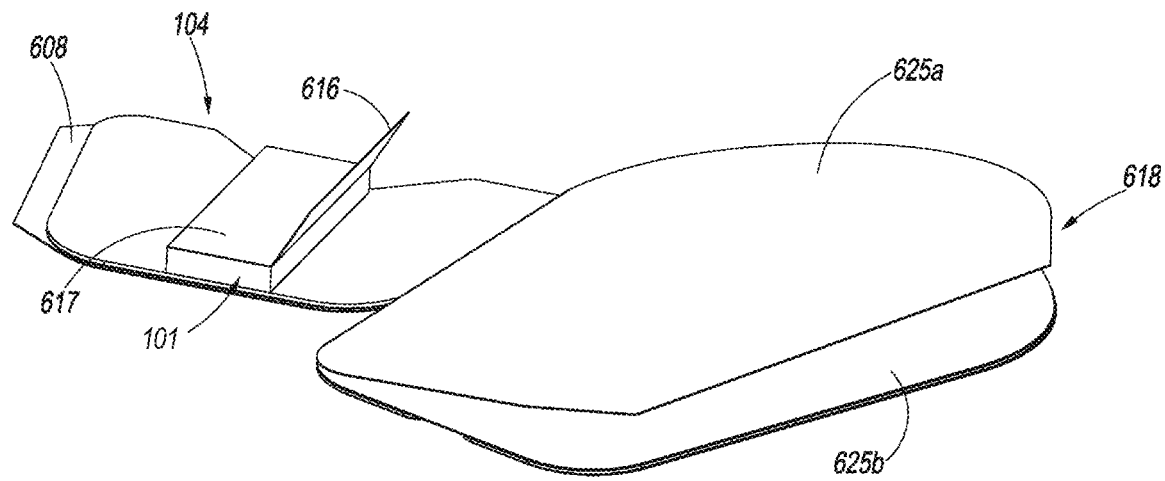
Figure 46:
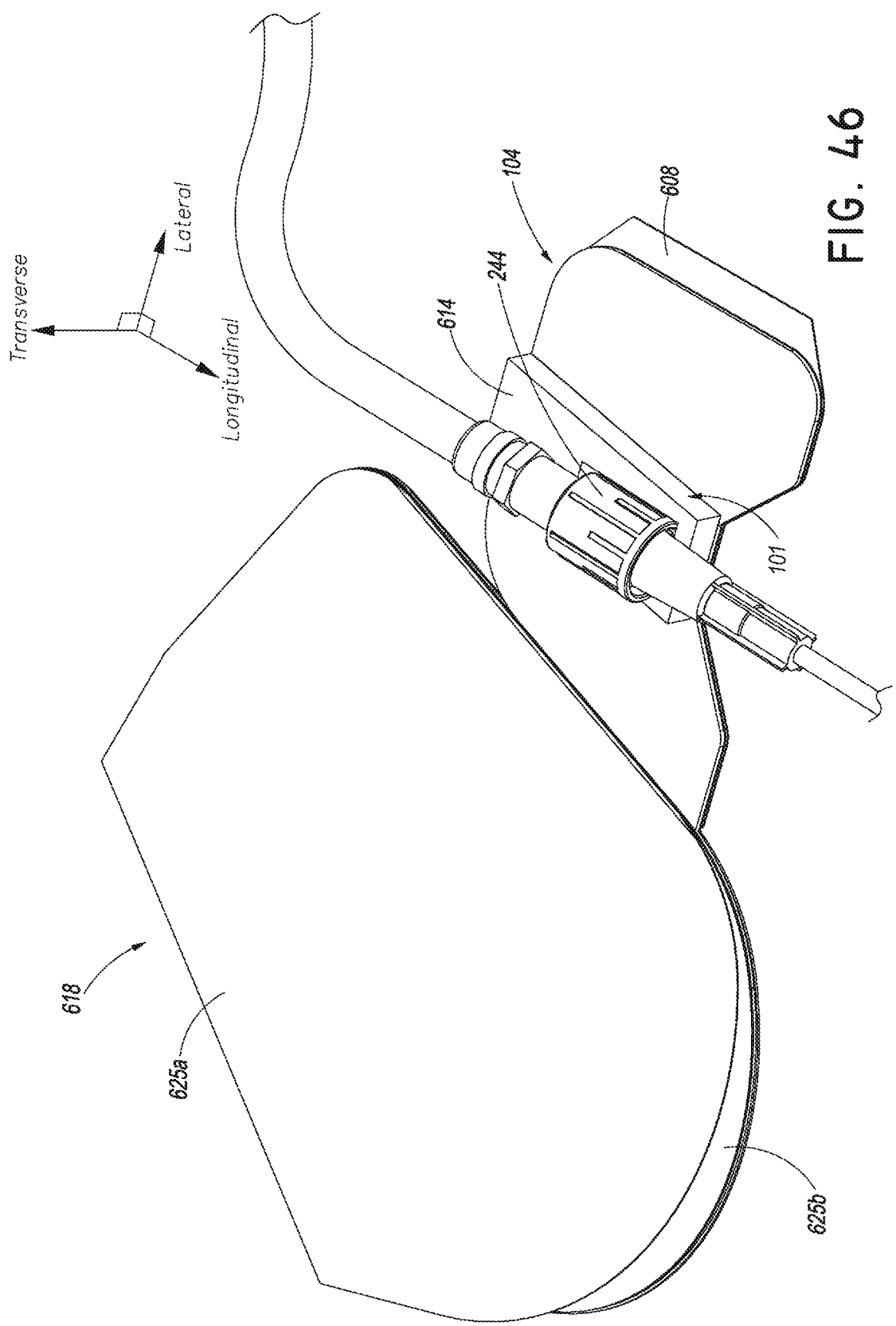
FIG. 46 is another perspective view of the securement device of FIG. 44 and shows a medical article placed in the retainer.

Turning now to FIGS. 44-53, another embodiment of a securement device 600 includes an integral dressing 618, a retainer 101, and an anchor pad 104. The dressing 618 is integral and/or coupled to the anchor pad 104 and the dressing 618 is configured to fold over the insertion site as will be further explained below. As shown, the retainer 101 is covered by liner 617 having a pull tab 616. The top facing side of the dressing 618 is covered by a liner 625*b* disposed over an adhesive surface of the dressing 618. The liner 625*b* includes a fold over section forming pull tab 625*a*. When the liner 625*b* is removed, a medical article 200 that may include a spin nut 244, can be placed within the retainer 101 as shown in FIG. 46. The retainer 101 can include one or more adhesive surfaces.

As illustrated, the retainer 101 may include a recess 108. The retainer 101 may be disposed over an adhesive layer 612 such that the bottom surface of the recess 108 in the retainer 101 includes an adhesive surface. The adhesive layer 612 may also function to secure the retainer to the anchor pad 104. The adhesive layer 612 may be disposed on the anchor pad 104. Adhesive layer 614 may be disposed on the uppermost surface of the retainer 101 and may be covered by the removable liner 617.

Figure 47:
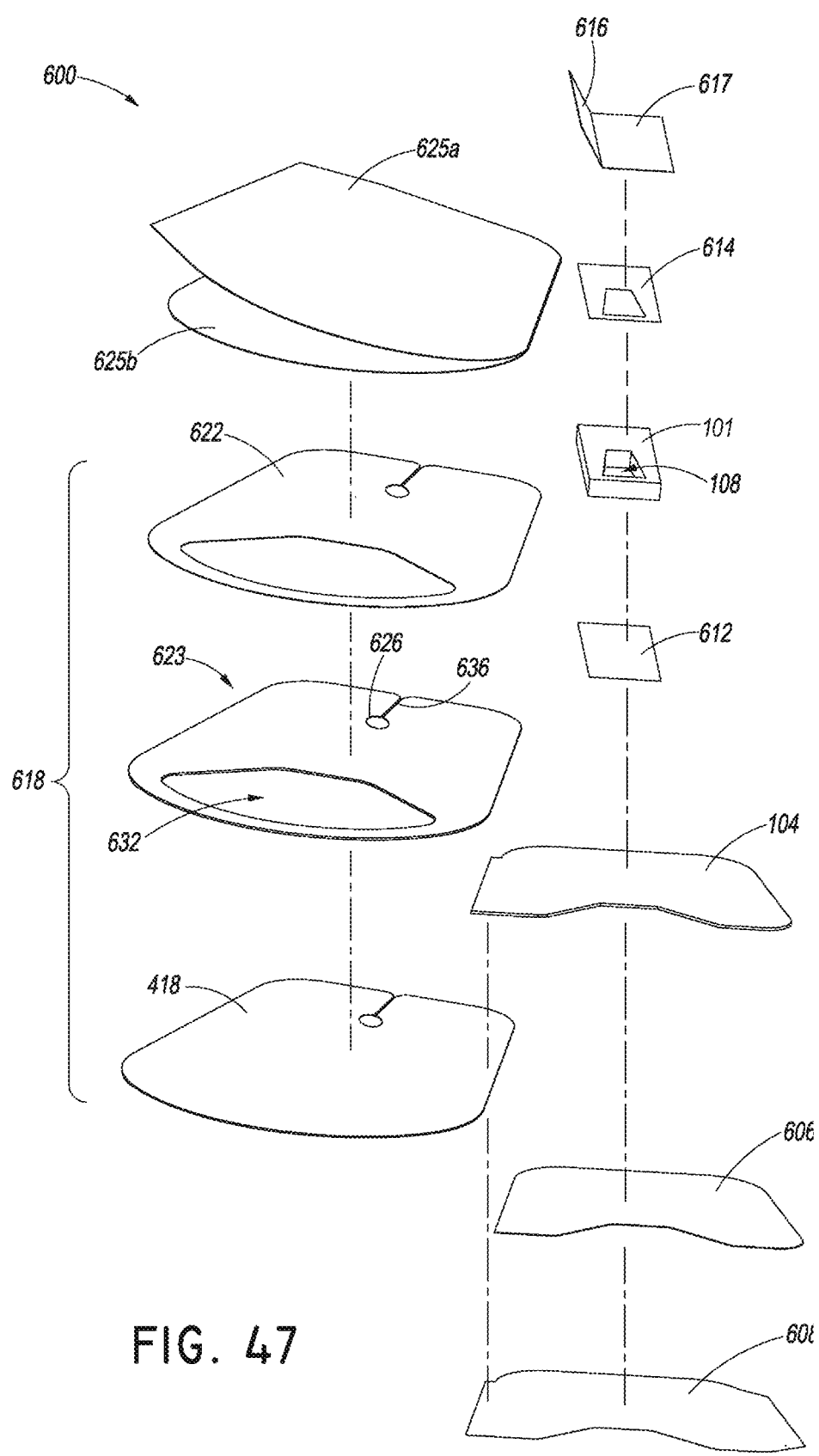
FIG. 47 is an exploded view of the securement device of FIG. 44.

Turning to the dressing 618, as shown in FIG. 47, the dressing 618 can include an adhesive layer 622, a pad 623, and an occlusive layer 418. As shown in FIG. 47, the adhesive layer 622 can be disposed on the top side of the pad 623 and the occlusive layer 418 may be disposed on the underside of the pad 623. The adhesive layer 622 may cover all or a portion of the topside of the pad 623.

The dressing 618 can include an opening 626 configured such that a medical article can pass through the opening 626 when the dressing 618 is folded over to cover the insertion site and the medical article. The dressing 618 can also include a slot 636. The slot 636 can be sized and shaped such that a portion of the medical article can pass through the slot 636. The pad 623 can include a window 632. The window 632 can allow for the insertion site to be observed without removing the dressing 618. The adhesive layer 620 may be covered by liner 625*b* having a pull tab 625*a*. As shown, the liner 625*b* is generally the same size and shape as the pad 623 but does not include an opening or slot.

Figure 48:
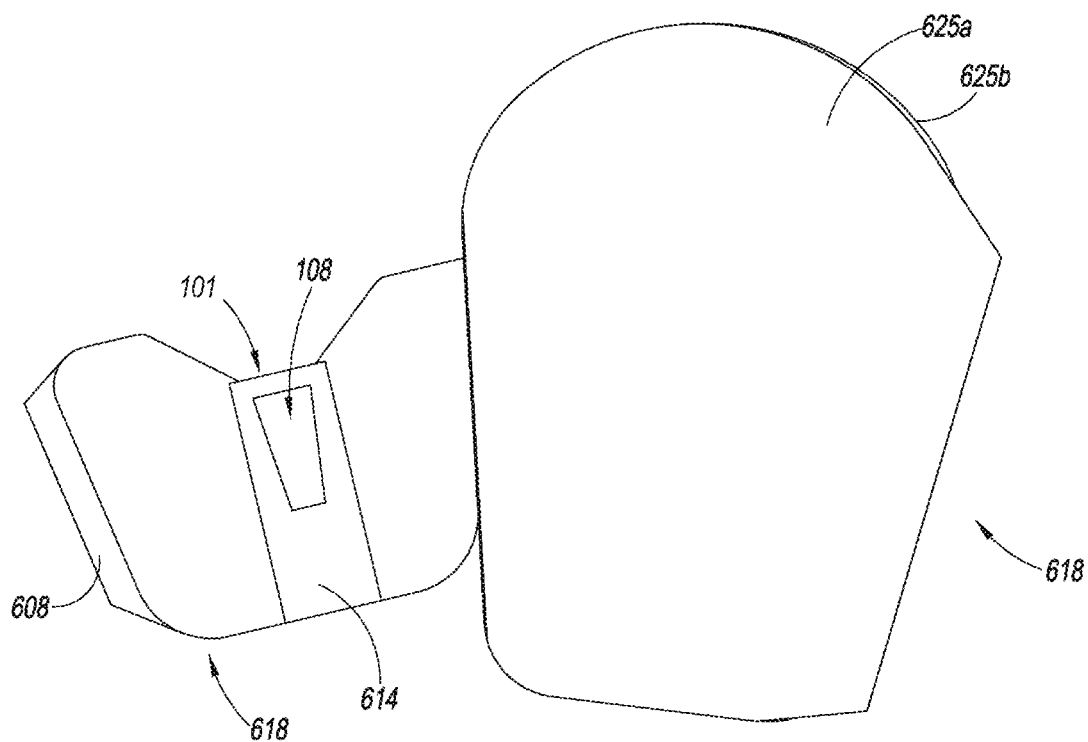
FIG. 48 is a perspective view of a method of using the securement device of FIG. 44. As shown, the method can begin by removing a liner disposed over the retainer.

In operation, a method of using the securement device 600 and a process for coupling a medical article to a patient can begin by rotating the dressing 618 away from the anchor pad 104 so as to unfold the securement device 600 as shown in FIGS. 44-45. A user may then grab pull tab 616 and remove the liner 617 (as shown in FIG. 47) from the retainer, thus exposing the adhesive layer 614 as shown in FIG. 48.

Figure 49:
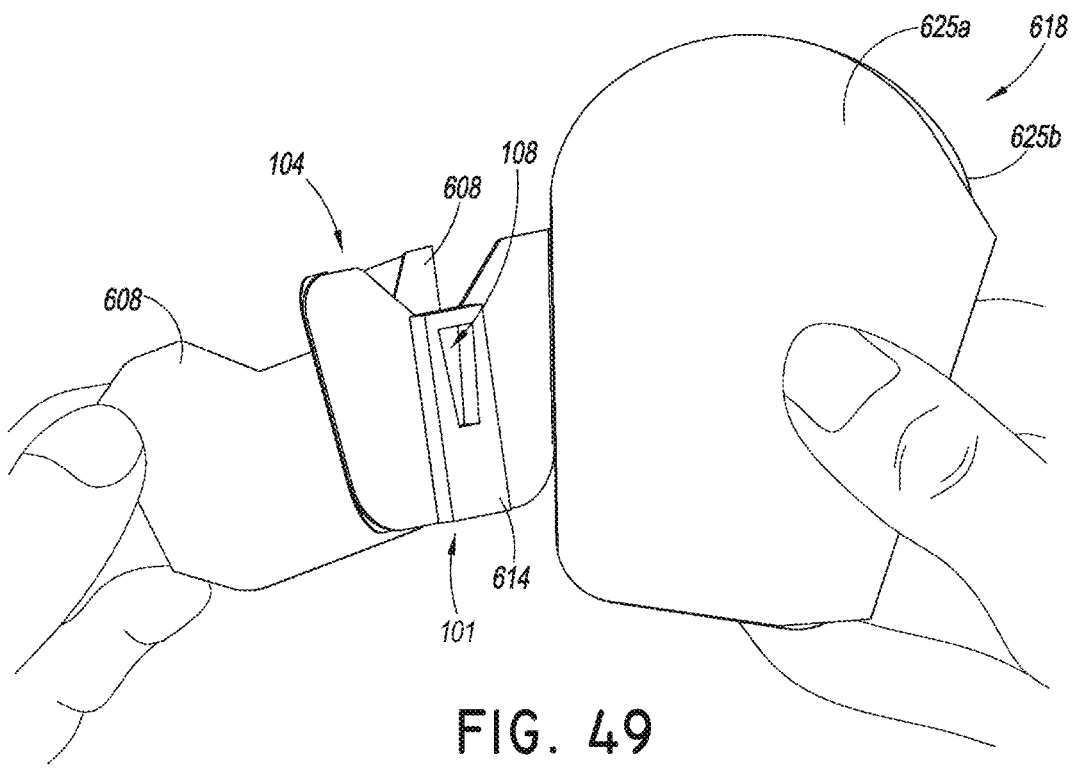
FIG. 49 is a perspective view of a method of using the securement device of FIG. 44. As shown, the method can continue by removing a liner on a lower surface of an anchor pad.
Figure 50:
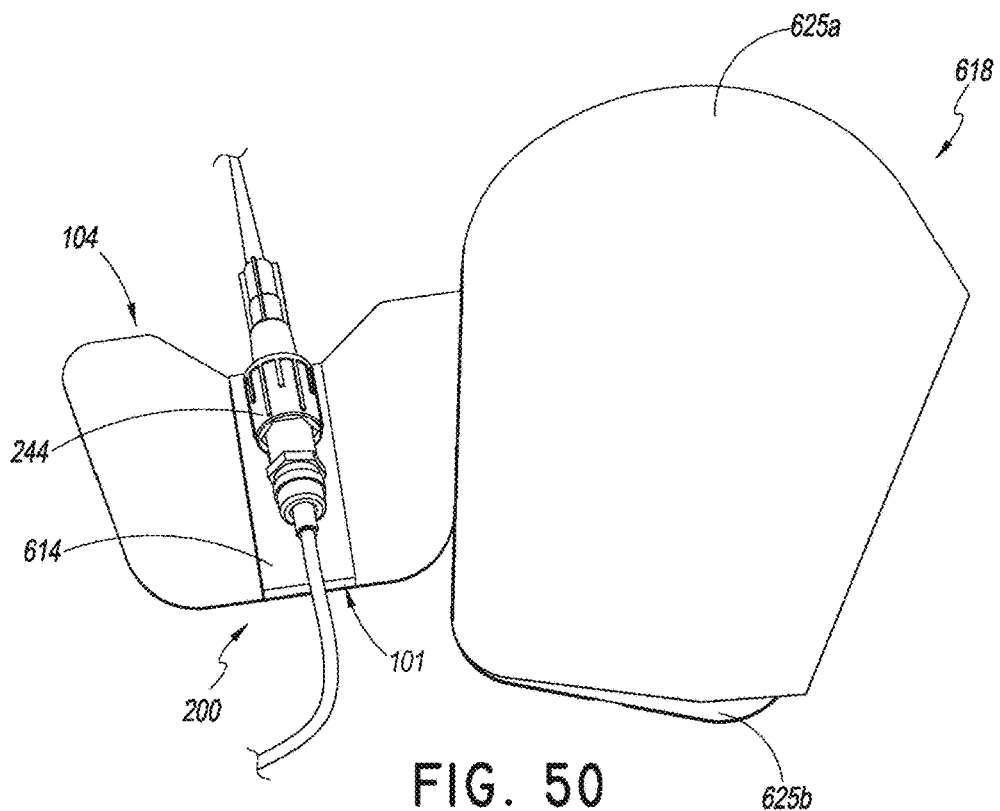
FIG. 50 is a top view of a method of using the securement device of FIG. 44. As shown, the method can continue by placing a medical article within the retainer.
Figure 51:
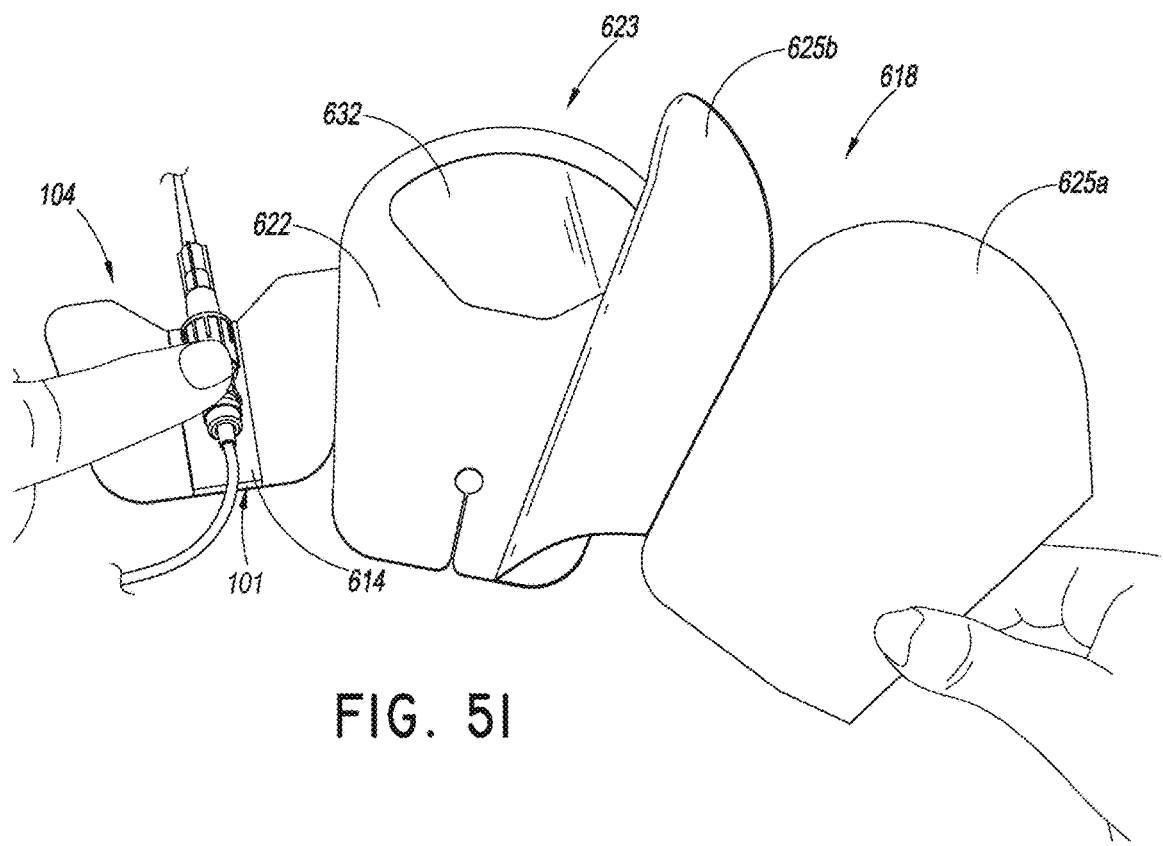
FIGS. 51-53 are top views of a method of using the securement device of FIG. 44. As shown, the method can continue by removing a liner from a dressing and then folding the dressing over the medical article. The medical article passes through a slot in the dressing.
Figure 52:
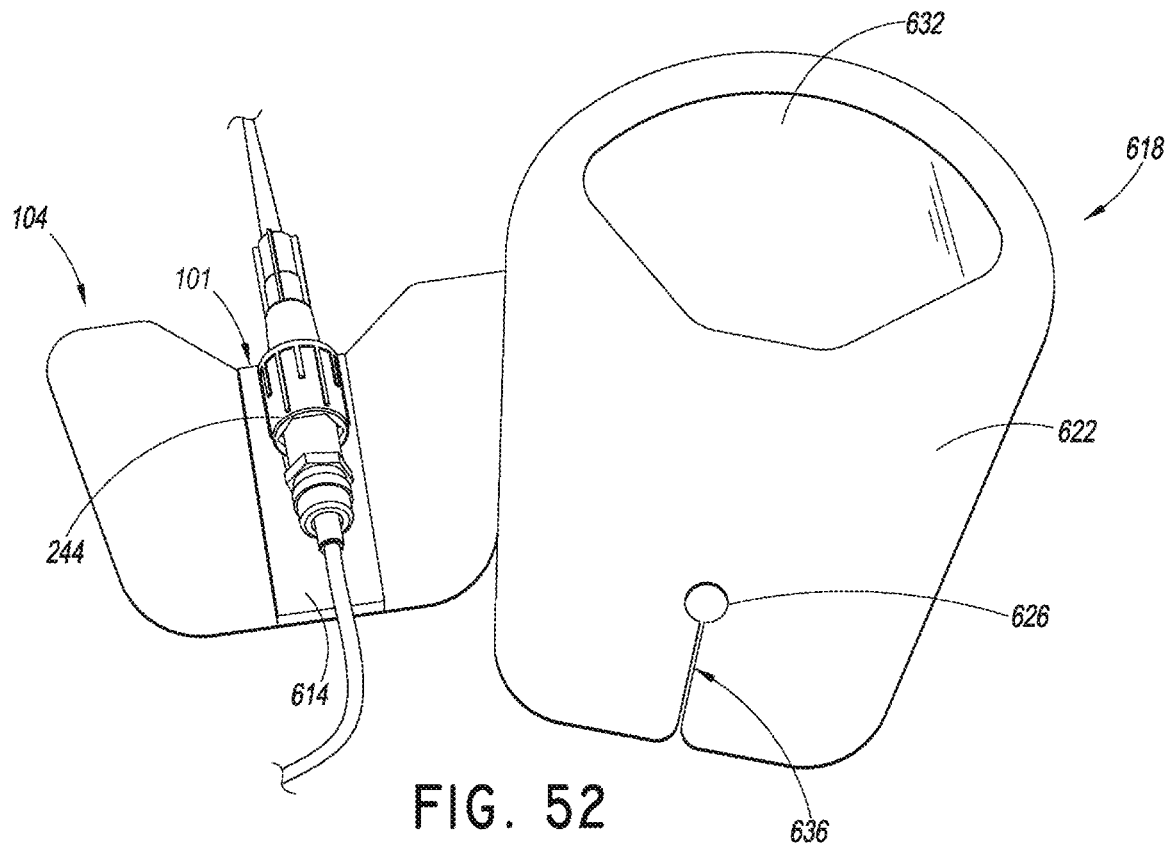
Figure 53:
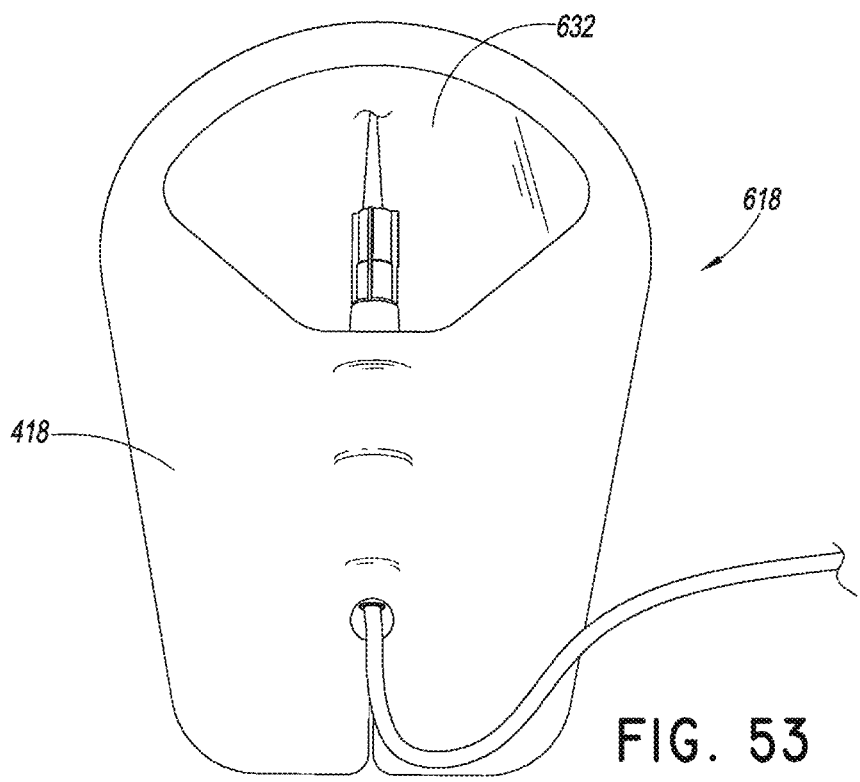

The process can continue by removing the liner 608 covering the lower adhesive surface of the anchor pad 104 as shown in FIG. 49, thus exposing the adhesive layer. The process can continue by placing a medical article 200 having a spin nut 244 into the recess 108 of the retainer 101 as shown in FIG. 50 and placing the adhesive layer of the anchor pad on the patient's skin. Thus, the medical article 200 can be placed into contact at least one adhesive surface of the retainer 101 and the securement device is secured to the patient. Turning to FIG. 51, the process can continue by grabbing the pull tab 625*a* on the dressing and removing the liner 625*b* by pulling the pull tab 625*a* away from the dressing 618. In this way, the adhesive layer 622 of the dressing 618 is exposed as shown in FIG. 52. As shown in FIG. 53, the dressing 618 can then be folded over the anchor pad 104, retainer 101, medical article, and insertion site. In this way, the dressing 618 is secured to the patient's skin.

Moving to FIGS. 54-68, another embodiment of a securement device 700 includes a flap 708, a retainer 101, and an anchor pad 104. In certain embodiments, the flap 708 is a portion of the anchor pad 104. The anchor pad may include a folding line 789. In such an embodiment, the portion of the anchor pad which folds over the retainer 101 is the flap 708. The folded portion of the anchor pad attaches to another portion of the anchor pad. In this way a first portion of the anchor pad is adhered to a second portion of the anchor pad.

The retainer 101 includes a recess 108 and one or more adhesive surfaces. The retainer 101 is supported the anchor pad 104. The anchor pad 104 is generally rectangular shaped and includes a generally circular opening 710 having a slot 712. The slot 712 is configured to allow a portion of a medical article to pass through the slot 712 and into the opening 710 of the anchor pad 104 as will be discussed below. At least a portion of the lower surface 106 of the anchor pad 104 can include an adhesive.

Figure 56:
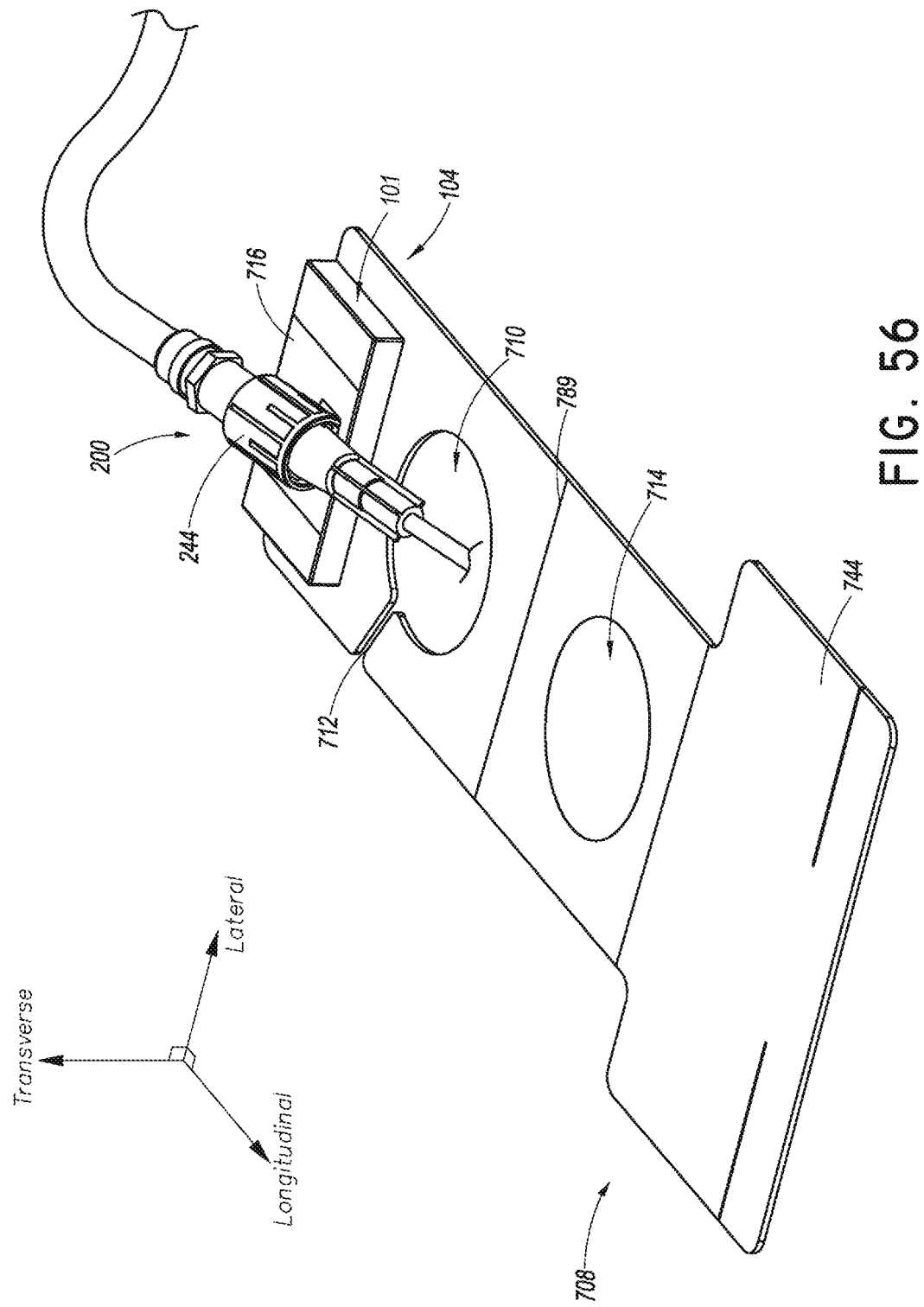
FIG. 56 is another perspective view of the securement device of FIG. 54 and shows a medical article placed in the retainer before a portion of the anchor pad or flap is folded over the medical article.
Figure 57:
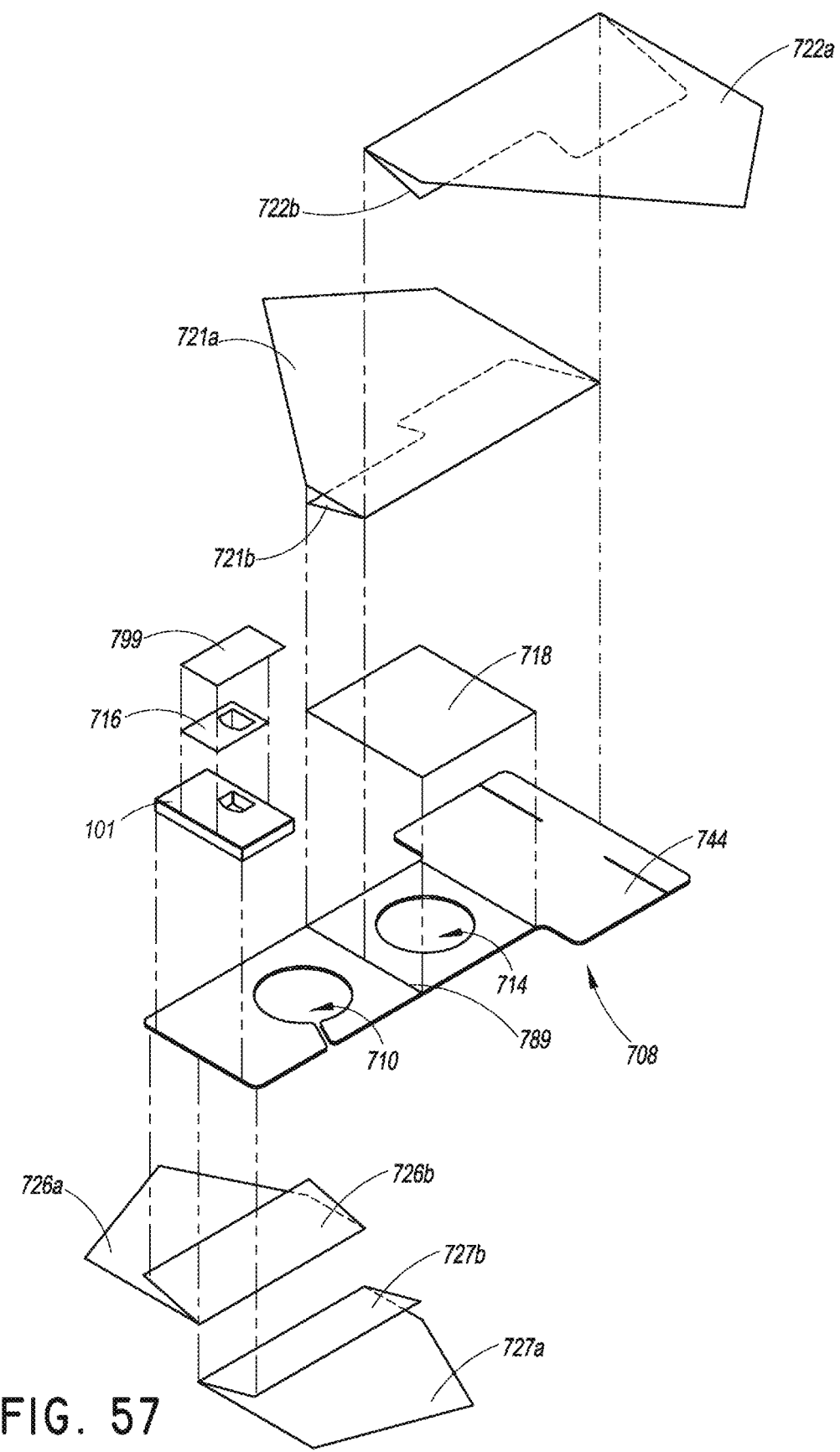
FIG. 57 is an exploded view of the securement device of FIG. 54.
Figure 58:
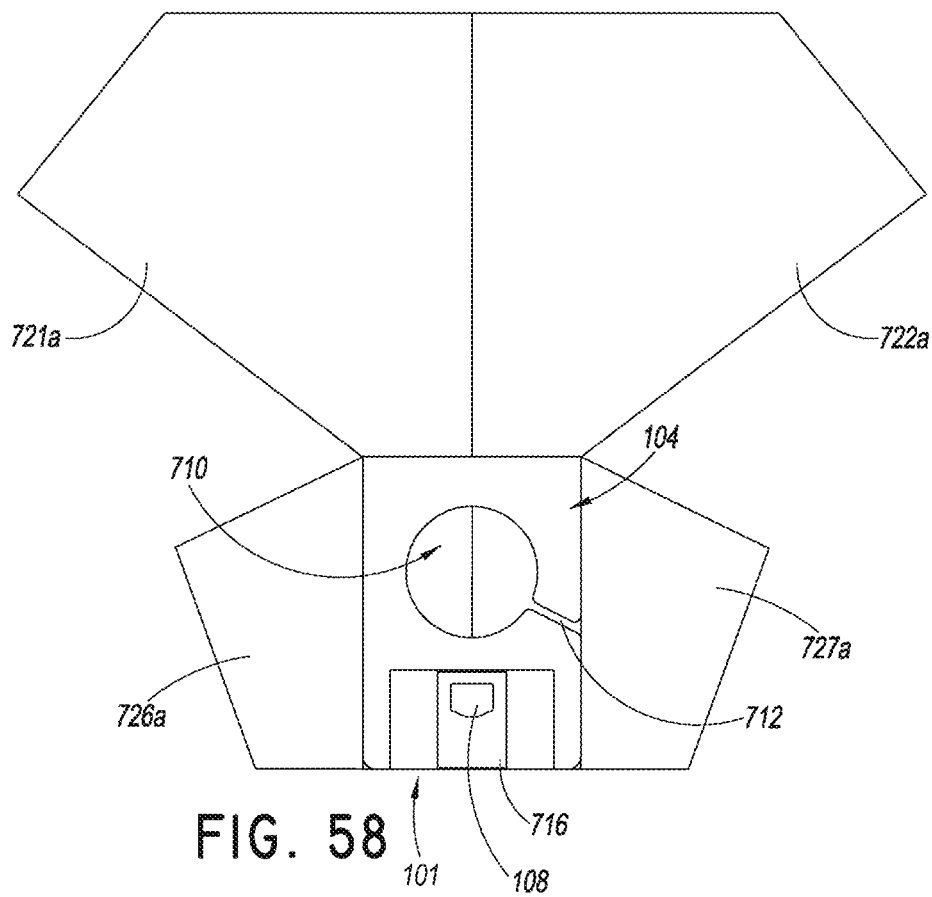
FIG. 58 is a top view of the securement device of FIG. 54 including release liners on the lower surfaces of the device.
Figure 59:
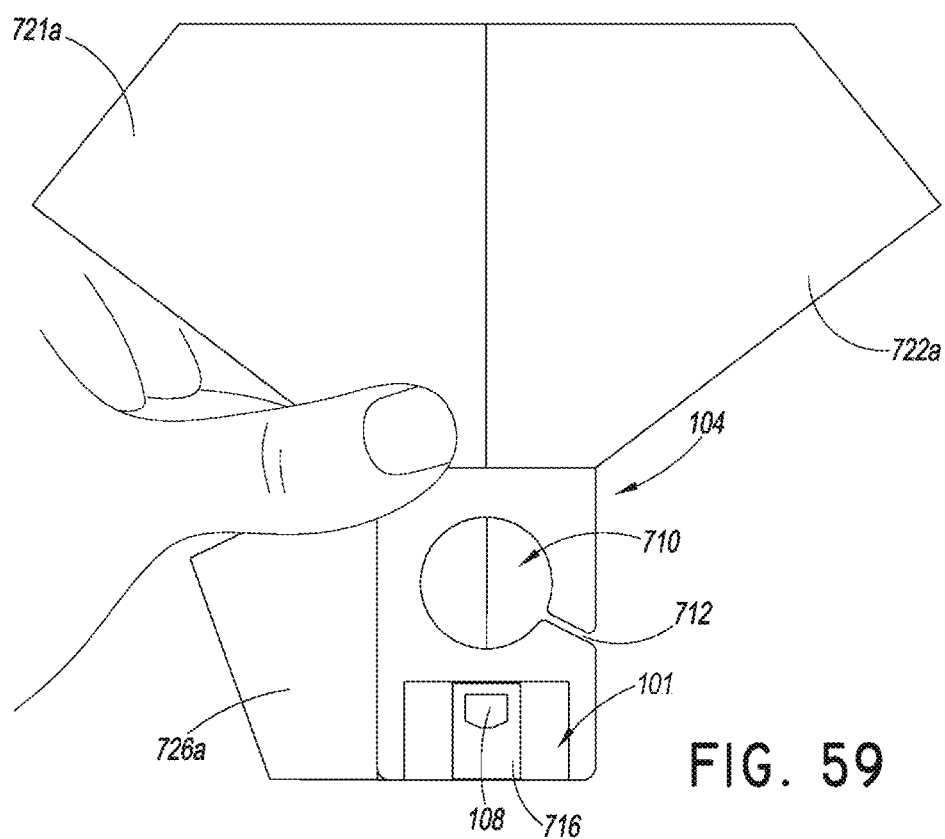
FIG. 59 is a top view of a method of using the securement device of FIG. 54. As shown, the method can begin by removing a liner covering a lower surface of the anchor pad.

The flap 708 or portion of the anchor pad 104 is configured to move, rotate, and/or fold over another portion of the anchor pad 104. The flap 708 includes a window 714. The window 714 is generally sized and shaped the same as the opening 710 in the anchor pad 104. The window 714 in the flap 708 may be covered by a transparent or translucent film. The top side of the flap 708, as shown in FIGS. 54-55 may include an adhesive surface 744. The adhesive surfaces of the retainer 101, anchor pad 104, and/or flap 708 may further be covered by one or more liners. For example, as shown in FIG. 57, a liner 799 may cover the adhesive surface 716 of the retainer 101. As shown in FIG. 56, a medical article 200 having a spin nut 244 may be placed in the recess 108 in the retainer 101. The opening 710 in the anchor pad 104 generally surrounds the catheter insertion site. The flap 708 may be folded over the anchor pad 104 such that the retainer 101, anchor pad 104, and/or the medical article 200 are contacted by the flap 708.

FIG. 57 is an exploded view of the securement device 700. An adhesive layer 716 may be disposed on a top surface of the retainer 101. The retainer 101 may be disposed on the anchor pad 104. The adhesive layer on the underside of the anchor pad may be covered by removable liners 726b and 727b having folder over sections forming pull tabs 726a and 727a. The flap 708 includes a film 718 disposed over the window 714. An adhesive layer 744 may be disposed on the top side of the flap 708 such that when the flap 708 is folded over the medical article, the adhesive layer 744 can adhere to the medical article securing the flap 708 in the closed position. The adhesive layer 744 may be covered by removable liners 721b and 722b having folder over sections forming pull tabs 721a and 722a.

In operation, a method of using the securement device 700 and a process for coupling a medical article to a patient can begin by removing the liners 726a and 727b having pull tabs 726a and 727a from the underside of the anchor pad 104 as shown in FIGS. 58-61. In general, each liner covers approximately half of the underside of the anchor pad 104. More or less liners may be used in any number of configurations. As shown, in FIG. 59, the left hand side liner 727b and pull tab 727a (i.e. the liner covering the underside of the slot side of the anchor pad 104) is removed exposing the adhesive layer on the underside of the anchor pad 104.

Figure 60:
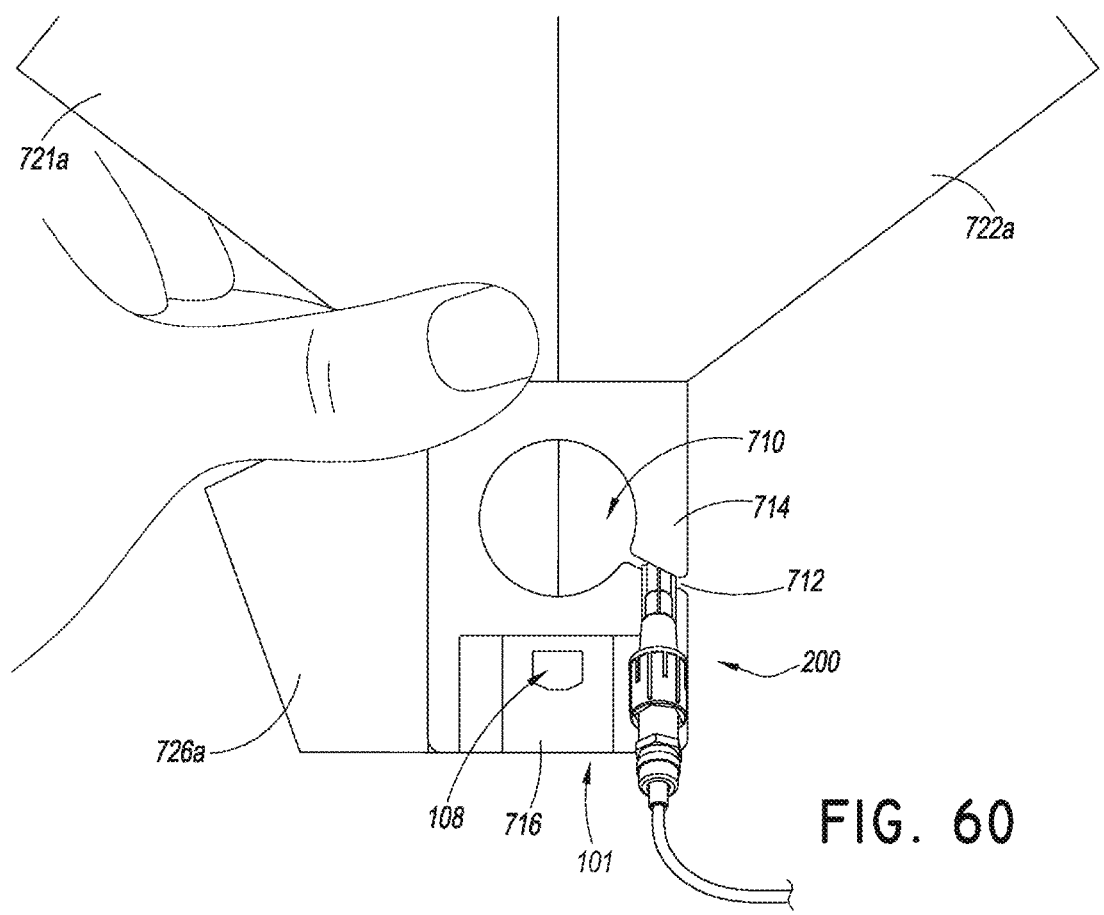
FIG. 60 is a top view of a method of using the securement device of FIG. 54. As shown, the method can continue by sliding the securement device between the patient's skin and the medical article while guiding the medical article through a slot in the securement device.
Figure 61:
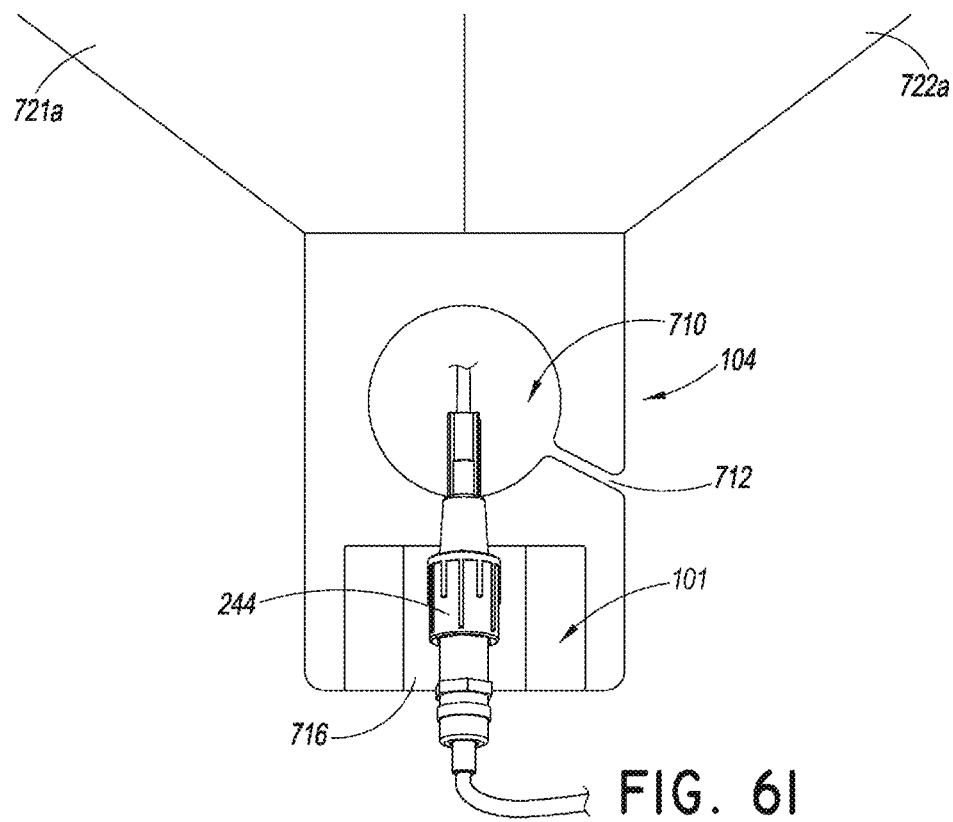
FIG. 61 is a top view of a method of using the securement device of FIG. 54. As shown, the method can continue by removing a second liner on a lower surface of the anchor pad.
Figure 62:
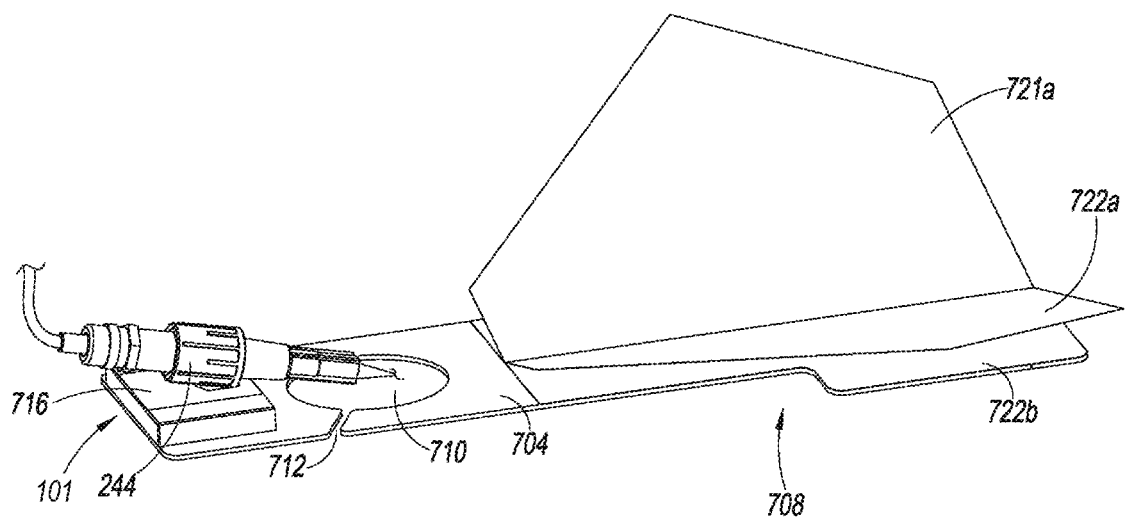
FIG. 62 is a perspective view of the securement device of FIG. 54 secured to a patient.
Figure 63:
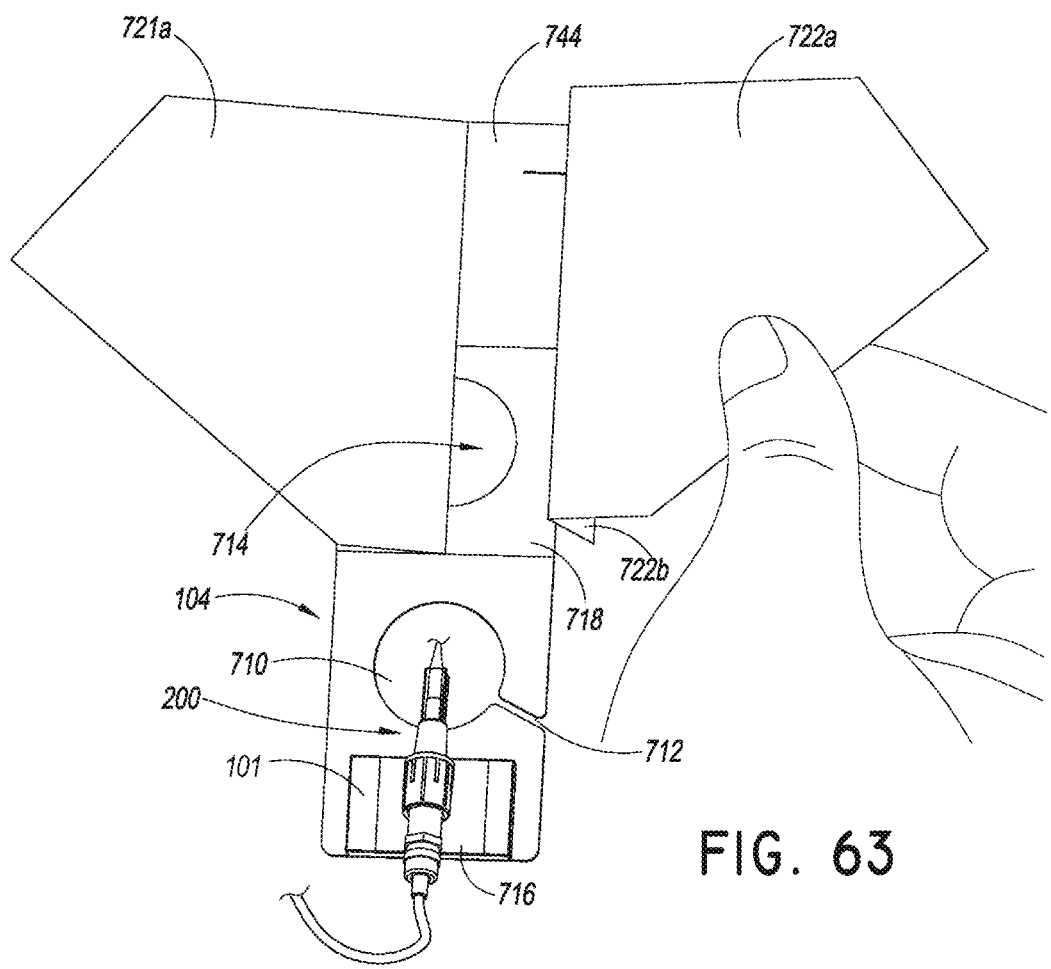
FIGS. 63-65 are top views of a method of using the securement device of FIG. 54. As shown, the method can continue by removing the liners from the flap.
Figure 64:
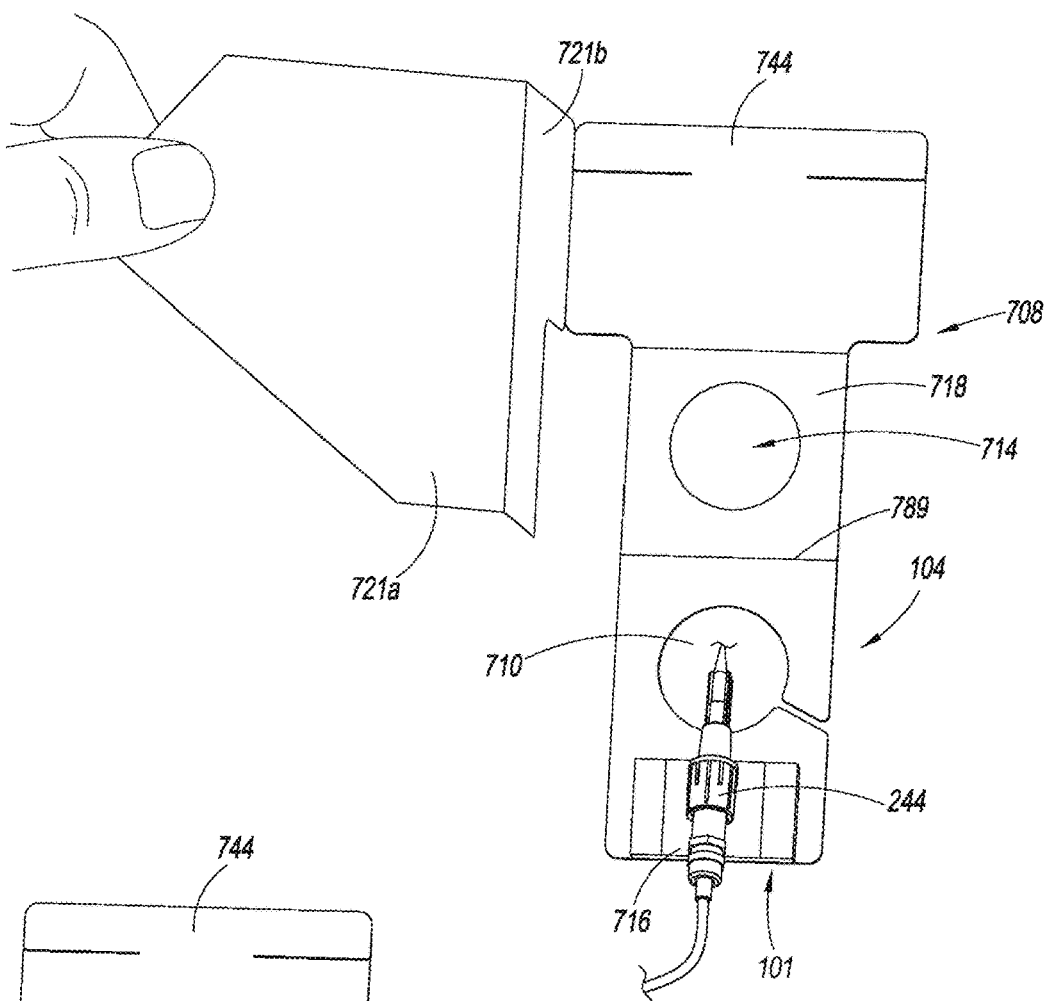
Figure 65:
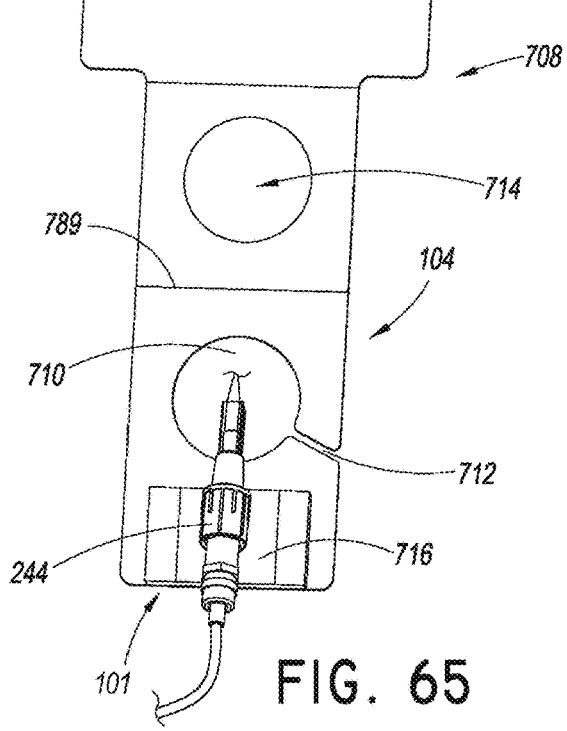

The process can continue by positioning the securement device 700 such that a medical article is passed through the slot 712 and into the opening 710 of the anchor pad 104 as shown in FIG. 60. The retainer 101 of the securement device 700 can be positioned such that the spin nut 244 of the medical article is positioned above the retainer 101 and made to contact at least one adhesive surface of the retainer 101. The second liner 726b and pull tab 726a can then be removed from the underside of the anchor pad 104 as shown in FIG. 61. Thus, the securement device 700 is secured to a patient's skin. As shown in FIG. 62, in some embodiments, the retainer 101 is configured to suspend the spin nut 244 above the skin of a patient at an angle relative to the skin of the patient, for example, 7 degrees.

Figure 66:
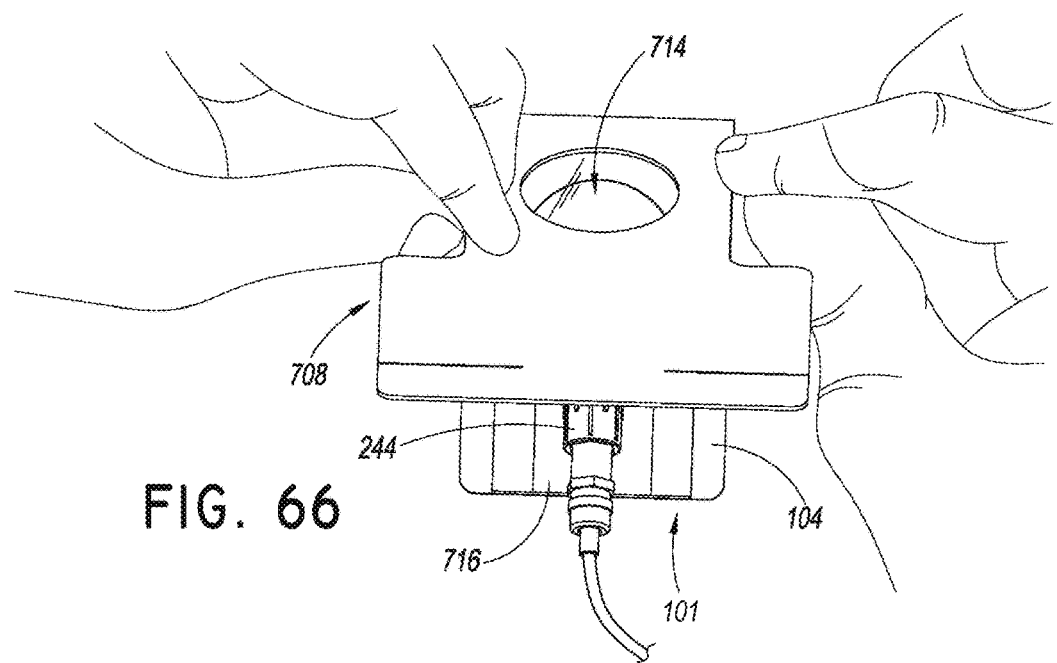
FIGS. 66-67 are top views of a method of using the securement device of FIG. 54. As shown, the method can continue by folding the flap over the medical article.
Figure 67:
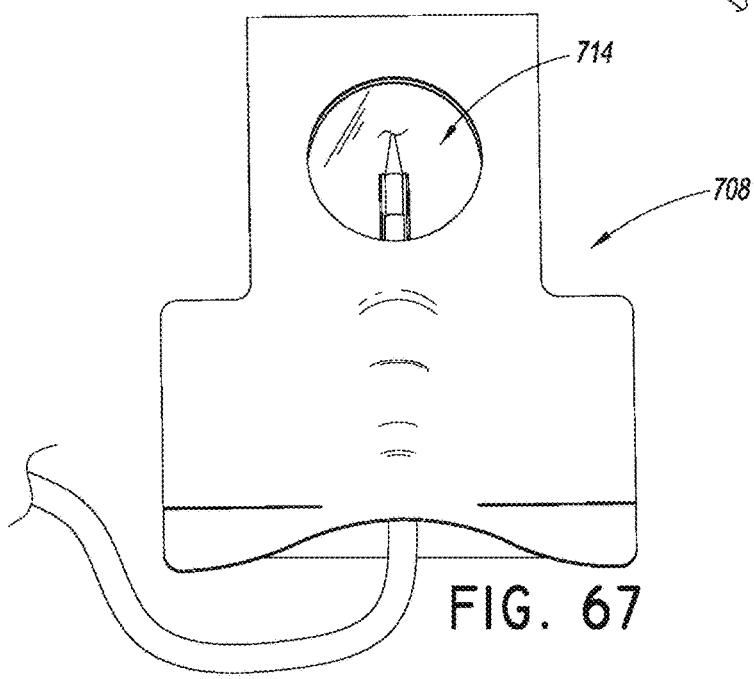
Figure 68:
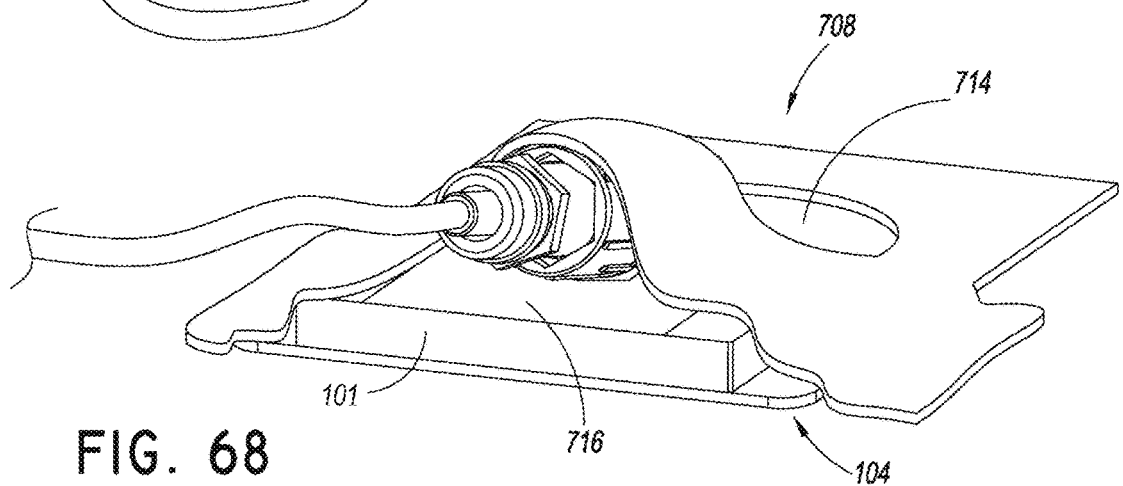
FIG. 68 is a rear perspective view of the securement device of FIG. 54 showing the medical article secured in the securement device.

The process continues in FIGS. 62-65 by removing the liners 721b and 722b and pull tabs 721a and 722a from the flap 708 to expose the adhesive surface 744. The flap 708 is then folded over the anchor pad 104, retainer 101, and medical article 200 as shown in FIGS. 66-68. In this way, the medical article is secured to the patient's skin.

Turing to FIGS. 69-79, another embodiment of a securement device 700 includes a retainer 101 and an anchor pad 104. The illustrated embodiment of the retainer 101 does not include a recess as described above but rather at least a portion of the top surface of the retainer 101 includes an adhesive 808. The retainer 101 is configured to secure a medical article at an angle. As shown, the top surface is at an angle θ. A variety of different angles θ can be used, ranging from 0 degrees to 45 degrees or from 5 degrees to 25 degrees. For instance, for the securement of intravenous catheters, it is desirable for the angle of incidence of the catheter to the skin of the patient to be between about 7 degrees to about 15 degrees. For the securement of arterial catheters, it is desirable for the angle of incident of the catheter to the skin of the patient to be about 12.5 degrees. By angling the top surface of the retainer 101 at the desired angle, which will depend upon the particular securement application (e.g., securing an arterial catheter, an intravenous catheter, etc.), the proper angle of incidence for a catheter can be maintained.

Figure 69:
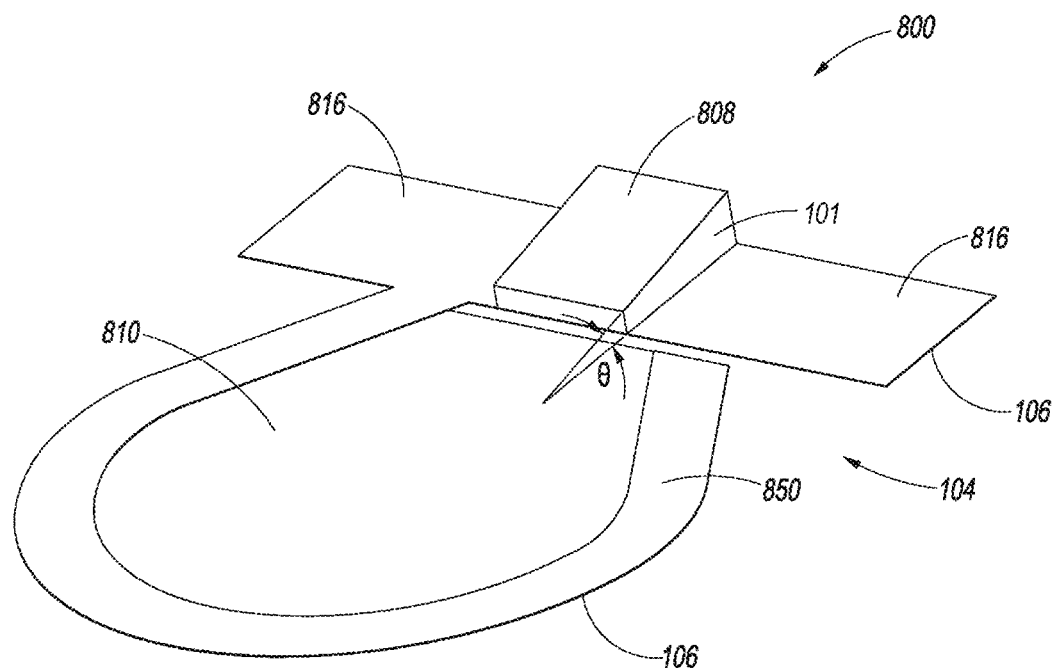
FIGS. 69-70 are perspective views of a securement device according to another embodiment of the present invention.
Figure 70:
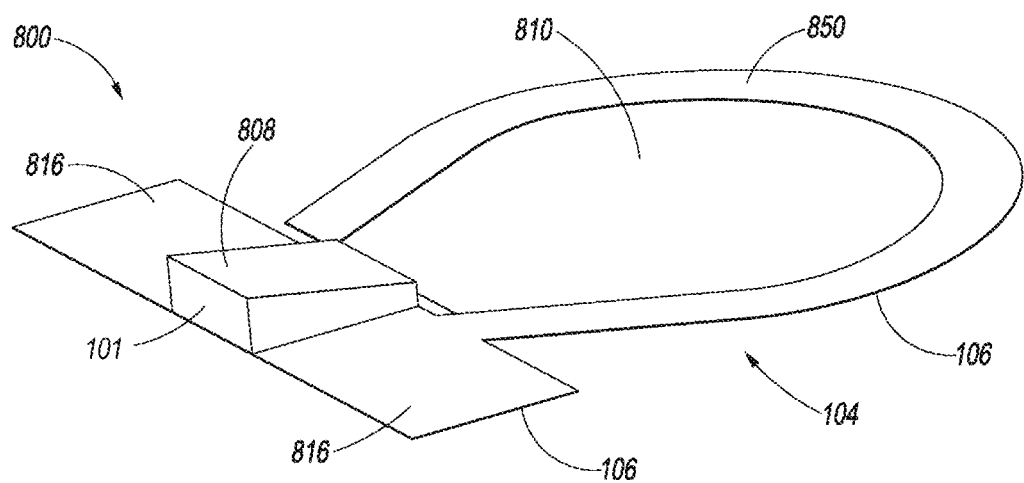
Figure 71:
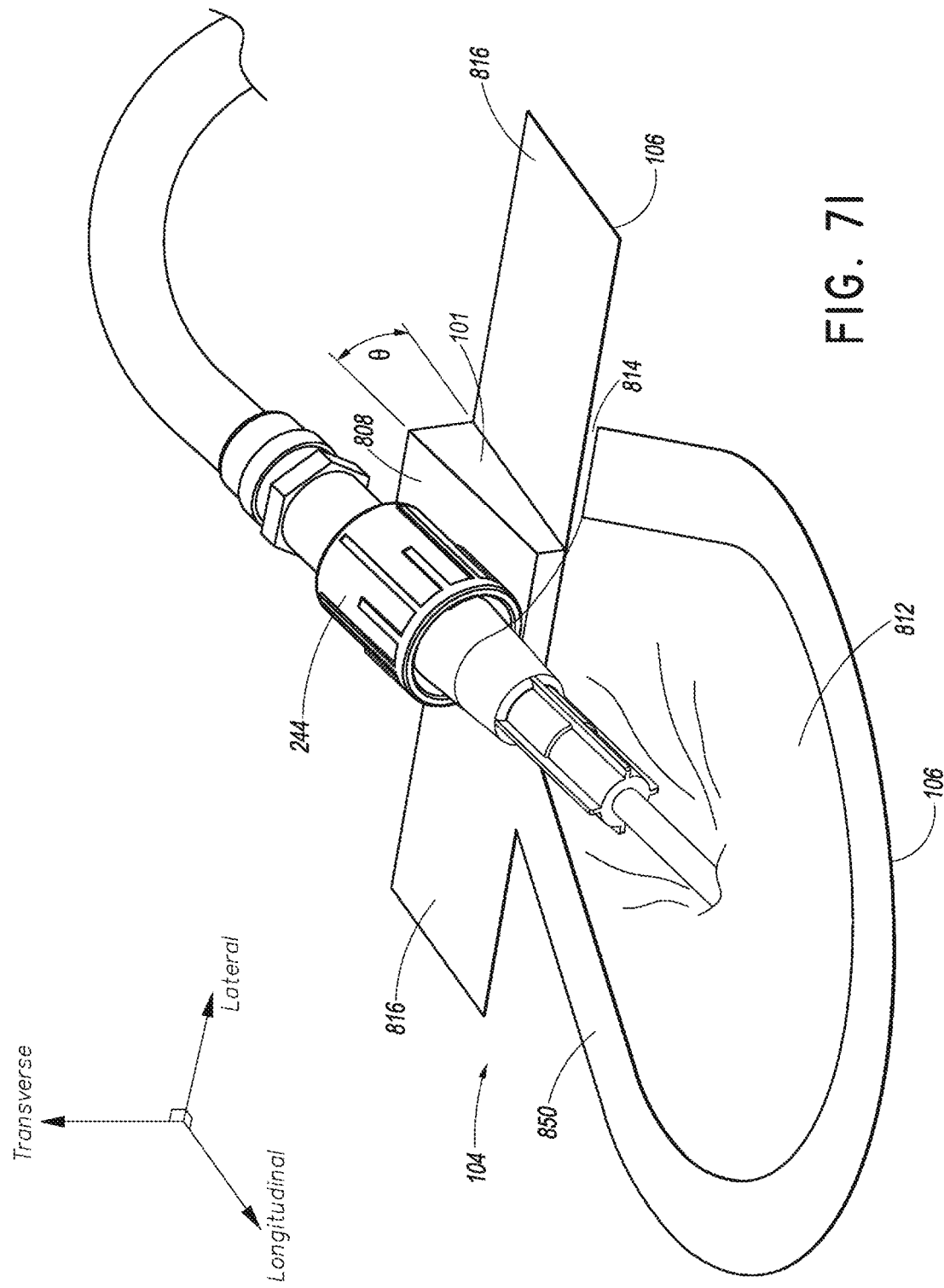
FIG. 71 is another perspective view of the securement device of FIG. 69 and shows a medical article placed on the retainer and with an integral dressing covering an insertion site.

As shown in FIGS. 69-71, the anchor pad 104 is shaped to include two wing portions 816 configured to support the retainer 101 and a loop portion 850 configured to generally surround the insertion site of the medical article and frame a film 812. The underside of the anchor pad 104 may include an adhesive layer.

As shown in FIG. 71, a medical article 200 having a spin nut 244 may be placed on the top surface of the retainer 101. The loop portion 850 of the anchor pad 104 generally surrounds the insertion site. The loop portion 850 of the anchor pad 104 frames a film 812. The anchor pad 104 can also include a slot 814. The slot 814 can be sized and shaped such that a medical article can pass through the slot 814.

Figure 72:
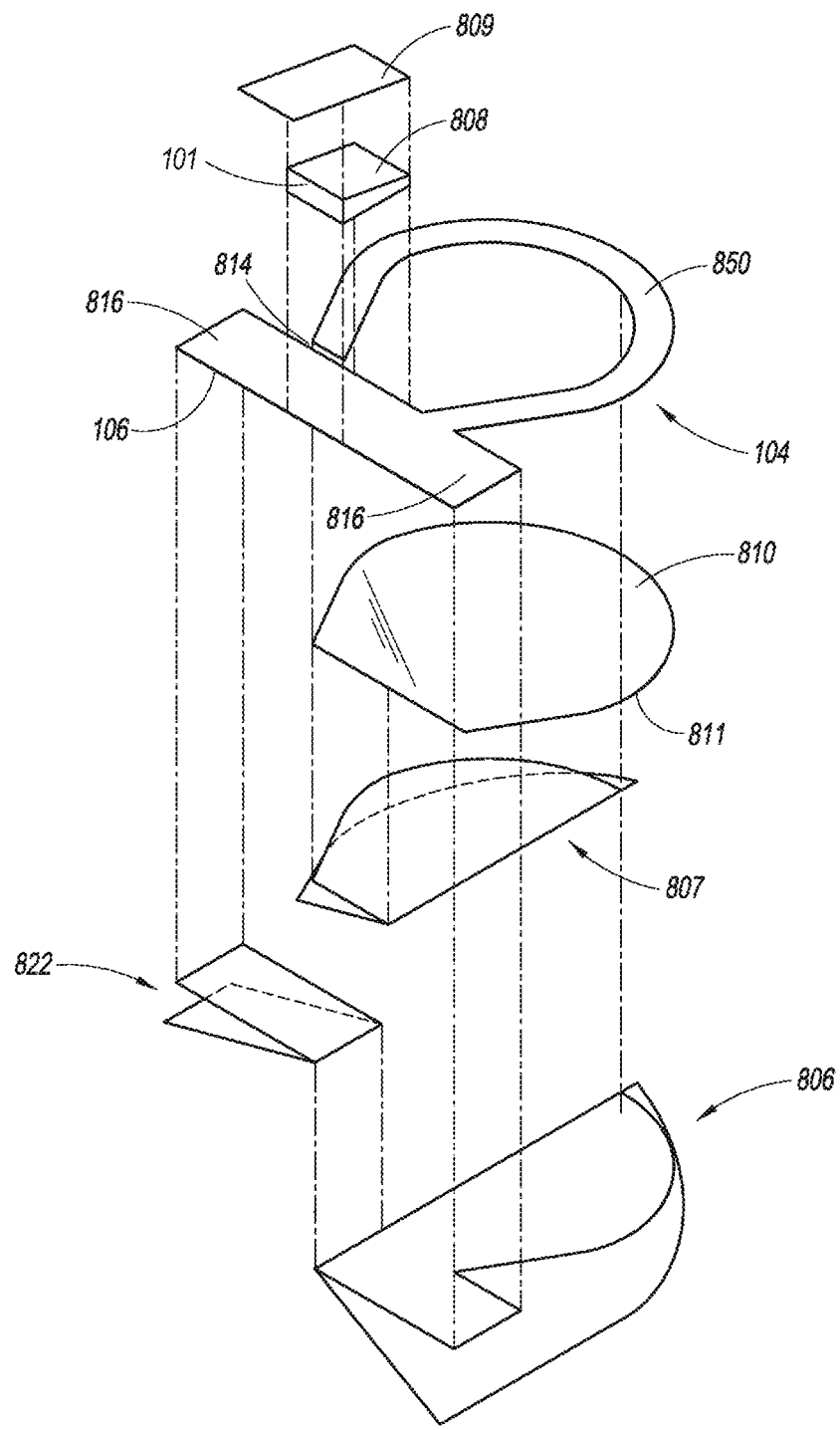
FIG. 72 is an exploded view of the securement device of FIG. 69.
Figure 73:
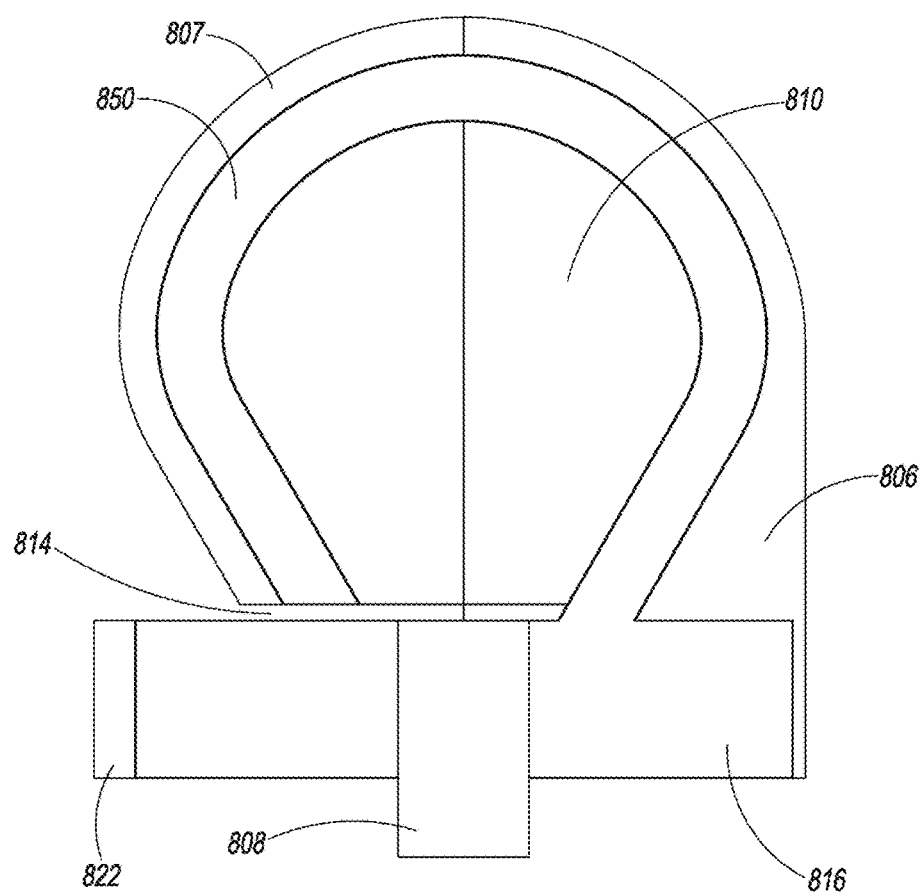
FIG. 73 is a top view of a securement device of FIG. 69 including a plurality of liners on the bottom surface of the device.

FIG. 72 is an exploded view of the securement device 800. Double sided tape 808 may be disposed on a top surface of the retainer 101. The retainer 101 may disposed on the anchor pad 104 in generally the center of the winged portion 816 of the anchor pad 104. The underside of the anchor pad 104 may be covered by an adhesive layer. A portion of the underside of the adhesive layer 106 may be covered by a film 810. In some embodiments, at least the outer most portions or outside perimeter of the adhesive layer is not covered by the film 810. In some embodiments, the underside 811 of the film 810 includes an adhesive layer. Removable liner 809 may cover the adhesive surface 808 of the retainer 101. Removable liners 806, 807, and 822 can be disposed on the underside of the anchor pad 104 and film 810. The removable liners 806, 807, 809, and/or 822 may include fold over sections forming pull tabs as discussed above.

Figure 74:
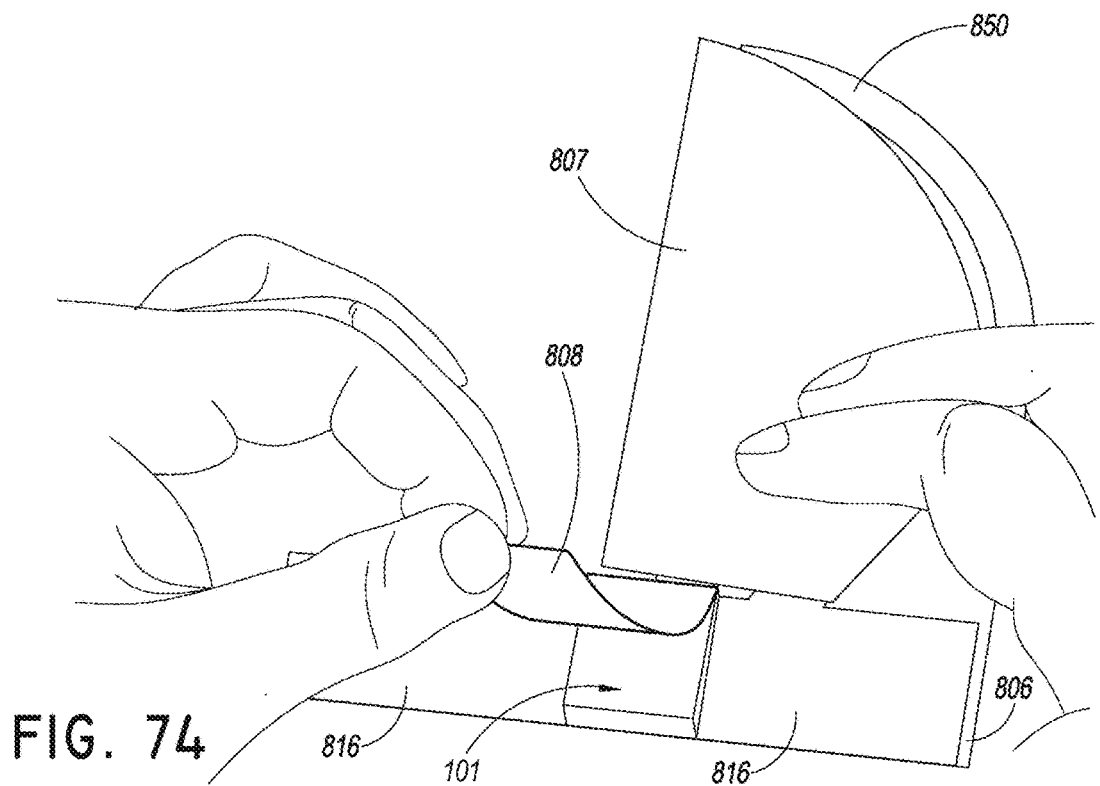
FIG. 74 is a top view of a method of using the securement device of FIG. 69. As shown, the method can begin by removing a liner disposed over the retainer and folding over the anchor pad along a slot.

In operation, a method of using the securement device 800 and a process for coupling a medical article to a patient can begin by folding over the loop portion 850 of the anchor pad 104 away from the slot side of the anchor pad 104 and removing a release liner 808 covering the top adhesive surface of the retainer 101 as shown in FIG. 74

Figure 75:
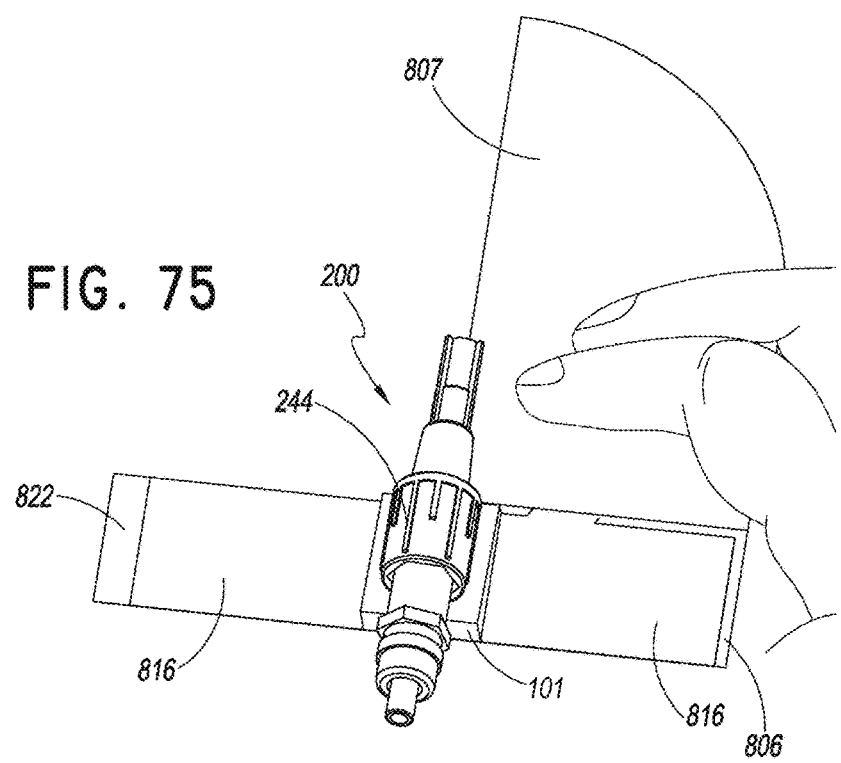
FIG. 75 is a top view of a method of using the securement device of FIG. 69. As shown, the method can continue by removing a liner and sliding the securement device between the patient's skin and the medical article while guiding the medical article through the slot.
Figure 76:
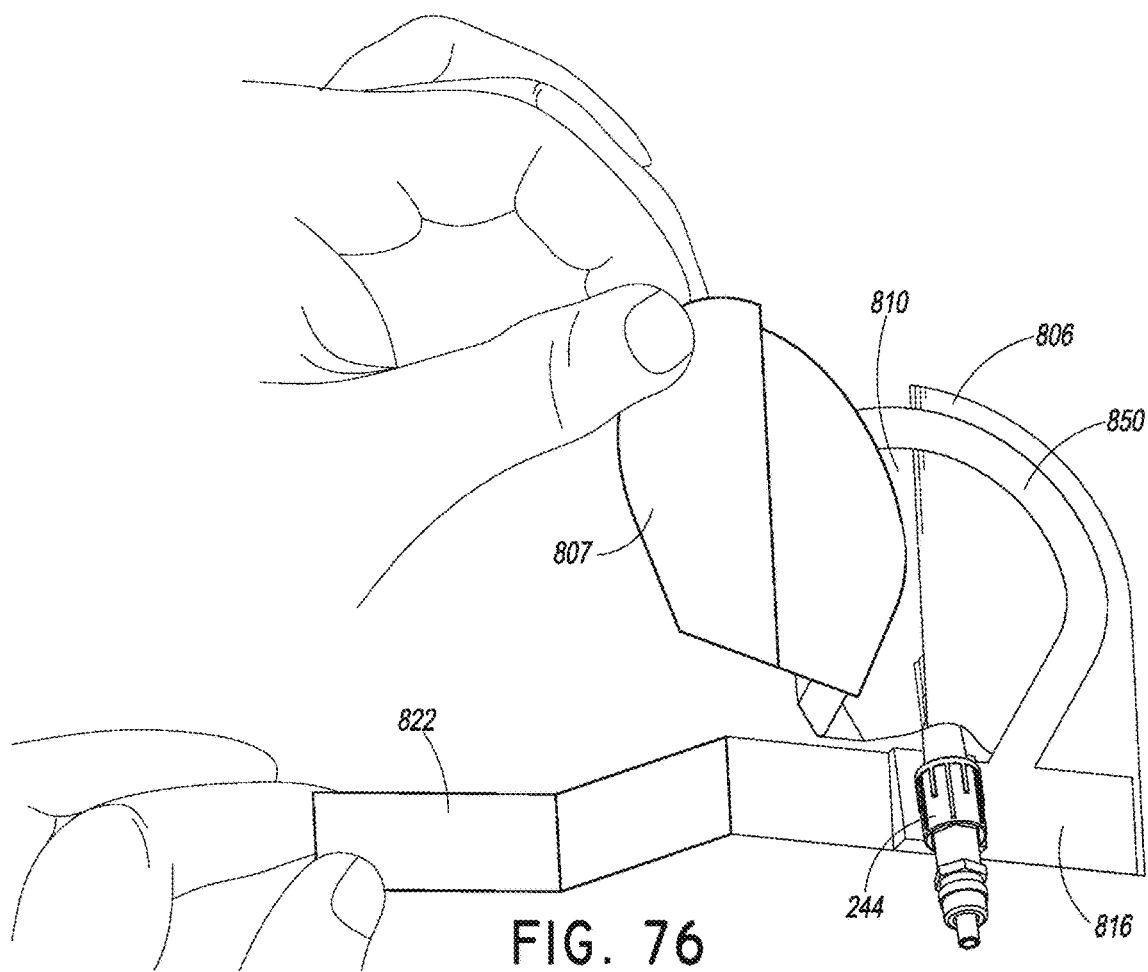
FIG. 76 is a top view of a method of using the securement device of FIG. 69. As shown, the method can continue by removing liners from a bottom surface of the dressing and the anchor pad and attaching them to the patient.
Figure 77:
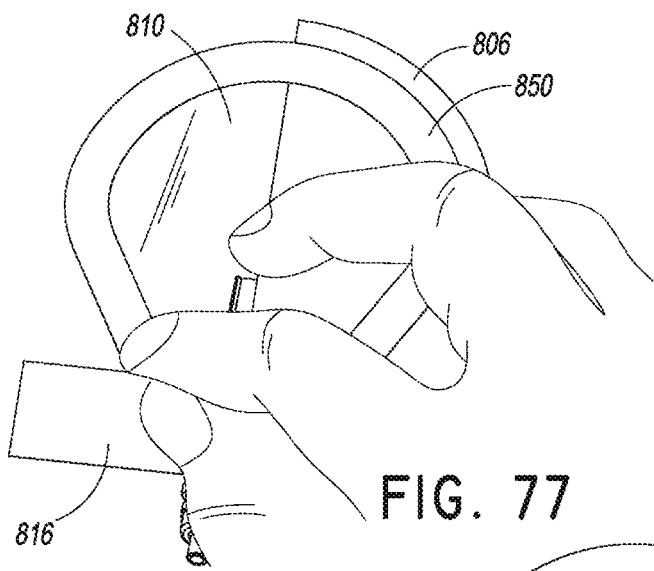
FIGS. 77-78 are top views of a method of using the securement device of FIG. 69. As shown, the method can continue by removing an additional liner from a bottom surface of the dressing.
Figure 78:
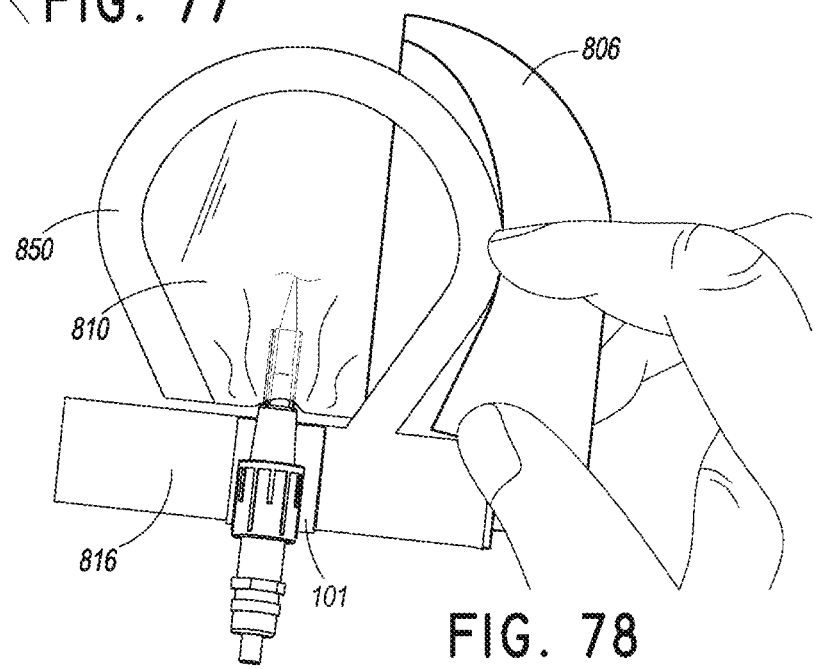
Figure 79:
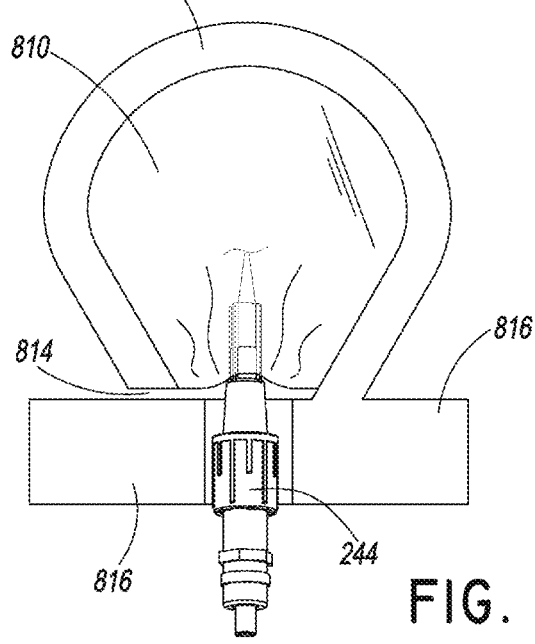
FIG. 79 is a top view of a securement device of FIG. 69 with the dressing secured over the medical article and the securement device attached to the patient.

The process can continue by positioning the securement device 800 such that the retainer 101 is positioned below a portion of the medical article 200 as shown in FIG. 75. The process continues as shown in FIG. 76 by removing the release liner 822 covering the adhesive surface of the underside of the winged portion 816 of the anchor pad 104. The release liner 807 covering a about a half of the lower surface of the loop portion 850 of the anchor pad 104 can then be removed as well. Thus, the slot side of the loop portion 850 of the anchor pad 104 is adhered to the patient's skin as shown in FIG. 77. The second liner 806 covering the remaining portion of the adhesive layer on the lower surface of the anchor pad 104 and/or covering the film 810 is removed as shown in FIG. 78. The medical article is thus secured to the patient as shown in FIG. 79.

The securement devices described herein may include a support member to support portions of the medical article extending distal of the retainer, for example retainer 101, and/or distal of the recess in the retainer, for example recess 108. For instance, certain catheters may have longer lengths or be attached to extension tubing that is advantageously supported by a support member. The support member may be made of any suitable material, for example, foam or plastic, and in one embodiment is formed from the same material as the retainer, for example retainer 101. The support member may be a separate component from the securement device or may be integral to the securement device, for example as an extension of the retainer. The support member may include a section configured to attach to a catheter portion or extension tube portion extending distal of the retainer, such as by friction fit (e.g., snapping onto the catheter portion). The support member may be connected to the securement device, for example at the distal end of the retainer, along a fold line or perforation line so that the support member can be either connected to or separate from the retainer. In one embodiment, the support member may be connected to the dressing.

Figure 80:
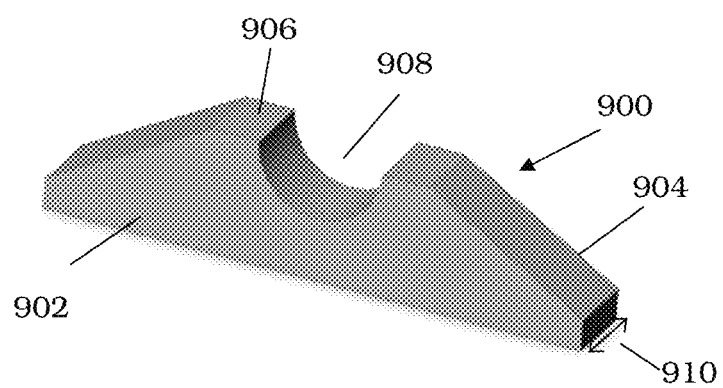
FIGS. 80 and 83 are perspective views of support members.
Figure 81:
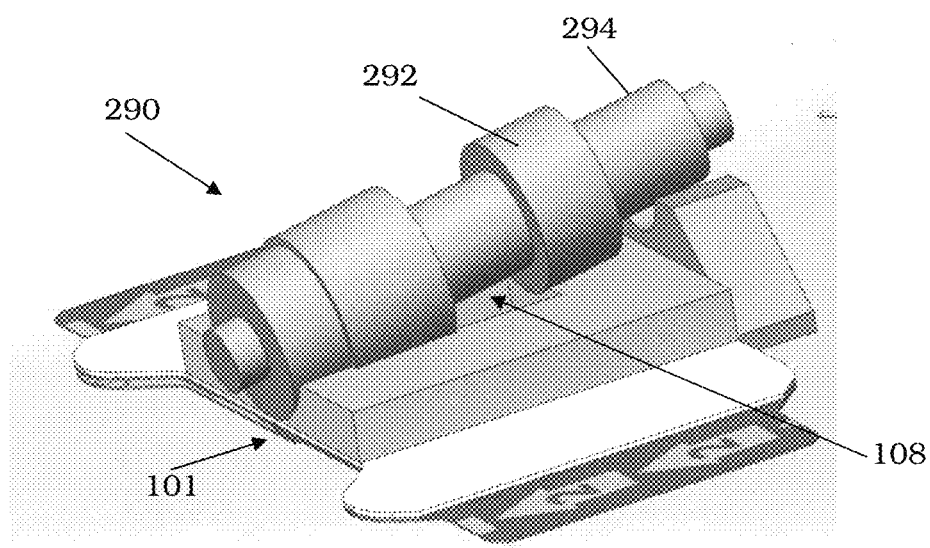
FIGS. 81-82 are perspective views of a securement device with the support member of FIG. 80.
Figure 82:
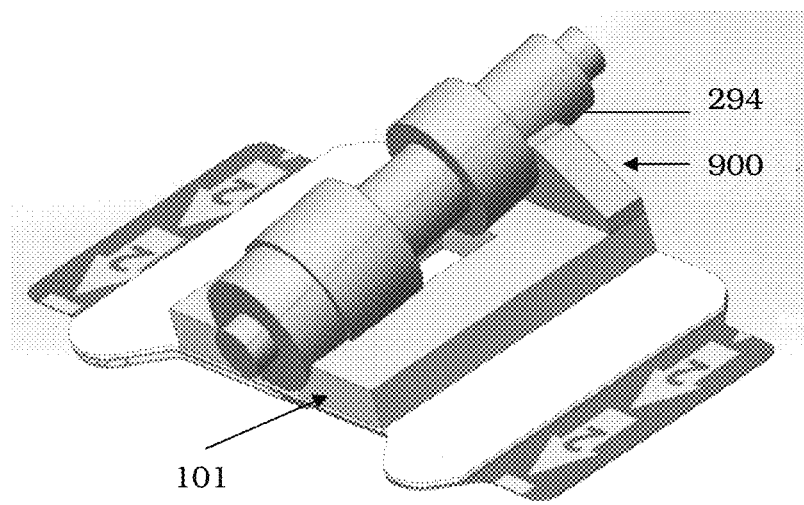

FIG. 80 illustrates one embodiment of a support member 900. The support member 900 has a front face 902, a rear face 904, and a channel 908 extending from a top surface 906. The support member 900 has a thickness 910. FIG. 81 illustrates one example of support member 900 in use with a securement device including retainer 101. Catheter 290 is supported by the securement device and includes portions in the channel 108. Catheter portions 292 and 294 extend beyond channel 108, and catheter portion 294 is supported by support member 900. In FIG. 81, catheter portion 294 is shown resting in channel 908 but not entirely within the channel 908, and support member 900 is positioned distal of retainer 101 abutting a rear portion thereof. Support member 900 can be a separate component, unattached or attached in some manner to the rear face of retainer 101 (e.g., via adhesive), or can be integral to retainer 101 as an extension thereof. FIG. 82 illustrates one example of support member 900 extending from a top face of retainer 101. Again, support member 900 can be a separate component, unattached or attached in some manner to the rear face of retainer 101 (e.g., via adhesive), or can be integral to retainer 101. In one embodiment, support member 900 in FIG. 81 can be folded along a fold line away from the top surface of the retainer while remaining connected thereto. In the embodiment of FIG. 81, catheter portion 294 is shown entirely within channel 908, for example in a friction fit arrangement so that catheter 290 is releasably locked to support member 900.

Figure 83:
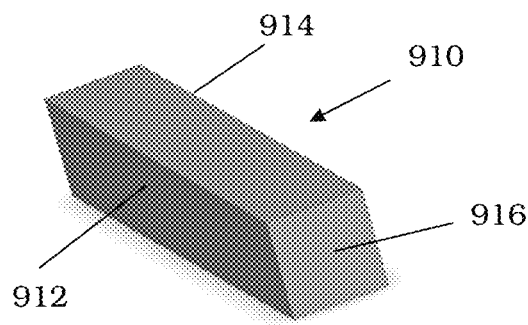
Figure 84:
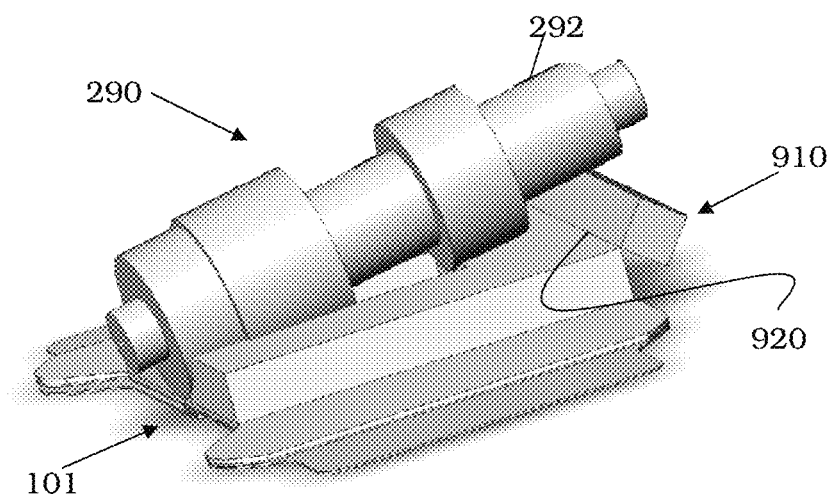
FIGS. 84-85 are perspective views of a securement device with the support member of FIG. 83.
Figure 85:
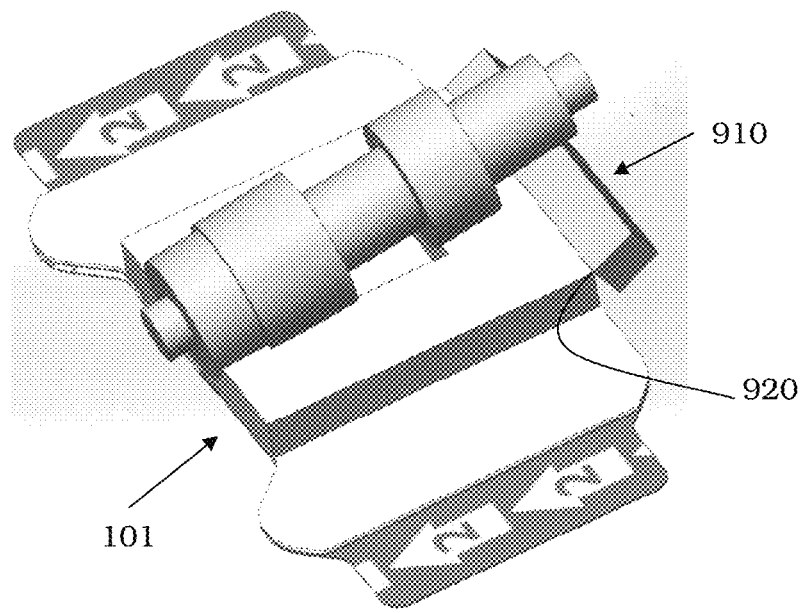

FIG. 83 illustrates one embodiment of a support member 910. The support member 910 has a front face 912, a rear face 914 and a side face 916. The support member 910 is shown formed as a particular prism shape, but other geometric shapes are also contemplated, for example a rectangular prism, triangular prism, hexagonal prism, cylinder, etc. FIGS. 84-85 illustrate different views of support member 910 associated with retainer 101 of a securement device. Catheter portion 292 is shown resting on an edge between surfaces of the support member 910. Support member 910 can be a separate component, unattached or attached in some manner to the rear face of retainer 101 (e.g., via adhesive), or can be integral to retainer 101 as an extension thereof. In FIGS. 84-85, support member 910 is shown attached to retainer 101 along fold line 920 that permits support member 910 to be folded from a non-use position (not shown) to a use position in which the support member is angled with respect to the retainer 101. In one embodiment, fold line 920 is perforated to facilitate separation of the support member 910 from the retainer. Although the support members 900 and 910 are shown coupled to the retainer in FIGS. 81-82 and 84-85, it is also contemplated that the support members could be coupled to other aspects of the securement device, such as, for example, the anchor pad or dressing.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a stabilization system, and stabilization systems that include one or more of the features herein described can be designed for use with a variety of medical articles.

The various embodiments of the securement devices and systems described above in accordance with the present invention thus provide a means to secure a medical article a patient. The insertion site of a catheter attached to the connector fitting or extension set may be covered with a dressing.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the features of the retainers disclosed in the various embodiments can be switched between embodiments. In addition to the variations described herein, other known equivalents for each feature can be mixed and matched by one of ordinary skill in this art to construct stabilization systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A stabilization device, comprising:
a retainer including a recess designed to accommodate a first external portion of a catheter assembly;
a support member coupled to a distal side of the retainer, the support member designed to support a second external portion of the catheter assembly distal of the first external portion;
an anchor pad coupled to a bottom surface of the retainer; and
a hemostatic dressing designed to cover the retainer and the anchor pad, the hemostatic dressing comprising an adhesive surface covered by a dressing liner to be removed prior to positioning the hemostatic dressing over the retainer and the anchor pad, wherein the hemostatic dressing comprises an anti-microbial material.

2. The stabilization device according to claim 1, wherein the anti-microbial material is a coating over the adhesive surface.

3. The stabilization device according to claim 1, wherein the hemostatic dressing comprises an occlusive layer.

4. The stabilization device according to claim 3, wherein the occlusive layer comprises one or more oligodynamic metal salts or oxides, or a combination of oligodynamic metal salts and oxides, wherein the one or more oligodynamic metal salts or oxides are included in the anti-microbial material.

5. The stabilization device according to claim 3, wherein the occlusive layer comprises an absorbent acrylic, an alginate, a foam, a hydrocolloid, and/or a hydrogel material.

6. The stabilization device according to claim 5, further comprising a silver material, wherein the silver material is a silver salt, colloid, or complex.

7. The stabilization device according to claim 1, wherein the retainer comprises an elastomer material.

8. The stabilization device according to claim 1, wherein the anti-microbial material is incorporated into at least one of the retainer and the anchor pad.

9. The stabilization device according to claim 8, wherein the anti-microbial material is an anti-microbial pad, and wherein the anti-microbial pad is integral to at least one of the retainer and the anchor pad.

10. The stabilization device according to claim 1, wherein the support member is separate from the retainer.

11. The stabilization device according to claim 10, wherein the support member is coupled to the distal side of the retainer via an adhesive.

12. The stabilization device according to claim 1, wherein the support member is integral with the retainer.

13. The stabilization device according to claim 12, wherein the support member extends from an upper side of the retainer.

14. The stabilization device according to claim 1, wherein the support member is separable from the retainer via a perforation.

15. The stabilization device according to claim 1, wherein the support member includes a channel configured to receive the second external portion of the catheter assembly extending distally of the recess.

16. The stabilization device according to claim 15, wherein the channel of the support member is configured to releasably lock the support member to the catheter assembly.

17. The stabilization device according to claim 1, wherein the support member is coupled to the retainer along a fold line, the support member configured to fold from a non-use position to a use position.

18. The stabilization device according to claim 1, wherein the support member has a prism shape.

19. The stabilization device according to claim 1, wherein the retainer comprises a flat top surface, and wherein the recess extends from the flat top surface to the bottom surface.

20. The stabilization device according to claim 19, wherein the flat top surface includes an adhesive.

21. The stabilization device according to claim 1, wherein the retainer further comprises a channel having a distal end in communication with the recess and a proximal end in communication with a proximal side of the retainer, the channel including opposing first and second sides separated by a first lateral width, wherein the first lateral width is less than a second lateral width of the recess at the distal end of the channel.

22. The stabilization device according to claim 21, wherein the recess has a rectangular shape with a proximal side of the recess parallel to a distal side of the recess and a first lateral side parallel to a second lateral side.

23. The stabilization device according to claim 1, wherein the hemostatic dressing comprises a pad layer and a transparent film layer, the pad layer having a first window to provide visibility of the catheter assembly when the hemostatic dressing is placed over the stabilization device.

24. The stabilization device according to claim 23, wherein the pad layer includes a second window to provide visibility of an insertion site of the medical article when the dressing is placed over the stabilization device.

25. The stabilization device according to claim 1, wherein the anchor pad includes an upper layer and a lower surface.

26. The stabilization device according to claim 25, wherein the upper layer comprises a foam material.

27. The stabilization device according to claim 25, wherein the anchor pad includes an inner foam layer positioned between the upper layer and the lower surface.

28. The stabilization device according to claim 25, wherein the lower surface includes a lower surface adhesive comprising a silver material.

29. The stabilization device according to claim 1, further comprising a first release liner positioned on an adhesive lower surface of the anchor pad, the first release liner having an end extending beyond a first side of the anchor pad.

30. The stabilization device according to claim 29, wherein the end of the first release liner comprises a first tab including numbering designed to indicate an order for use of the stabilization device.

31. The stabilization device according to claim 29, further comprising a second release liner positioned on the adhesive lower surface of the anchor pad, the second release liner having an end extending beyond a second side of the anchor pad.

32. The stabilization device according to claim 31, wherein the end of the second release liner comprises a second tab including numbering designed to indicate an order for use of the stabilization device.

33. The stabilization device according to claim 31, wherein the first release liner covers a first half of the adhesive lower surface of the anchor pad, and wherein the second release liner covers a second half of the adhesive lower surface of the anchor pad.

34. The stabilization device according to claim 33, wherein the first release liner includes a first interface portion that contacts the adhesive lower surface of the anchor pad and a first folded portion that includes the end of the first release liner.

35. The stabilization device according to claim 34, wherein the second release liner includes a second interface portion that contacts the adhesive lower surface of the anchor pad and a second folded portion that includes the end of the second release liner.

\* \* \* \* \*